(12) United States Patent
Wu et al.

(10) Patent No.: US 8,772,311 B2
(45) Date of Patent: Jul. 8, 2014

(54) HARMINE DERIVATIVES, INTERMEDIATES USED IN THEIR PREPARATIONS, PREPARATION PROCESSES AND USE THEREOF

(75) Inventors: Jialin Wu, Urumqi (CN); Qi Chen, Guangzhou (CN); Rihui Cao, Guangzhou (CN); Fusheng Yu, Urumqi (CN); Zihou Wang, Beijing (CN); Wenlie Peng, Guangzhou (CN)

(73) Assignee: Xinjiang Huashidan Pharmaceutical Research Co., Ltd., Urumqi (CN)

( * ) Notice: Subject to any disclaimer, the term of this patent is extended or adjusted under 35 U.S.C. 154(b) by 1606 days.

(21) Appl. No.: 10/559,824

(22) PCT Filed: Jun. 2, 2004

(86) PCT No.: PCT/CN2004/000591
§ 371 (c)(1), (2), (4) Date: Apr. 24, 2006

(87) PCT Pub. No.: WO2004/106335
PCT Pub. Date: Dec. 9, 2004

(65) Prior Publication Data
US 2009/0227619 A1    Sep. 10, 2009

(30) Foreign Application Priority Data
Jun. 2, 2003   (CN) ..................... 3136406

(51) Int. Cl.
*A61K 31/437* (2006.01)
*C07D 487/04* (2006.01)

(52) U.S. Cl.
USPC .......................................... 514/290; 546/80

(58) Field of Classification Search
USPC ........................................ 546/80; 514/290
See application file for complete search history.

(56) References Cited

U.S. PATENT DOCUMENTS

| 4,371,536 A | 2/1983 | Braestrup et al. |
| 4,628,057 A | 12/1986 | Iijima et al. |

FOREIGN PATENT DOCUMENTS

| BE | 612725 | * | 7/1962 |
| CN | 1215333 | | 4/1999 |
| CN | 1358720 | | 7/2002 |
| DE | 19807993 | | 9/1999 |
| EP | 0030254 | | 6/1981 |
| EP | 0148660 | | 7/1985 |
| EP | 1209158 | | 5/2002 |
| JP | 57-169481 | | 10/1982 |
| WO | 97/37658 | | 10/1997 |
| WO | 00/33839 | | 6/2000 |
| WO | 03/022849 | | 3/2003 |

OTHER PUBLICATIONS

[2,3] Fused indoles : , Chritopher Moody et al, 1984 , J. Chem. Soc. Perkin Trans. I.*
Cabrera, G.M. et al., "A β-Carboline Alkaloid for the Soft Coral Lignopsis spongiosum", Journal of Natural Products, 62(5), 759-760 CODEN: JNPRDF; ISSN: 0163-3864, 1999.
Srivastava, S.K. et al., "Potent 1, 3-disubstituted-9H-pyrido [3,4-b] indoles as New Lead Compounds in Antifilarial Chemotherapy", Journel of Medicinal Chemistry, 42(9), 1667-1672, 1999.
Voelker, T. et al., "o-Nitrobenzyl as a Photocleavable Nitrogen Protecting Group for Indoles, Benzimidazole, and 6-Chlorouracil", Tetrahedron Letters, 39, 1998, 359-362.
Dekhane, M. et al., "N-2 Methylated Quaternary Derivatives of β-Carboline-3-Carboxylates inhibit Acetylcholinesterase in vitro", Bioorganic & Medicinal Chemistry letters, Oxford, GB, vol. 3, No. 12, 1993, 2831-2836.
Molina, P. et al., "Iminphosphorane-mediated synthesis of 1-substituted-β-carbolines: investigative studies on the preparation of alkoloids lavendamycin and eudistomins framework", Tetrahedron Letters, 33(20), 2891-4, 1992.
Cegla, M. et al., "Synthesis of esters of 1-pyridyl-.beta.-carboline-3-carboxylic acid", Pharmazie, 43(7), 510 CODEN: PHARAT; ISSN 0031-7144, 1988.
Database CAPLUS (online), Chemical Abstracts Service, Columbus, Ohio, US; Longo, V.G. et al., "Effects of drugs on the electrical activity of the red nucleus in the rabbit. Activation of benzodiazepine and barbiturate receptors.", retrieved from STN database accession No. 1989:88376.

(Continued)

*Primary Examiner* — Rita Desai
(74) *Attorney, Agent, or Firm* — Weaver Austin Villeneuve & Sampson LLP

(57) ABSTRACT

This invention relates to compounds of general formula (I), wherein $R_1$, $R_2$, $R_3$, $R_4$ and $R_5$ are as defined in the specification; intermediates used in their preparation, preparation processes and use thereof. The present invention produces new harmine derivatives with enhanced antitumor activity and lower nervous system toxicity by structurally modification of the parent structure of β-carboline of harmines at position 1, 2, 3, 7 and 9. The compounds of the present invention can be prepared easily with high yield. They can be used in manufacture of a variety of antitumor medicines and medicines used in treatment of tumor diseases in combination of light or radiation therapy.

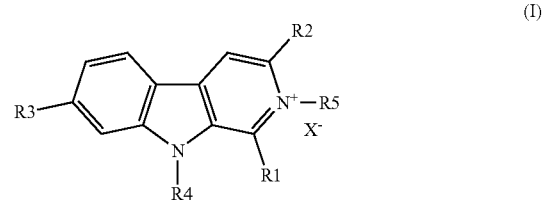

(I)

3 Claims, 15 Drawing Sheets

(56) References Cited

OTHER PUBLICATIONS

Database CAPLUS (online), Chemical Abstracts Service, Columbus, Ohio, US; Mehta, P. et al., "Synthesis of substituted pyrido [3, 4-b] indole-3-carboxamides and related compounds as benzodiazepine receptor agonists/antagonists", retrieved from STN database accession No. 1988:528862.
Database CAPLUS (online), Chemical Abstracts Service, Columbus, Ohio, US; 1960, Yakovleva, A.P. et al., "Alkaloids of *Ammothamnus songoricus*", retrieved from STN database accession No. 1960:7408.
Database CAPLUS (online), Chemical Abstracts Service, Columbus, Ohio, US; Nakagawa, M. et al., "Synthesis of fumitremorgin B and related compounds", retrieved from STN database accession No. 1988:55714.
Database CAPLUS (online), Chemical Abstracts Service, Columbus, Ohio, US; ".beta.-Carbolines", retrieved from STN database accession No. 1983:126057.
Hammond, M. et al., "Structure-Activity Relationships in a Series of NPY Y5 Antagonists: 3-Amido-9-ethylcarbazoles, Core-Modified Analogues and Amide Isosteres", Bioorganic & Medicinal Chemistry Letters, Oxford, GB, vol. 13, No. 8, Jun. 2003, 1989-1992.
Yang Ming et al., "Novel 3-substituted beta-carboline compound having anti-HIV and anti-cancer activity", English translation of CN1358720, published Jul. 17, 2002.
EP patent application No. 04735720.7, Examination Report mailed Apr. 20, 2009.
EP patent application No. 04735720.7, Supplemental Search Report mailed Mar. 14, 2008.
JP patent application No. 2006-508098, Decision of Rejection mailed Jan. 24, 2012.
Duan Jinao et al., "Studies on the chemical constituents of peganum multisectim max in the alkoloids from seeds and antitumour activity", Journal of China Pharmaceutical University, 29 (1), 1998, pp. 21-23.
Li Chunjie et al., "Isolation and identification of anticancerous chemical component in peganum L. and their pharmacologic experimental research", ACTA Academiae Medicinae XinJiang. vol. 10 No. 1, 1987.
"The in vitro use of the mixed alkaloids of paganum harmala 5L to treat the human hela cells of cervical carcinoma", 1985.

Pan Qi-Chao et al., "The antitumor effect of indole alkaloid 5n from paganum harmala L.", Cancer Institute, Sun Yat-sen university of Medical Sciences. Apr. 4, 1985, pp. 192-194.
Pan Qichao et al., "Studies of the pharmacological action of the total alkaloid of peganum harmala", Acad J. Sums, 1997 18 (3), pp. 165-167.
Yang Xiao-ping et al., "Inhibitory effect of the total alkaloid of peganum on human liver and gastric cancer cell line in vitro and xenograft in nude mice", Cancer Institute, Sun Yat-sen University of Medical Sciences, Jun. 10, 1991, pp. 463-465.
Xu Zhao-dong et al., "Study on antitumor effect of harmaline", Cancer Institute, Sun Yat-Sen University of Medical Sciences, Feb. 8, 1989, pp. 94-97.
Zhang Chunli et al., "Distribution and radioimmunoimaging of 1-anti-human bladder carcinoma McAb in nude mice with tumor xenografts", Apr. 9, 1992.
Hu Hai-tang et al., "The effects of TAH on hepatoma cell cytokinetics in mice", Cancer Institute, sun Yat-sen University of Medical Sciences, Jun. 12, 1993, pp. 489-489-491.
Halothane, Harmalline, Harmalol, Hederagenin, definitions of, 1977.
Junko Ishida et al., "Anti-AIDS agents. 46[1] Anti-HIV activity of Harman, an Anti-HIV principle from *Symplocos setchuensis*, and its derivatives", J. Nat. Prod. 2001, 64, 958-960.
Dodd et al., "Mild synthesis of N-ACYL-β-Carboline anhydro-bases using trifluoromethabesulfonates", Heterocycles, vol. 28, No. 2, 1989, pp. 365-380.
Junko Ishida et al. "Antitumor agents 201.[1] cyctotoxicity of harmine and β-carboline analogs", Bioorganic & Medicinal Chemistry Letters 9 (1999) 3319-3324.
PCT/CN2004/000591. International Search Report mailed Sep. 9, 2004.
Yang Xiaoping et al., "The effect of harmine on cultured hela cells", Cancer Institute. Sun Yat-sen University of Medical Sciences, Jan. 7, 1986, pp. 44-45.
Xie Yan et al., "Study of TAH-induced apoptosis in HELA cells", Cancer Institute, Sun Yat-sen University of Medical Sciences, May 1998, vol. 19 No. 3, pp. 131-133.
Szantay C. et al., "Corynantheine, Yohimbine, and Related Alkaloids", The Alkaloids, vol. 27, 1986, pp. 131-407.

* cited by examiner

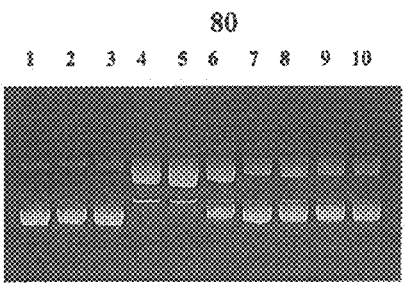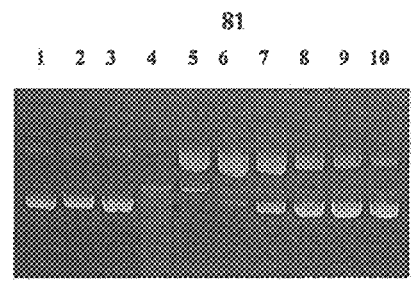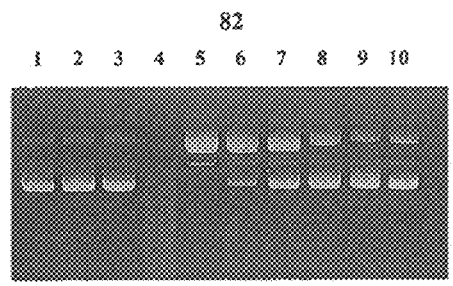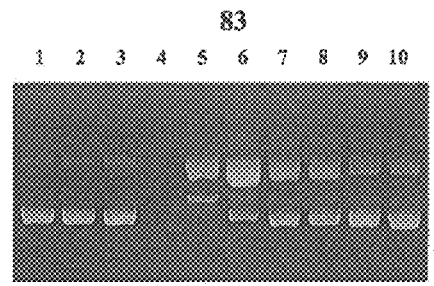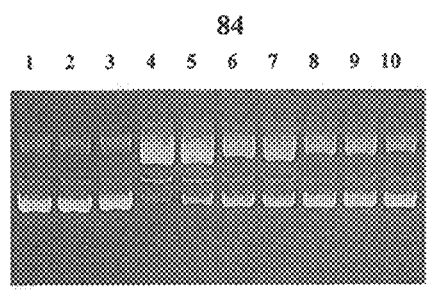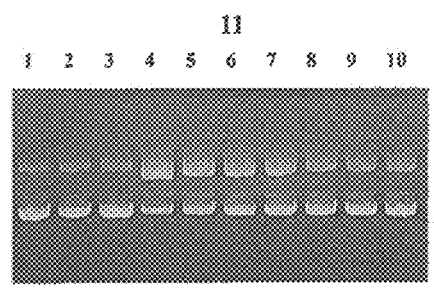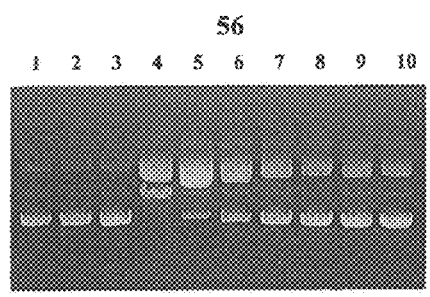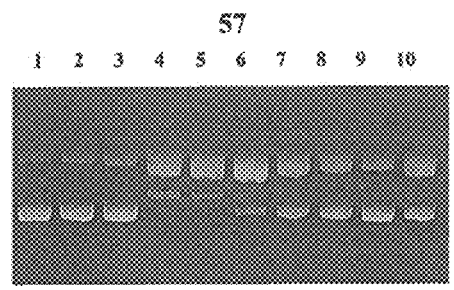
FIG. 1B

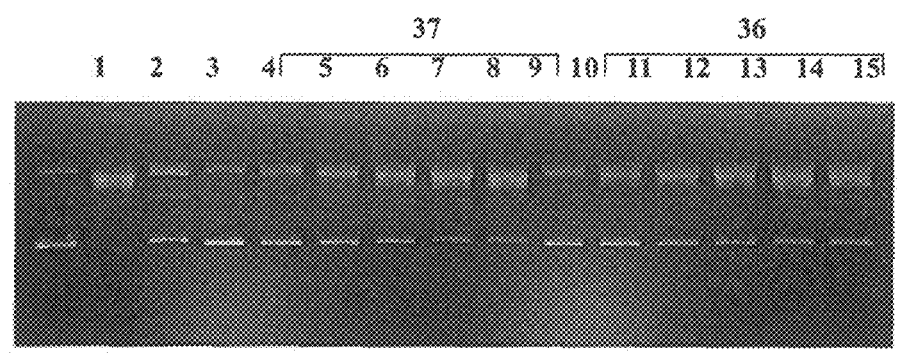
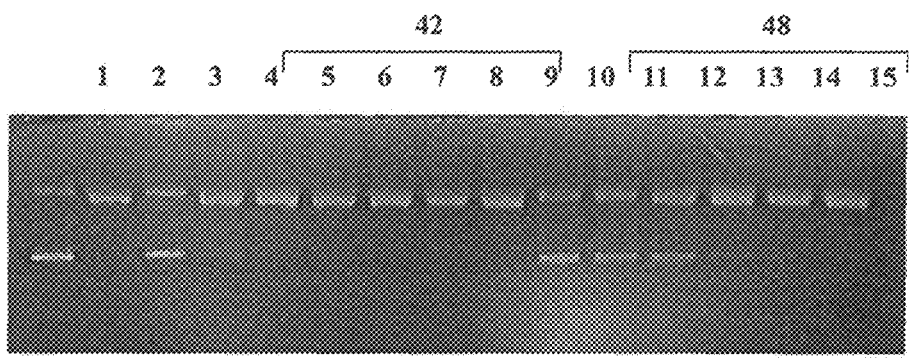
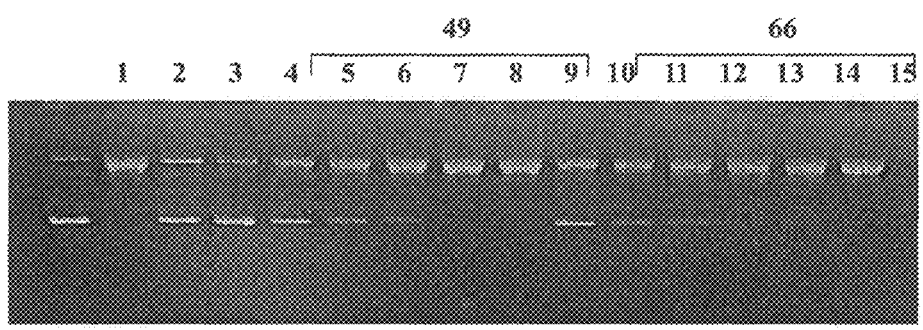
FIG. 4B

A. control
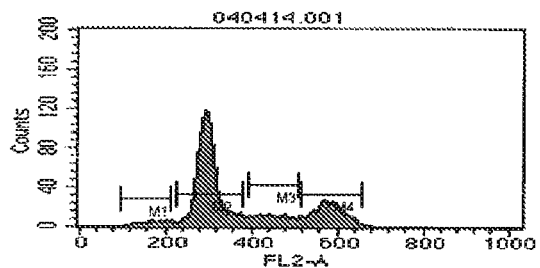
B. 40ug/ml    48hr
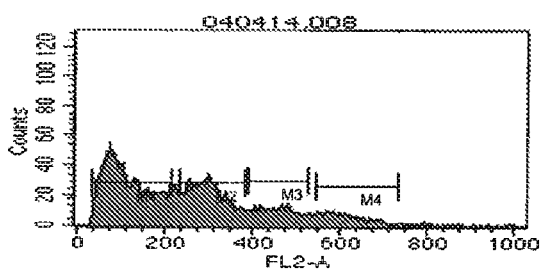
C. 10ug/ml    48hr
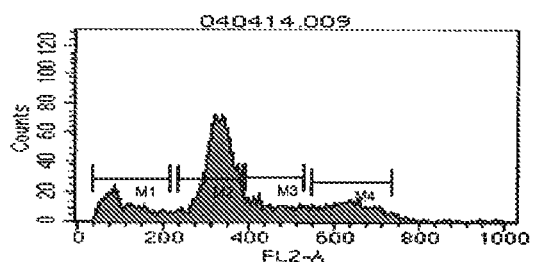
D. 2.5ug/ml    48hr
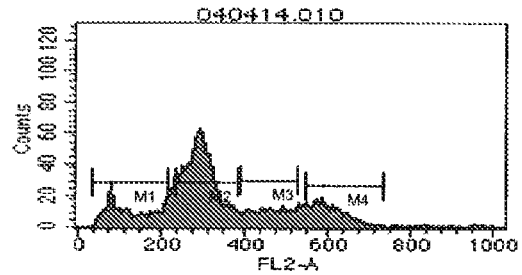
FIG. 6

Negative control (vehicle)
Negative control (vehicle)
Compound 42 100mg/kg
Compound 42 50mg/kg
Compound 36 100mg/kg
Compound 36 50mg/kg
Compound 16 100mg/kg
Compound 16 50mg/kg
Compound 48 100mg/kg
Compound 48 50mg/kg
Compound 86 20mg/kg
Compound 86 10mg/kg
Compound 33 100mg/kg
Compound 33 50mg/kg
positive control
CTX 50mg/kg

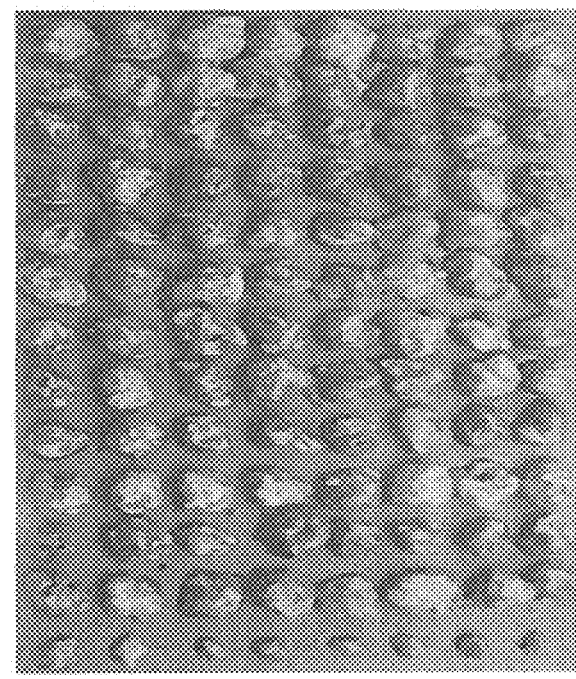

Negative control (vehicle)
Negative control (vehicle)
Compound 37 50mg/kg
Compound 37 25mg/kg
Compound 55 100mg/kg
Compound 55 50mg/kg
Compound 84 100mg/kg
Compound 84 50mg/kg
Compound 11 50mg/kg
Compound 11 25mg/kg
Compound 33 100mg/kg
Compound 33 50mg/kg
positive control
CTX 50mg/kg

FIG. 13

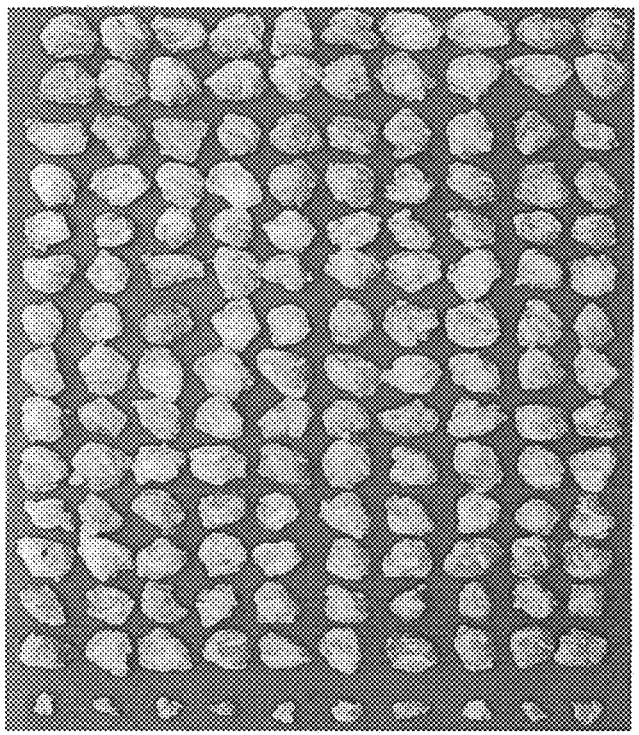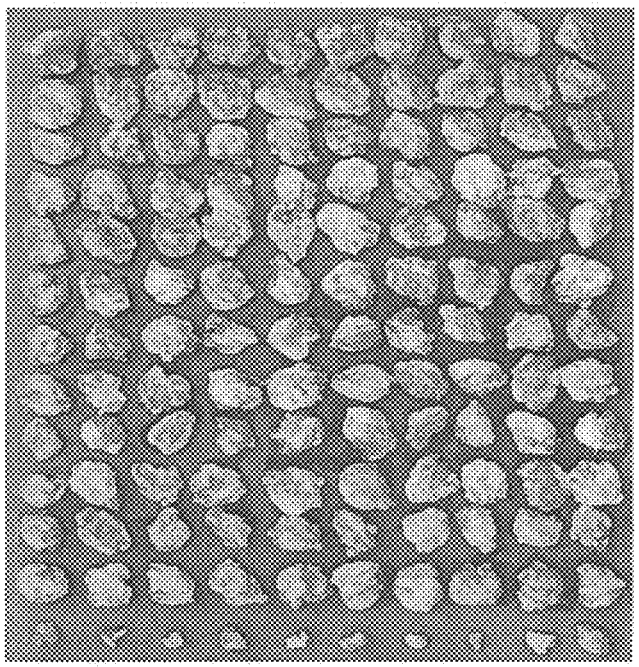
FIG. 14

Synthesis Scheme I
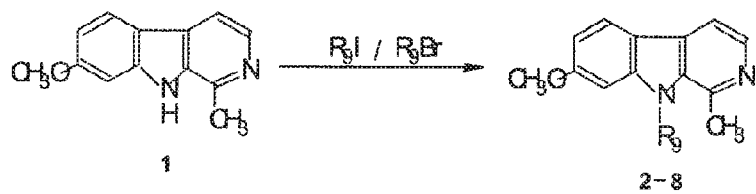
Synthesis Scheme II
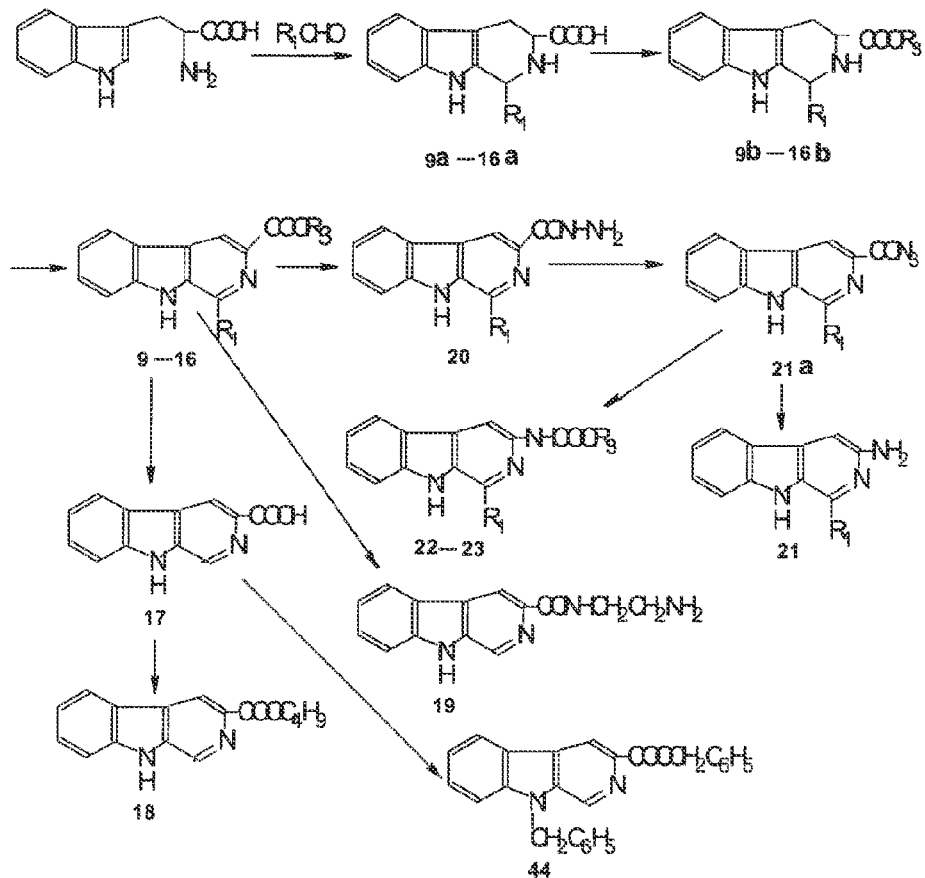
FIG. 15A

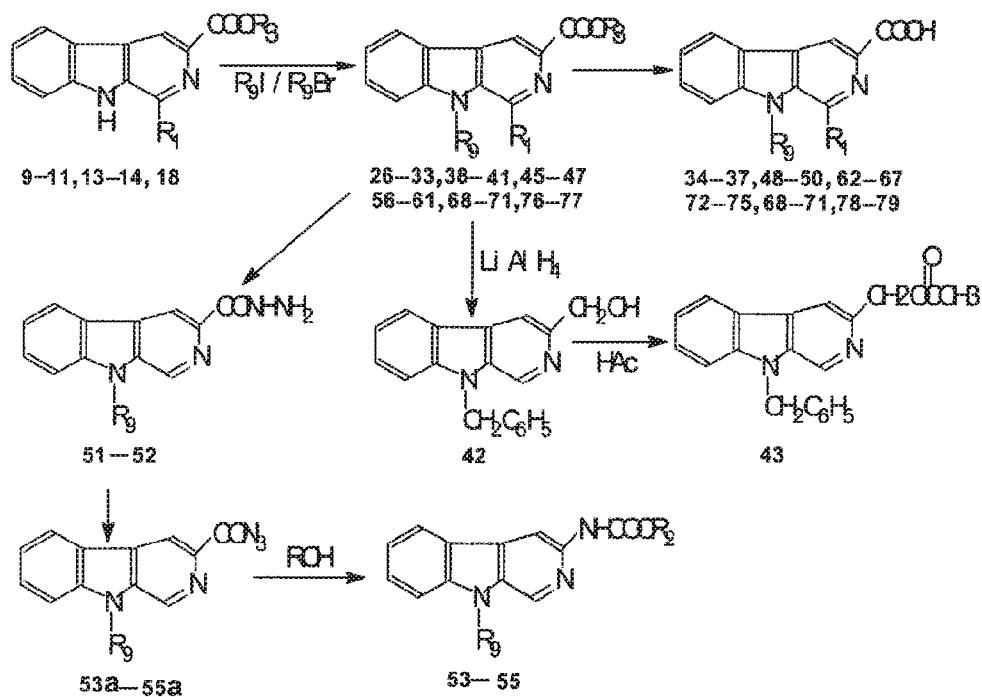
Synthesis Scheme III
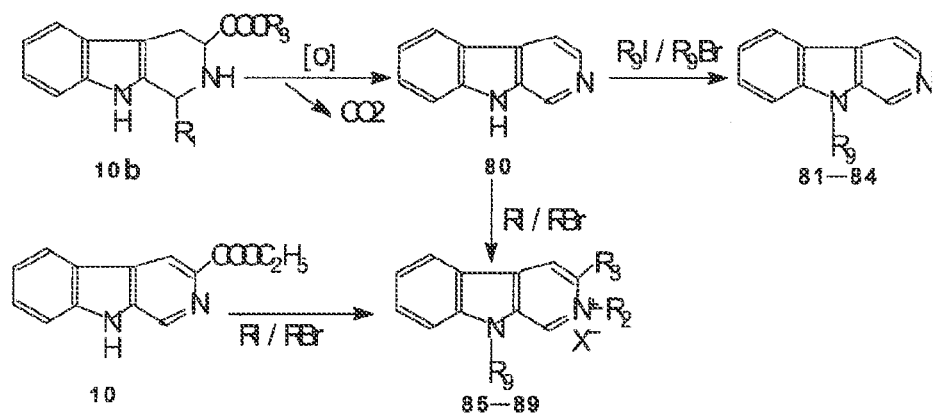
FIG. 15B

HARMINE DERIVATIVES, INTERMEDIATES USED IN THEIR PREPARATIONS, PREPARATION PROCESSES AND USE THEREOF

FIELD OF INVENTION

This invention belongs to the field of pharmaceutical compounds, and specifically relates to alkaloid compounds, and more specifically, to harmine derivatives of formula (I), intermediates used in their preparation, processes for preparing the same and uses thereof.

DESCRIPTION OF THE PRIOR ART

Harmine belongs to the family of β-carboline alkaloids, its chemical name is 7-methoxy-1-methyl-9H-pyrrole[3,4-b]indole, and its molecular formula is $C_{13}H_{12}N_2O$. It has a molecular weight of 212.25 and a melting point of 261° C. The chemical structure of harmine is shown as follows:

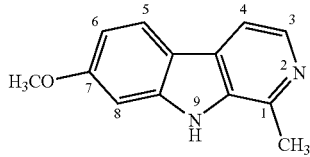

Harmine and its analogs thereof are widely distributed in nature. Numerous researches on the synthesis of harmine derivatives have been reported since harmine was first isolated from *Peganum harmala*. More than 300 harmine derivatives have been reported by far, and the number of new harmine derivatives still keeps increasing.

Previous reports and our preliminary investigation results demonstrated that harmine and its derivatives have significant antitumor activities, but also caused remarkbale acute neurotoxicity characterized by tremble, twitch, and jumping in experimental mice model. Results of investigation on the in vitro anti-tumor activity of harmine and its derivatives showed that these compounds had significant inhibition effect on several cultured tumor cell lines, such as Hela cells (cervical carcinoma), S-180 cells (sarcoma), BEL-7402 cells (hepatoma), MGC-803 cells (gastric carcinoma), CNE2 cells (nasopharyngeal carcinoma), MA782'5S cells (breast cancer) and K562 cells (leucocythemia). Results of investigation on the in vivo antitumor activities of the total alkaloids and mixed alkaloids extracted from *Peganum harmala* plants, dominating ingredients of which were harmine and harmine derivatives, such as harmaline, harmalol and harman, displayed significant therapeutic effect on mice bearing Sarcoma (S180), reticulum cell sarcoma L2 and hepatoma. Moreover, these extracts exhibited significant synergistic effect when combined with cisplatin and adriamycin. However, neurotoxicities were the predominant acute toxic effects observed in mice receiving harmine and its derivatives, the acute toxic effects included tremble, twitch, erection of the tail and eclampsia. Death occurred mostly in the high dosage group. Survival animals would relieve and recover gradually in the next day after administration. Sub-acute toxicity test in rats showed that total alkaloids, extracted from *Peganum harmala* plants, can induce renal pathological change and kidney is the toxic target organ of the total alkaloids. Meanwhile, harmine and its derivatives do not exhibit obvious toxicity toward hemopoietic system, immune system, and reproductive system. What's more, long-term toxic side effects are not obvious.

Though present harmine and its analogs thereof have significant anti-tumor activity, they have also remarkable neurotoxicity. There are still no compounds having significant anti-tumor activity, together with low neurotoxicity, clinically used as anti-tumor medicaments.

OBJECT OF THE INVENTION

The objects of this invention are to overcome the above defects of the prior art, and provide novel harmine derivatives with enhanced anti-tumor activity and lower neurotoxicity as well as easy preparation processes with high yields.

One of the objects of this invention is to provide novel harmine derivatives of formula (I).

Another object of this invention is to provide a process for preparing compounds of formula (I).

Another object of this invention is to provide a process for preparing 1,7,9-trisubstituted-β-carboline derivatives.

Another object of this invention is to provide 1,2,3,4-tetrahydro-β-carboline-3-carboxylic acid, esters and salts thereof.

Another object of this invention is to provide 9-substituted β-carboline-3-carboxylic acid, esters and salts thereof.

Another object of this invention is to provide a process for preparing ethyl 9-substituted 1-methyl-β-carboline-3-carboxylate.

Another object of this invention is to provide a process for preparing 2,9-dibenzyl-β-carbolinium iodate.

Another object of this invention is to provide a process for preparing 2,9-dibenzyl-1-methyl-β-carbolinium bromate.

Another object of this invention is to provide intermediate compounds of formula (9a-16a) for the synthesis of said compounds.

Another object of this invention is to provide intermediate compounds of formula (9b-16b) for the synthesis of said compounds.

Another object of this invention is to provide intermediate compounds of formula (21a) for the synthesis of said compounds.

Another object of this invention is to provide intermediate compounds of formula (53a-55a) for the synthesis of said compounds.

Another object of this invention is to provide intermediate compounds of formula (10b) for the synthesis of said compounds.

Another object of this invention is to provide the use of said compounds in the manufacture of a medicament for treating tumors.

Another object of this invention is to provide the use of said compounds in the manufacture of a medicament, combined with phototherapy and radiation therapy, for treating tumors.

SUMMARY OF THE INVENTION

Harmine derivatives of this invention have a structure of the following formula (I):

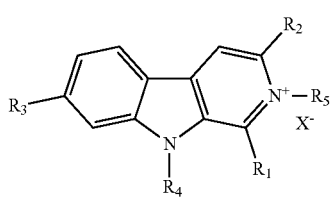

wherein
$R_1$ is hydrogen, $C_{1-6}$ primary, secondary and tertiary linear or branched alkyl, $C_{6-10}$ arylalkyl or 1-5 halogen, nitro or amino arylalkyl, heterocyclic group or alkenyl;

$R_2$ is hydrogen, carboxyl, ester group, carboxylate, acylamino, acyl halide group or $C_{1-6}$ alkoxycarbonyl, aryloxycarbonyl, or heterocyclic oxycarbonyl;

$R_3$ is hydrogen, hydroxyl, $C_{1-6}$ alkoxy, carboxylic esters, carboxylic salts, arylalkoxy, or heterocyclic oxy group;

$R_4$ is hydrogen, $C_{1-6}$ alkyl, $C_{1-6}$ hydroxyalkyl, $C_{6-10}$ arylalkyl or 1-5 halogen arylalkyl, arylhydrocarbyl, arylcarboxyl, aryl ester group, arylamino group, arylnitro group, or heterocyclic group;

$R_5$ is hydrogen, $C_{1-6}$ primary, secondary and tertiary linear or branched alkyl, $C_{6-10}$ arylalkyl and 1-5 substituted arylalkyl, arylhydrocarbyl, arylcarboxyl, aryl ester group, arylamino group, arylnitro group, or heterocyclic group; and $R_1, R_2, R_3$ and $R_4$ do not represent hydrogen at the same time, $X^-$ is a halogen, sulfonic group, sulfuric group, or nitric acid group;

When $R_2$ and $R_4$ are hydrogen, $R_1$ is not methyl and $R_3$ is not methoxy;

When $R_1$ is methyl, $R_2, R_3$ and $R_4$ do not represent hydrogen at the same time;

When $R_1$ is methyl, $R_2$ is hydrogen, and $R_3$ is methoxy, $R_4$ is not methyl, ethyl or butyl; and When $R_1$ and $R_3$ are hydrogen, $R_2$ is not methoxycarbonyl and $R_4$ is not methyl.

In the compounds of the above formula (I), $R_1$ is preferably hydrogen or $C_{1-4}$ alkyl or $C_{6-8}$ arylalkyl.

In the compounds of the above formula (I), $R_1$ is preferably hydrogen or $C_{1-2}$ alkyl.

In the compounds of the above formula (I), $R_1$ is most preferably hydrogen.

In the compounds of the above formula (I), $R_2$ is preferably hydrogen or $C_{1-4}$ alkoxycarbonyl.

In the compounds of the above formula (I), $R_2$ is preferably hydrogen or $C_{1-2}$ alkoxycarbonyl.

In the compounds of the above formula (I), $R_2$ is preferably ethoxycarbonyl.

In the compounds of the above formula (I), $R_3$ is preferably hydrogen, hydroxyl or $C_{1-4}$ alkyloxy.

In the compounds of the above formula (I), $R_3$ is preferably hydrogen.

In the compounds of the above formula (I), $R_4$ is preferably hydrogen, $C_{1-4}$ alkyl, $C_{1-4}$ hydroxyalkyl or $C_{6-8}$ arylalkyl or substituted arylalkyl.

In the compounds of the above formula (I), $R_4$ is preferably hydrogen, $C_{1-2}$ alkyl, $C_{1-2}$ hydroxyalkyl, or $C_{6-8}$ arylalkyl or substituted arylalkyl.

In the compounds of the above formula (I), $R_4$ is preferably ethyl or benzyl.

In the compounds of the above formula (I), $R_4$ is preferably benzyl.

In the compounds of the above formula (I), preferably, $R_1$ is hydrogen, $C_{1-4}$ alkyl or $C_{6-8}$ arylalkyl, $R_2$ is hydrogen, hydroxyl, carboxyl, ester group, carboxylate, halogen or $C_{1-4}$ alkoxycarbonyl, $R_3$ is hydrogen, hydroxyl, or $C_{1-4}$ alkoxy, $R_4$ is hydrogen or $C_{1-2}$ alkyl, $C_{1-2}$ hydroxyalkyl, $C_{6-8}$ arylalkyl or substituted arylalkyl, and $R_5$ is hydrogen, $C_{1-6}$ primary, second, tertiary linear or branched alkyl and $C_{6-10}$ arylalkyl and substituted arylalkyl.

In the compounds of the above formula (I), preferably, $R_1$ is hydrogen, $R_2$ is $C_{1-2}$ alkoxycarbonyl, $R_3$ is hydrogen, and $R_4$ is $C_{1-2}$ alkyl or $C_{6-8}$ arylalkyl or substituted arylalkyl.

In the compounds of the above formula (I), preferably, $R_1$ is hydrogen, $R_2$ is ethoxycarbonyl, $R_3$ is hydrogen, and $R_4$ is ethyl or benzyl.

In the compounds of the above formula (I), preferably, $R_1$ is hydrogen, $R_2$ is ethoxycarbonyl, $R_3$ is hydrogen, and $R_4$ is benzyl.

In the compounds of the above formula (I), most preferably, $R_1$ is methyl, $R_2$ is ethoxycarbonyl, $R_3$ is hydrogen, $R_4$ is pentafluorobenzyl, and $R_5$ is hydrogen.

In the compounds of the above formula (I), most preferably, $R_1$ is hydrogen, $R_2$ is hydrogen, $R_3$ is hydrogen, $R_4$ is benzyl, $R_5$ is benzyl, and X is bromine.

A process for preparing the compound according to claim 1 of this invention comprises the following steps:

1) dissolving harmine (1) into an organic solvent or a mixed organic solvent;

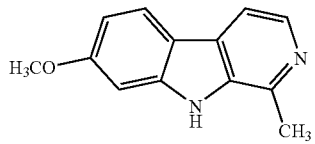

2) adding 60% NaH and stirring it until there is no bubble formed;

3) adding halogenated alkane;

4) stirring and reacting said mixture at room temperature for 1 to 5 h; and 5) subjecting said mixture to conventional post-treatment and purification to produce 1,7,9-trisubstituted β-carboline derivatives.

A process for preparing the compound according to claim 1 of this invention comprises the following steps:

1) dissolving L-tryptophan and NaOH in water;

2) adding formaldehyde;

3) stirring and reacting said mixture at a temperature range from 0° C. to reflux for 1 to 6 h; and 4) subjecting said mixture to conventional post-treatment to produce 1,2,3,4-tetrahydro-β-carboline-3-carboxylic acid (9a).

A process for preparing the compound according to claim 1 of this invention comprises the following steps:

1) dissolving β-carboline-3-carboxylate into an organic solvent or a mixed organic solvent;

2) adding 60% NaH and stirring it until there is no bubble formed;

3) adding halogenated alkane or halogenated aromatic alkane;

4) stirring and reacting said mixture at room temperature, or by heating for 2 to 5 h; and 5) subjecting said mixture to conventional post-treatment and purification to produce 9-substituted-β-carboline-3-carboxylates A process for preparing the compound according to claim 1 of this invention comprises the following steps:

1) dissolving 1-substituted-β-carboline-3-carboxylate into an organic solvent;
2) adding 60% NaH and stirring it for 1 to 10 minutes;
3) adding halogenated alkane or halogenated aromatic alkane;
4) reacting said mixture at room temperature, or refluxing said mixture by heating; and
5) after the reaction is finished, subjecting said mixture to conventional post-treatment and purification to produce ethyl 9-substituted-1-methyl-β-carboline-3-carboxylates.

A process for preparing the compound according to claim 1 of this invention comprises the following steps:

1) mixing compound 10b of the following formula with glacial acetic acid,

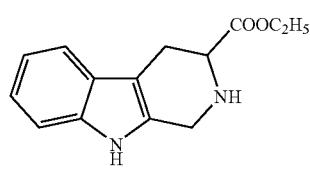

10b 2) adding selenium dioxide;
3) refluxing said mixture by heating for 12 h; and
4) after the reaction is finished, subjecting the mixture to conventional post-treatment and purification to produce β-carboline.

A process for preparing the compound according to claim 1 of this invention comprises the following steps:

1) mixing compound 10 of the following formula with an organic solvent and 60% NaH;

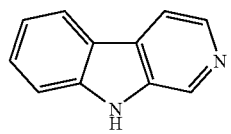

10 wherein $R_1$=H and $R_2$=$C_2H_5$;

2) stirring and reacting said mixture at room temperature for 1 to 10 minutes;
3) adding benzyl iodide;
4) stirring and reacting the mixture at a temperature of from 50 to 70° C. for 1 to 5 h; and
5) subjecting the mixture to conventional post-treatment and purification to produce 2,9-dibenzyl-3-ethoxycarbonyl-β-carbolinium iodate.

A process for preparing the compound according to claim 1 of this invention comprises the following steps:

1) mixing compound 10 of the following formula with an organic solvent and 60% NaH;

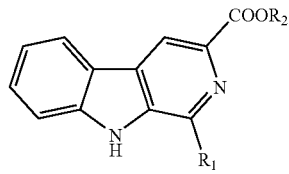

10 wherein $R_1$=H and $R_2$=$C_2H_5$;

2) adding benzyl bromide;
3) stirring and reacting said mixture at a temperature of from 50 to 70° C. for 1 to 10 h; and
5) subjecting the mixture to conventional post-treatment and purification to produce 2,9-dibenzyl-3-ethoxycarbonyl-β-carbolinium bromate.

A process for preparing the compound according to claim 1 of this invention comprises the following steps:

1) mixing compound 80 of the following formula with an organic solvent and 60% NaH;

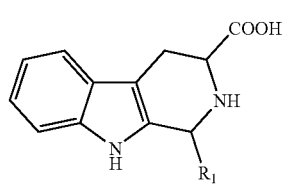

80

2) adding benzyl bromide or benzyl iodide;
3) stirring and reacting said mixture at a temperature of from 50 to 70° C. for 1 to 10 h; and
5) subjecting the mixture to conventional post-treatment and purification to produce 2,9-diphenylmethyl-β-carboline bromide or iodide salts.

This invention also prepares intermediates for the synthesis of the above compounds, i.e. compounds of the following formula (9a-16a):

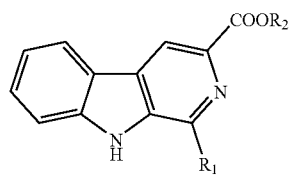

9a-16a wherein
$R_1$ is methyl, ethyl, propyl, isopropyl, n-butyl, unsubstituted or halogenated phenyl, phenylmethyl, or phenylpropyl.

This invention also prepares intermediates for the synthesis of the above compounds, i.e. compounds of the following formula (9b-16b):

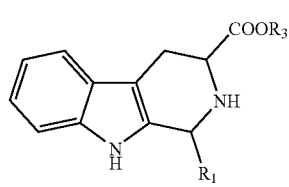

9b-16b wherein
$R_1$ and $R_3$ are the same as $R_1$ in the compounds of formula (9a-16a) as defined above.

This invention also prepares intermediates for the synthesis of the above compounds, i.e. compounds of the following formula (21a):

21a wherein
R₁ is the same as R₁ in the compounds of formula (9a-16a) as defined above.

This invention also prepares intermediates for the synthesis of the above compounds, i.e. compounds of the following formula (53a-55a):

53a-55a wherein
R₉ is methyl, ethyl, n-butyl, phenylmethyl, phenylpropyl, polyhalogenated phenylmethyl or polyhalogenated phenylpropyl.

This invention also prepares intermediates for the synthesis of the above compounds, i.e. compounds of the following formula (10b):

10b wherein
R₁ and R₃ are the same as R₁ in the compounds of formula (9a-16a) as defined above.

Tests on the in vitro anti-tumor activity and studies on the in vivo anti-tumor therapeutic effect of the compounds of this invention showed that the compounds of this invention exhibit enhanced anti-tumor activities and lower neurotoxicities or no neurotoxicities. Moreover, processes for preparing the compounds of this invention are easy and have high yields. The compounds of this invention can be used for the manufacture of a medicament having low toxicity and high efficacy and useful for treating tumors.

It is demonstrated that the compounds of this invention, under UV excitation conditions, have photo induced DNA cleaving effect, which shows the structure-activity relationships between this kind of structure and anti-tumor activity. Therefore the compounds of this invention can also be used for the manufacture of a medicament for treating tumors in combination with phototherapy and radiation therapy.

DESCRIPTION OF THE FIGURES

FIGS. 1A-D illustrate the photocleavage of supercoiled pGBK by β-carboline derivatives: wherein
Lane 1: DNA alone, lane 2: DNA+UV irradiation, lane 3: DNA+compound (1000 uM) without UV irradiation, lanes 4 to 10: DNA+compound+UV irradiation, the concentrations of the compound are respectively 1000, 300, 100, 30, 10, 3 and 1 (uM). Uppermost band: circular nicked DNA, middle band: linear DNA, and lowermost band: supercoiled DNA.

FIGS. 4A-B illustrate the effect of β-carboline derivatives on the activity of DNA topoisomerase I in a cell free system.

Figure 1A:
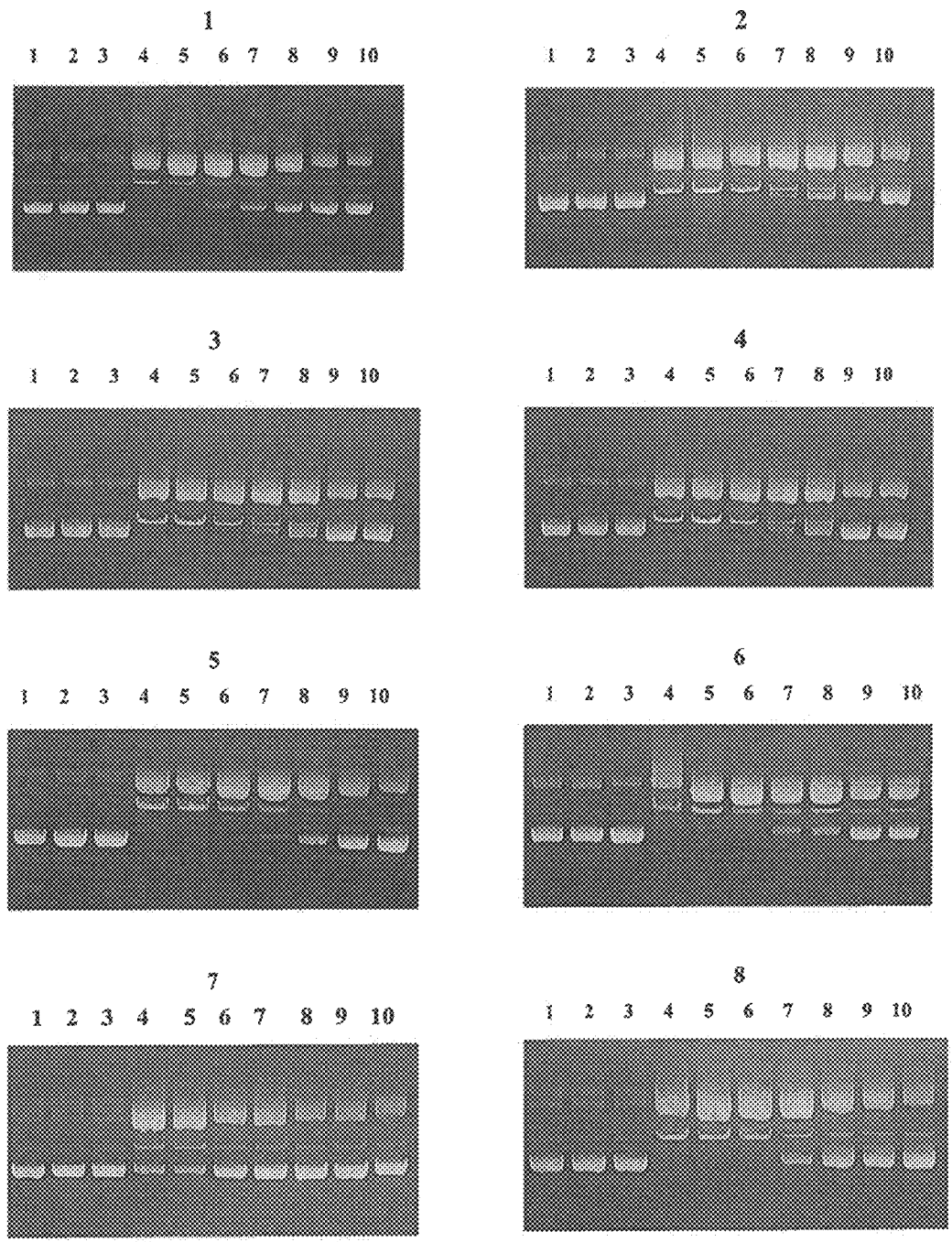
Figure 1C:
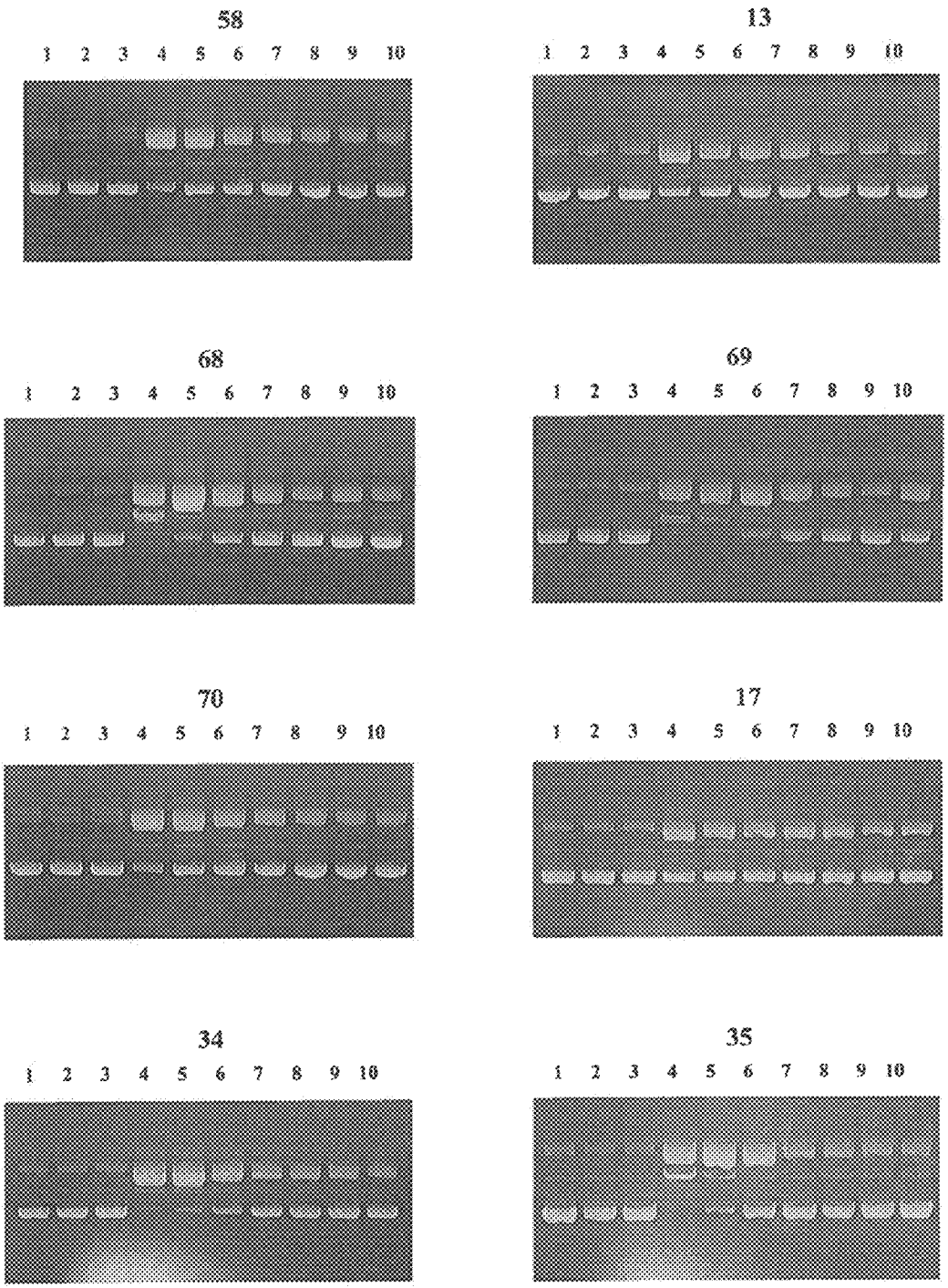
Figure 1D:
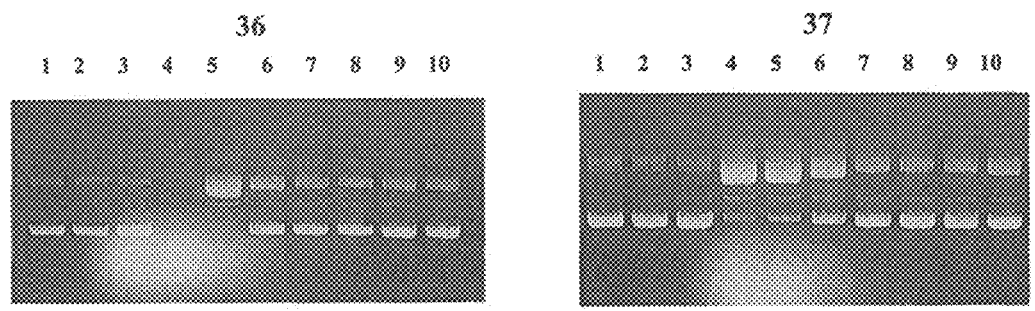

The reaction system (20 ul) containing 35 mM Tris-HCl (pH 7.5), 50 mM KCl, 5 mM MgCl2, 1 mM DTT, 2 mM spermidine, 0.1 mM EDTA, 50 mg·l-1 BSA and 0.25 ug supercoiled pGBK DNA and 1 U topoisomerase I. Lane 1: DNA alone; lane 2: DNA+topoisomerase I, lane 3: DNA+topoisomerase I+250 uM camptothecin, lanes 4 to 9 and 10 to 15, same as lane 2, but with 2000 uM, 600 uM, 200 uM, 60 uM, 20 uM and 6 uM β-carboline derivatives, respectively. A represents compounds 80 and 81. B represents compounds 82 and 83. C represents compounds 37 and 36. D represents compounds 42 and 48. E represents compounds 49 and 66. Form I represents circular nicked DNA. Form II represents linear DNA. Form III represents supercoiled DNA.

Figure 5:
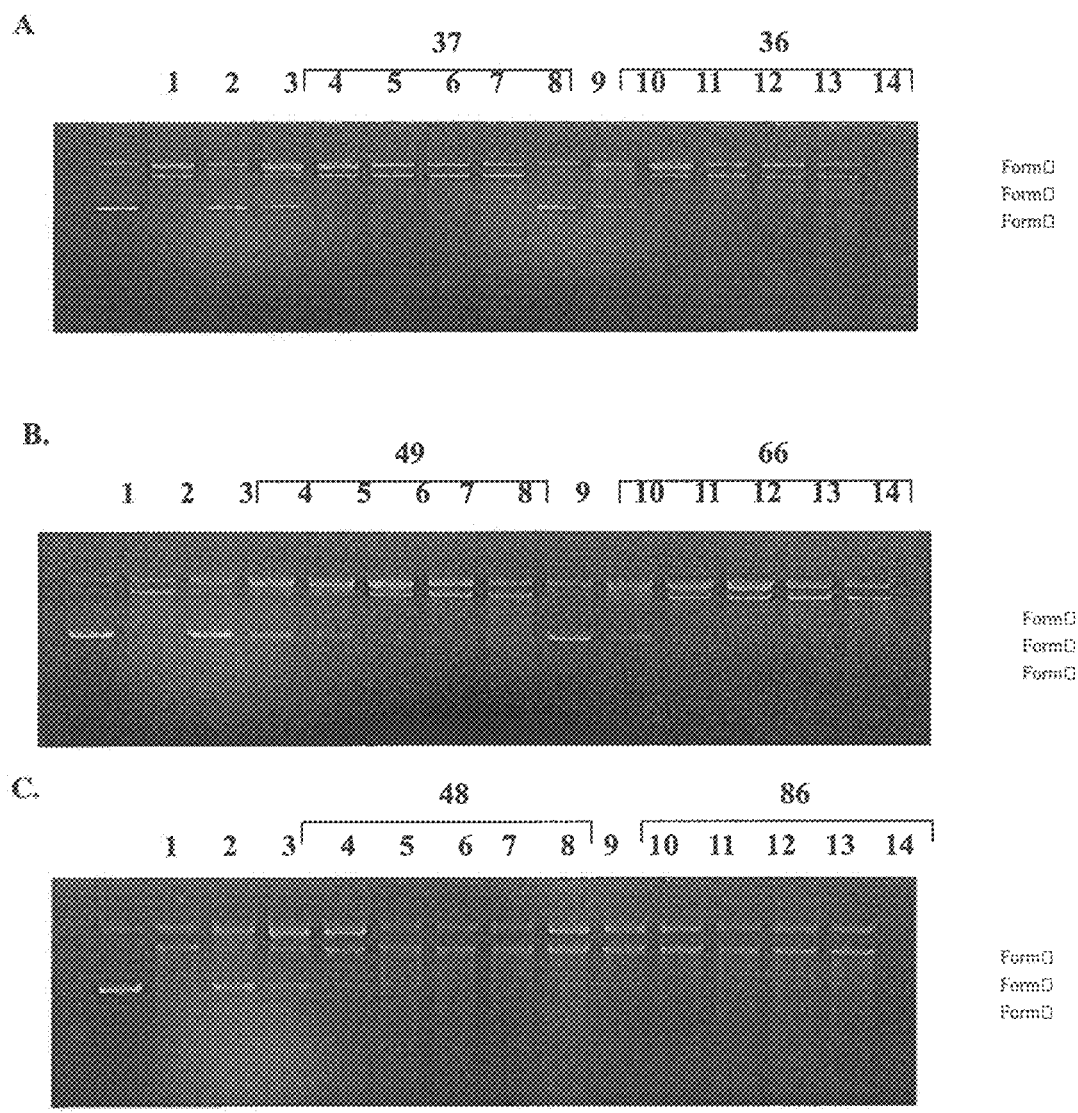

FIG. 5 illustrates the effect of β-carboline derivatives on the activity of DNA topoisomerase II in a cell free system.

The reaction system (20 ul) containing 50 mM Tris-HCl (pH8.0), 120 mM KCl, 10 mM MgCl₂, 1 mM DTT, 0.5 mM ATP, 30 mg·l⁻¹ BSA and 0.25 ug supercoiled pGBK DNA and 1 U topoisomerase II. Lane 1: DNA alone, Lane 2: DNA+topoisomerase II, Lane 3 to 8 and 9 to 14, same as Lane 2, but with 2000 uM, 600 uM, 200 uM, 60 uM, 20 uM and 6 uM β-carboline derivatives. A represents compounds 37 and 36. B represents compounds 49 and 66. C represents compounds 48 and 86. Form I represents circular nicked DNA. Form II represents linear DNA. Form III represents supercoiled DNA.

FIG. 6 illustrates the FCM analysis of apoptosis of HepG2 cells induced by β-carboline derivative (Compound 60).

Figure 7:
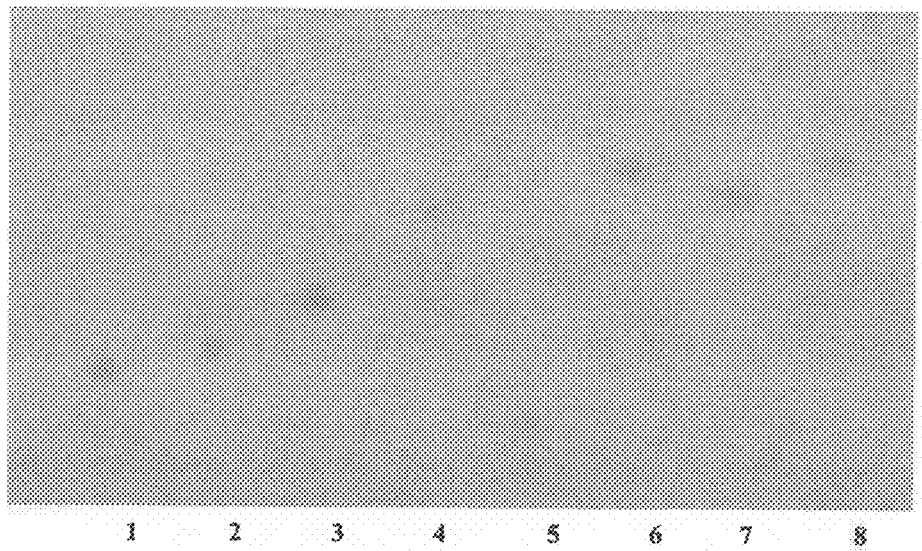

FIG. 7 illustrates the TLC of harmine and 1,7,9-trisubstituted-β-carboline derivatives,
Wherein
Developing solvent: (Ethyl Acetate)
Detection wavelength: UV254 nm
Dots 1 to 8 represent compounds 1 to 8, respectively.

Figure 8:
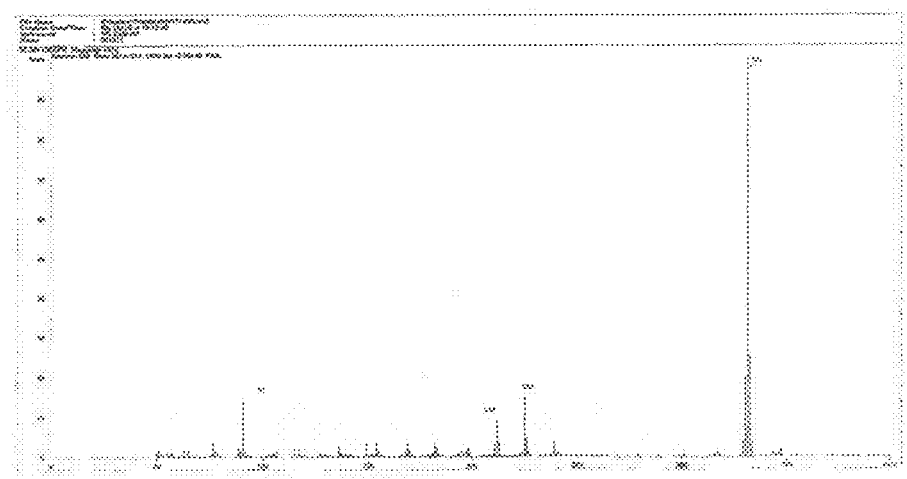

FIG. 8 illustrates the FAB-MS spectrum of 9-phenylpropyl-7-methoxy-1-methyl-β-carboline.

Figure 9:
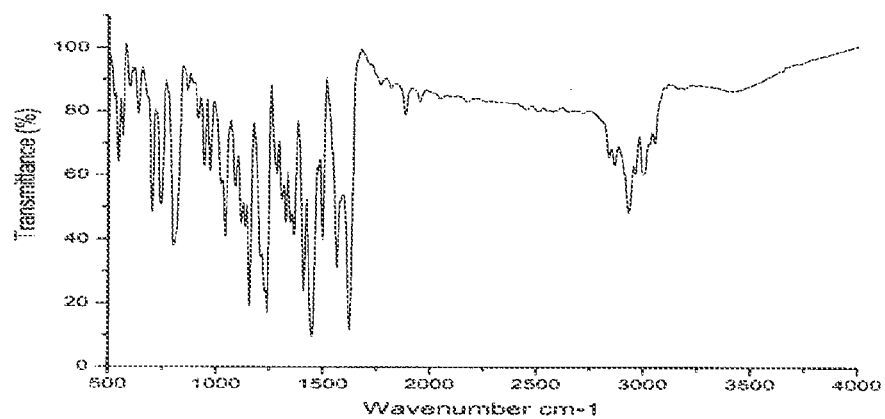

FIG. 9 illustrates the IR spectrum of 9-phenylpropyl-7-methoxy-1-methyl-β-carboline.

Figure 10:
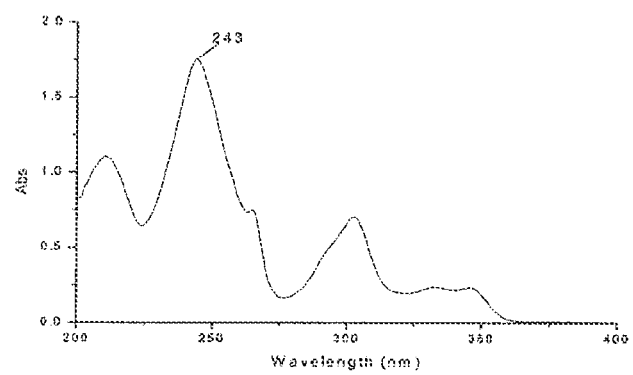

FIG. 10 illustrates the UV spectrum of 9-phenylpropyl-7-methoxy-1-methyl-β-carboline.

Figure 11:
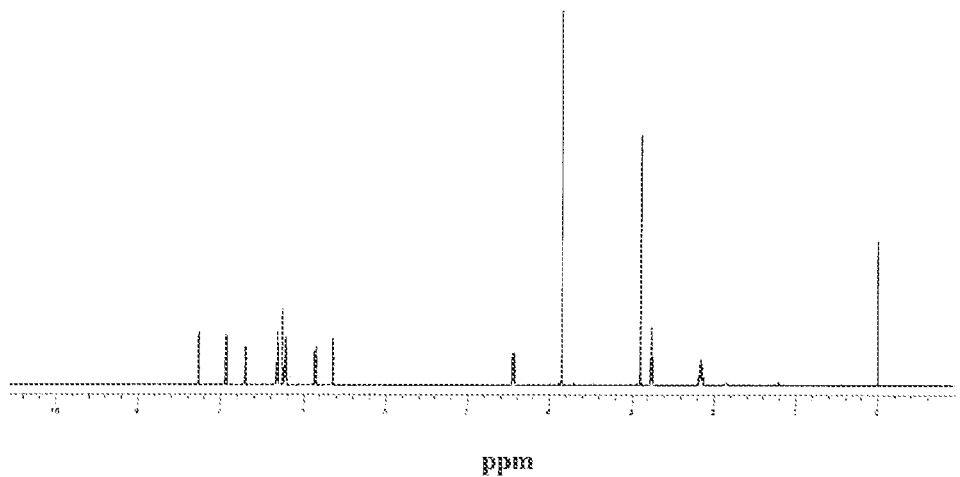

FIG. 11 illustrates the ¹H-NMR spectrum of 9-phenylpropyl-7-methoxy-1-methyl-β-carboline.

Figure 12:
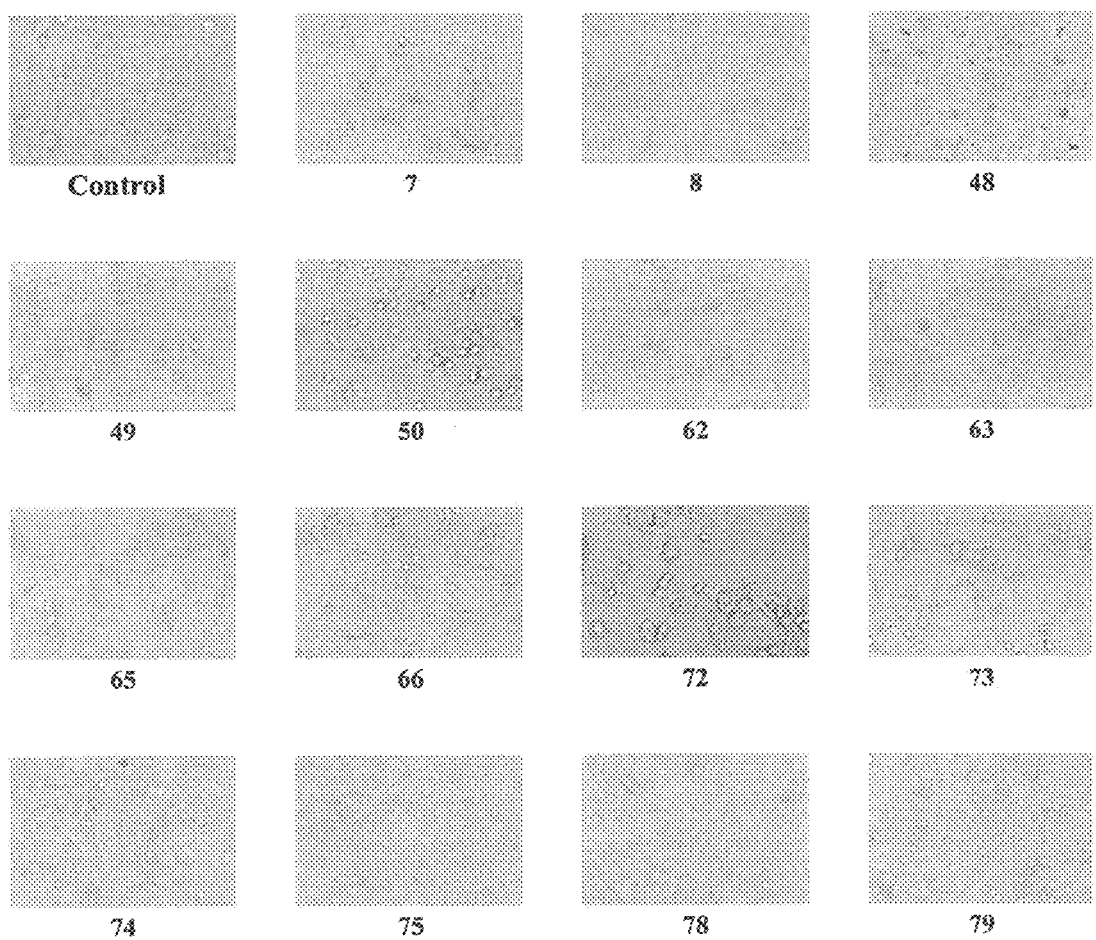

FIG. 12 illustrates the photomicrographs of β-carboline derivatives to human tumor cell HepG2

FIG. 13 illustrates the anti-tumor effect of β-carboline derivatives on Lewis lung cancer.

FIG. 14 illustrates the anti-tumor effect of β-carboline derivatives on S180 sarcoma.

FIGS. 15A-B illustrate the synthetic routes of the research of the modification to the structures of β-carboline derivatives.

SPECIFIC EMBODIMENTS

Description of Examples

Synthesis of 1,7,9-trisubstituted β-carboline derivatives

Experimental Instruments and Reagents
Experimental Instruments:

RE-52C rotary evaporator (Hennan Yuhua Instrument Plant), SHZ-D (III) circulation vacuum water pump (Hennan Yuhua Instrument Plant), UV-8 UV array analysis meter (Wuxi Keda Instrument Plant), YRT-3 melting point apparatus (Precision Instrument Plant, Tianjin University), ZAB-HS double focusing magnetic mass spectrometer (VG Analytical, UK), Bruker Equinox 55 Fourier transform infrared spectrometer, KBr tablet, UV 2501PC UV spectrograph (Shimadzu, Japan), and Varian INOVA500 MRI spectrometer (Varian Inc. U.S.) were used. TMS is the internal standard, and $CDCl_3$ is the solvent.

Chemical Reagents

Harmine 1 having a purity of 99%, provided by Xinjiang Huashidan Pharmaceutical Co. Ltd., methyl iodide (analytically pure, Zhejiang Yuhuan Biochemical Reagent Plant), ethyl iodide (analytically pure, Zhejiang Yuhuan Biochemical Reagent Plant), iodo-n-butane (chemically pure, Shanghai Chemical Reagent Co., China National Pharmaceutical Group), 2-iodoethanol (Acros Organic, U.S.), benzyl bromide (chemically pure, Shanghai Chemical Reagent Co.), 1-bromo-phenylpropane (Acros Organic, U.S.), α-bromo-2,3,4,5,6-pentafluorobenzyl (Acros Organic, U.S.), and other domestically produced analytically pure or chemically pure reagents were used.

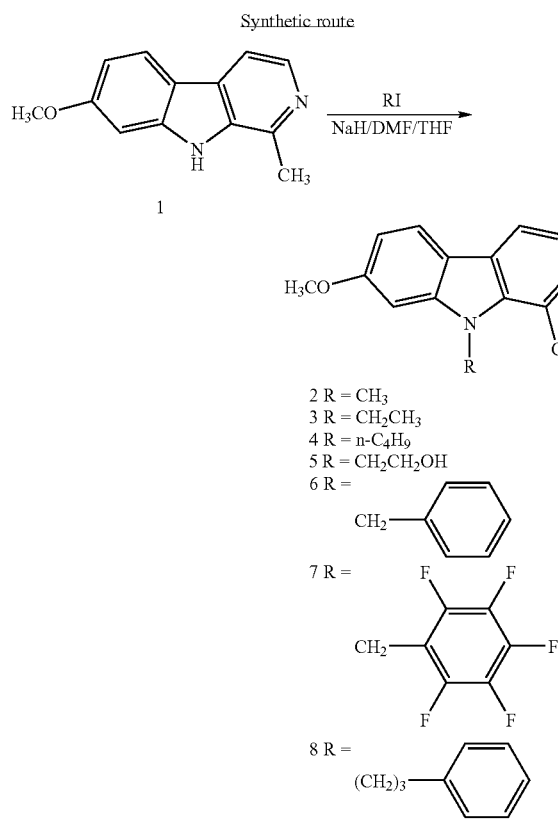

Operation Steps

Example 1

General procedure for the preparation of 1,7,9-trisubstituted β-carboline derivatives Harmine 1 (2.1 g, 10 mmol), DMF (50 ml) and THF (50 ml) were respectively added in a 250 ml round-bottom flask, and stirred at room temperature until the mixture became clear. Then 60% NaH (0.6 g, 15 mmol) was added and stirred until there were no bubbles formed. Alkyl halide (50 mmol) was added dropwise. The mixture was stirred and reacted at room temperature for 5 h. THF was evaporated in reduced pressure, and the residues were poured into cold water. The mixture was adjusted to pH 3 with concentrated hydrochloric acid and extracted with ethyl ether. The aqueous phase was neutralized with saturated $NaHCO_3$ solution and then extracted with ethyl acetate. The organic phase were combined, and washed with water and brine, then dried over anhydrous sodium sulfate, decolorized with activated carbon, filtered and evaporated in reduced pressure. The residue obtained was purified by silica gel column chromatography with ethyl acetate as the eluent. Upon recrystallization, crystals were obtained. Examples 2 to 5 were all treated according to the above procedures.

Example 2

Synthesis of 7-methoxyl-1,9-dimethyl-β-carboline (2)

Afforded gray needle crystals (1.8 g, 80%), mp 121-123° C.

Example 3

Synthesis of 7-methoxyl-9-ethyl-1-methyl-β-carboline (3)

Afforded gray needle crystals (2.0 g, 80%), mp 99-101° C.

Example 4

Synthesis of 7-methoxyl-9-n-butyl-1-methyl-β-carboline (4)

Afforded gray needle crystals (2.1 g, 78%), mp 104-105° C.

Example 5

Synthesis of 9-hydroxyethyl-7-methoxy-1-methyl-β-carboline (5)

Afforded white crystals (0.7 g, 54%), mp 204-206° C.

Example 6

Synthesis of 9-benzyl-7-methoxy-1-methyl-β-carboline (6)

Harmine 1 (2.1 g, 10 mmol), DMF (50 ml) and THF (50 ml) were respectively added in a 250 ml round-bottom flask, and were stirred at room temperature for 10 minutes followed by the addition of 60% NaH (1.2 g, 30 mmol). The mixture was stirred until there were no bubbles formed. Benzyl bromide (3 ml) was added dropwise. The mixture was then refluxed by heating for 8 h. THF was evaporated in reduced pressure, and the residues were poured into cold water. The mixture was adjusted to pH 3.0 with concentrated HCl, and extracted with ethyl ether. The aqueous phase was neutralized (pH8) with saturated $NaHCO_3$ solution and extracted with ethyl acetate. The organic phases were combined, washed with water and brine, dried over anhydrous sodium sulfate, filtered, evaporated in reduced pressure and then recrystallized with ethyl acetate to afford gray crystals (2.2 g, 67%). mp 131-133° C.

Example 7

Synthesis of 9-(2',3',4',5',6'-pentafluoro)benzyl-7-methoxy-1-methyl-β-carboline (7)

Harmine 1 (0.53 g, 2.5 mmol), 15 ml of DMF and 15 ml of THF were respectively added in a 100 ml round-bottom flask, and were stirred at room temperature until the mixture became clear. 60% NaH (0.3 g, 7.5 mmol) was added and stirred until there were no bubbles formed. α-Bromo-2,3,4,5,6-pentafluorobenzyl (0.5 ml) was added dropwise. The mixture was stirred and reacted at room temperature for 1 hour. Later the mixture was treated in a manner to that described for compound 2 to afford gray needle crystals (0.64 g, 65%), mp 173-174° C.

Example 8

Synthesis of 9-phenylpropyl-7-methoxy-1-methyl-β-carboline (8)

Harmine 1 (0.53 g, 2.5 mmol), DMF (15 ml) and THF (15 ml) were respectively added in a 100 ml round-bottom flask, and stirred at room temperature until the mixture became clear, then 60% NaH (0.3 g, 7.5 mol) was added and stirred until there were no bubbles formed. 1-Brombenzenepropropane (2 ml) was added dropwise. The mixture was refluxed for 12 h. THF was evaporated in reduced pressure. The residues were poured into 30 ml cold water and extracted with ethyl acetate. The organic phases were combined, and washed with water and brine, dried over anhydrous sodium sulfate, filtered, evaporated in reduced pressure, and the residue dissolved in 50 anhydrous ethanol. The pH was adjusted to 4 with concentrated HCl, the mixture were concentrated in vacuum and then recrystallized with acetone to afford yellow solids. The solids were dissolved into a mixed solution of water and ethyl acetate. The pH was adjusted to 8 with saturated $NaHCO_3$ solution. The organic layer was isolated, and the aqueous phase was extracted with ethyl acetate. The organic phases were combined, washed with water and brine, dried over anhydrous sodium sulfate, decolorized with activated carbon, filtered, concentrated, and recrystallized with ethyl ether to afford gray needle crystals (0.42 g, 51%), mp 117-118° C.

Physico-chemical constants, TLC and spectra analyses of 1,7,9-substituted β-carboline derivatives

TABLE 6

Physico-chemical data of 1,7,9-substituted β-carboline derivatives

| Compd | Formula | FW | Yield (%) | Appearance | Solubility | Mp (° C.) |
|---|---|---|---|---|---|---|
| 1 | $C_{13}H_{12}N_2O$ | 212 | — | gray needle crystal | Soluble in organic solvents, such as alcohol, ether, and ester, and water-insoluble | 260-261 |
| 2 | $C_{14}H_{14}N_2O$ | 226 | 80 | gray needle crystal | Soluble in organic solvents, such as alcohol, ether, and ester, and water-insoluble | 121-123 |
| 3 | $C_{15}H_{16}N_2O$ | 240 | 83 | gray needle crystal | Soluble in organic solvents, such as alcohol, ether, and ester, and water-insoluble | 99-101 |
| 4 | $C_{17}H_{20}N_2O$ | 268 | 78 | gray needle crystal | Soluble in organic solvents, such as alcohol, ether, and ester, and water-insoluble | 104-105 |
| 5 | $C_{15}H_{16}N_2O_2$ | 256 | 62 | white crystal | Soluble in organic solvents, such as alcohol, ether, and ester, and water-insoluble | 204-206 |
| 6 | $C_{20}H_{18}N_2O$ | 302 | 54 | gray needle crystal | Soluble in organic solvents, such as alcohol, ether, and ester, and water-insoluble | 131-133 |
| 7 | $C_{15}H_{11}F_5N_2O$ | 392 | 65 | gray needle crystal | Soluble in organic solvents, such as alcohol, ether, and ester, and water-insoluble | 173-174 |

TABLE 6-continued

Physico-chemical data of 1,7,9-substituted β-carboline derivatives

| Compd | Formula | FW | Yield (%) | Appearance | Solubility | Mp (° C.) |
|---|---|---|---|---|---|---|
| 8 | $C_{20}H_{22}N_2O$ | 330 | 51 | gray needle crystal | Soluble in organic solvents, such as alcohol, ether, and ester, and water-insoluble | 117-118 |

TABLE 7

FAB-MS, IR and UV data of 1,7,9-substituted β-carboline derivatives

| Compd | Formula | FAB-MS m/e (M + 1) | IR (KBr, cm$^{-1}$) | UV ($\lambda_{max}$, nm) |
|---|---|---|---|---|
| 1 | $C_{13}H_{12}N_2O$ | 213 | ND | ND |
| 2 | $C_{14}H_{14}N_2O$ | 227 | 3451, 3380, 2744, 1628, 1570, 1469, 1348, 1249, 1152, 1045, 810 | 345, 332, 302, 264, 244, 213 |
| 3 | $C_{15}H_{16}N_2O$ | 241 | 3362, 3128, 1622, 1564, 1497, 1451, 1346, 1262, 1217, 1136, 1095, 812 | 344, 332, 302, 264, 243, 213 |
| 4 | $C_{17}H_{20}N_2O$ | 269 | 3428, 2959, 2927, 2863, 1884, 1621, 1563, 1497, 1448, 1356, 1242, 1197, 1137, 812 | 346, 333, 302, 265, 244, 213 |
| 5 | $C_{15}H_{16}N_2O_2$ | 257 | 3294, 2696, 1629, 1569, 1467, 1352, 1155, 1051, 810 | 327, 304, 248, 210 |
| 6 | $C_{20}H_{18}N_2O$ | 303 | 3421, 2958, 1620, 1565, 1498, 1447, 1404, 1361, 1256, 1197, 1172, 1044, 825 | 396, 342, 330, 301, 244, 209 |
| 7 | $C_{15}H_{11}F_5N_2O$ | 393 | 2961, 2836, 1622, 1502, 1446, 1256, 1174, 1122, 1026, 974 816 | 337, 325, 300, 240, 208 |
| 8 | $C_{20}H_{22}N_2O$ | 330 | 3052, 2995, 2931, 2666, 1881, 1623, 1563, 1449, 1408, 1238, 1156, 1043, 801, 744, 702 | 345, 332, 302, 265, 244, 210 |

TABLE 8

$^1$H-NMR data of 1,7,9-substituted β-carboline derivatives

| Compd | $^1$H-NMR (δ, CDCl$_3$) |
|---|---|
| 2 | 8.24-8.25 (1H, m, H-5), 7.93-7.96 (1H, m, H-3), 7.69-7.71 (1H, m, H-4), 6.86-6.89 (1H, m, H-8), 6.81-6.83 (1H, m, H-6), 4.04-4.07 (3H, m, NCH$_3$,), 3.94-3.95 (3H, m, OCH$_3$), 3.04-3.05 (3H, m, Ar—CH$_3$) |
| 3 | 8.26-8.27 (1H, d, J = 5 Hz, H-5), 7.96-7.98 (1H, d, J = 5 Hz, H-3), 7.74-7.75 (1H, d, J = 4.5 Hz, H-4), 6.86-6.90 (2H, m, H-8, H-6), 4.52-4.57 (2H, m, CH$_2$CH$_3$), 3.95 (3H, s, OCH$_3$), 3.05 (3H, s, CH$_3$), 1.43-1.46 (3H, m, CH$_2$CH$_3$) |
| 4 | 8.26-8.28 (1H, d, J = 5.5 Hz, H-5), 7.95-7.97 (1H, d, J = 9 Hz, H-3), 7.71-7.72 (1H, d, J = 5 Hz, H-4), 6.85-6.88 (2H, m, H-8, H-6), 4.43-4.46 (2H, m, J = 8 Hz, CH$_2$CH$_2$CH$_2$CH$_3$), 3.94 (3H, s, OCH$_3$), 3.01 (3H, s, Ar—CH3), 1.78-1.84 (2H, m, CH$_2$CH$_2$CH$_2$CH$_3$), 1.41-1.48 (2H, m, CH$_2$CH$_2$CH$_2$CH$_3$), 0.97-1.00 (3H, m, CH$_2$CH$_2$CH$_3$) |
| 5 | 8.15-8.16 (1H, d, J = 4 Hz, H-5), 7.93-7.94 (1H, d, J = 3.5 Hz, H-3), 7.63-7.64 (1H, d, J = 5 Hz, H-4), 6.88-6.95 (2H, m, H-8, H-6), 4.66-4.71 (2H, m, NCH$_2$CH$_2$OH), 4.06-4.08 (2H, m, NCH$_2$CH$_2$OH), 3.94 (3H, s, OCH$_3$), 2.99 (3H, s, CH$_3$) |
| 6 | 8.29-8.30 (1H, d, J = 5.5 Hz, H-5), 8.01-8.02 (1H, d, J = 8.5 Hz, H-3), 7.80-7.81 (1H, d, J = 5.5 Hz, H-4), 7.23-7.30 (3H, m, H-8, H-6, Ar—H), 6.98-7.00 (1H, d, J = 7.0 Hz, Ar—H), 6.90-6.92 (1H, m, Ar—H), 6.76 (1H, s, Ar—H), 5.75 (2H, s, NCH$_2$Ar), 3.85 (3H, s, OCH$_3$), 2.88 (3H, s, CH$_3$) |
| 7 | 8.32-8.33 (1H, d, J = 5 Hz, H-5), 7.94-7.95 (1H, d, J = 7.5 Hz, H-3), 7.72-7.73 (1H, d, J = 7.5 Hz, H-4), 7.26 (1H, s, H-8), 6.87-6.89 (1H, m, H-6), 5.85 (2H, s, CH$_2$Ar), 3.88 (3H, s, OCH$_3$), 3.05 (3H, s, Ar—CH$_3$) |
| 8 | 8.25-8.26 (1H, d, J = 5 Hz, H-5), 7.92-7.94 (1H, d, J = 8.5 Hz, H-3), 7.69-7.70 (1H, d, J = 5.0 Hz, H-4), 7.29-7.32 (2H, m, H-8, H-6), 7.20-7.25 (3H, m, Ar—H), 6.84-6.86 (1H, m, Ar—H), 6.63-6.64 (1H, m, Ar—H), 4.42-4.45 (2H, m, NCH$_2$CH$_2$CH$_2$Ar), 3.84-3.85 (3H,, OCH$_3$), 2.88 (3H, s, CH$_3$), 2.74-2.77 (2H, m, NCH$_2$CH$_2$CH$_2$Ar), 2.12-2.18 (2H, m, NCH$_2$CH$_2$CH$_2$Ar) |

Spectra Analyses of Typical Compounds

See FIGS. 8 to 11 for the spectrum analyses of compound 8.

Synthesis of 3- and 1,3-disubstituted β-carboline alkaloids

Experimental Instruments and Reagents

Experimental instruments are as defined above.

Chemical Reagents

L-tryptophan (Acros Organic, U.S.), formaldehyde solution (analytically pure, Guangzhou Chemical Reagent Plant), 40% acetaldehyde (analytically pure, Shanghai Chemical Reagent Co., China National Pharmaceutical Group), propionaldehyde (chemically pure, Shanghai Chemical Reagent Co., China National Pharmaceutical Group), n-butyraldehyde (analytically pure, Shanghai Chemical Reagent Co., China National Pharmaceutical Group), benzaldehyde (analytically pure, Guangzhou Chemical Reagent Plant), 4-methoxy benzaldehyde (analytically pure, Shanghai Chemical Reagent Co., China National Pharmaceutical Group) and p-hydroxy benzaldehyde (analytically pure, Shanghai Shuangxi Flavor Adjuvant Plant), and domestically manufactured analytically pure or chemically pure reagents were used.

Synthetic Routes and Operational Steps

Scheme I

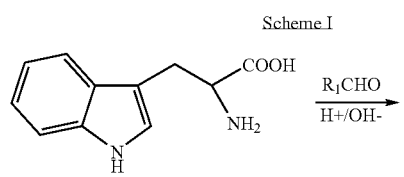

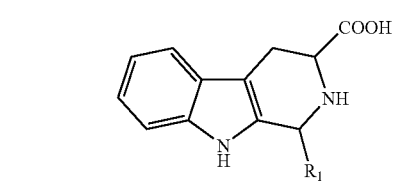

9a $R_1 = H$
11a $R_1 = CH_3$
12a $R_1 = CH_2CH_3$
13a $R_1 = CH_2CH_2CH_3$

14a $R_1 = $ —⟨phenyl⟩

15a $R_1 = $ —⟨C$_6$H$_4$⟩—OCH$_3$

16a $R_1 = $ —⟨C$_6$H$_4$⟩—OH

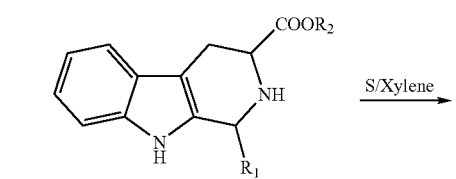

9b $R_1 = H$  $R_2 = CH_3$
10b $R_1 = H$  $R_2 = CH_2CH_3$
11b $R_1 = CH_3$  $R_2 = CH_2CH_3$
12b $R_1 = CH_2CH_3$  $R_2 = CH_2CH_3$
13b $R_1 = CH_2CH_2CH_3$  $R_2 = CH_2CH_3$

14b $R_1 = $ —⟨phenyl⟩  $R_2 = CH_3$

15b $R_1 = $ —⟨C$_6$H$_4$⟩—OCH$_3$  $R_2 = CH_3$

16b $R_1 = $ —⟨C$_6$H$_4$⟩—OH  $R_2 = CH_3$

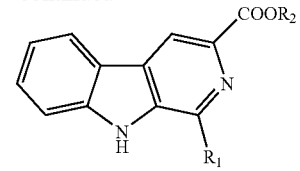

9 $R_1 = H$  $R_2 = CH_3$
10 $R_1 = H$  $R_2 = CH_2CH_3$
11 $R_1 = CH_3$  $R_2 = CH_2CH_3$
12 $R_1 = CH_2CH_3$  $R_2 = CH_2CH_3$
13 $R_1 = CH_2CH_2CH_3$  $R_2 = CH_2CH_3$

14 $R_1 = $ —⟨phenyl⟩  $R_2 = CH_3$

15 $R_1 = $ —⟨C$_6$H$_4$⟩—OCH$_3$  $R_2 = CH_3$

16 $R_1 = $ —⟨C$_6$H$_4$⟩—OH  $R_2 = CH_3$

Example 9

Synthesis of 1,2,3,4-tetrahydro-β-carboline-3-carboxylic acid (9a)

L-tryptophan (10.2 g, 50 mmol), NaOH (2.0 g, 50 mmol) and H$_2$O (20 ml) were added in a 250 ml round-bottom flask, and were stirred until the mixture became clear followed by the addition of formaldehyde (37%, 50 mmol). The mixture was stirred and reacted at room temperature for 3 h. After being refluxed for another 3 h, the mixture was poured into 200 ml cold water. While being stirred, the mixture was adjusted to pH 6 with 5N HCl. White solids were precipitated and then stored at 4° C. overnight. The white solids were filtered, washed well with water and a small amount of methanol, dried, and recrystallized with methanol to obtain white solids (9.2 g, 85%), mp 308-309° C. (reference: 309-310° C.).

Example 10

General procedure for the preparation of 1,2,3,4-tetrahydro-β-carboline-3-carboxylates 1,2,3,4-Tetrahydro-β-carboline-3-carboxylic acid 9a (50 mmol), methanol or ethanol (250 ml) and thionyl chloride (10 ml) were added into a 500 ml round-bottom flask. The mixture was refluxed for 1 to 2 h. After alcohol was evaporated in reduced pressure, 100 ml cold water was added. The pH was adjusted to 9 with saturated NaHCO$_3$ solution. Then the mixture was extracted with ethyl acetate. The organic phases were combined, washed with water and brine, dried over anhydrous sodium sulfate, filtered, concentrated in vacuum. Recrystallization was conducted with ethyl acetate. Examples 11 and 12 were treated according to the above procedures.

Example 11

Synthesis of methyl 1,2,3,4-tetrahydro-β-carboline-3-carboxylate (9b)

white solids were obtained, and the yield was 57%.

Example 12

Synthesis of ethyl 1,2,3,4-tetrahydro-β-carboline-3-carboxylate (10b)

white needle crystals were obtained, and the yield was 63%.

Example 13

General procedure for the preparation of β-carboline-3-carboxylates

Compound 9b-10b (50 mmol), anhydrous xylene (200 ml) and sulfur (200 mmol) were added into a 100 ml round-bottom flask. The mixture was refluxed for 12 h and then cooled to room temperature. The mixture was stored at 4° C. overnight to precipitate light yellow crystals. After filtration and wash with a small amount of cold xylene and wash liberally with petroleum ether, the solids were dissolved into 2000 ml of a corresponding alcohol. The solids were decolorized with activated carbon and filtered with 200 to 300 meshes silica gel. The filtrate was concentrated in vacuum and recrystallized with a corresponding alcohol. Examples 14 and 15 were treated according to the above procedures.

Example 14

Synthesis of methyl β-carboline-3-carboxylate (9)

white solids were obtained, the yield was 66%, mp 308-309° C.

Example 15

Synthesis of ethyl β-carboline-3-carboxylate (10)

white solids were obtained, the yield was 77%, mp 230-231° C. (reference[1]: 231-232° C.).

Example 16

Synthesis of 1-methyl-1,2,3,4-tetrahydro-β-carboline-3-carboxylic acid (11a)

L-tryptophan (5.10 g, 25 mmol), $H_2SO_4$ (0.01 M, 30 ml) and 40% acetaldehyde (9 ml) were added in a 250 ml round-bottom flask, and then stirred and reacted at room temperature for 8 h. After filtration, wash with water and drying, white solids (4.0 g, 69%) were obtained.

Example 17

Synthesis of 1-ethyl-1,2,3,4-tetrahydro-β-carboline-3-carboxylic acid (12a)

L-tryptophan (5.10 g, 25 mmol), water (300 ml), $H_2SO_4$ (0.05M, 30 ml) and propionaldehyde (8 ml) were added in a 250 ml round-bottom flask, and then stirred and reacted at room temperature for 24 h. After filtration, wash with water and drying, white solids (4.5 g, 74%) were obtained.

Example 18

Synthesis of 1-propyl-1,2,3,4-tetrahydro-β-carboline-3-carboxylic acid (13a)

L-tryptophan (5.10 g, 25 mmol), water (300 ml), $H_2SO_4$ (0.5M, 50 ml), n-butyraldehyde (10 ml) and ethanol (100 ml) were added in a 250 ml round-bottom flask, and then stirred and reacted at room temperature for 24 h. After filtration, wash with water and drying, white solids (3.75 g, 58%) were obtained.

Example 19

General procedure for the preparation of ethyl 1-alkyl-1,2,3,4-tetra-hydro-β-carboline-3-carboxylates 1-Alkyl-1,2,3,4-tetrahydro-β-carboline-3-carboxylic acid 11a-13a (20 mmol), and anhydrous ethanol (250 ml) were added in a 250 ml round-bottom flask. Redistilled thionyl chloride (6 ml) was carefully added. The mixture was refluxed for 1 h. Ethanol was then evaporated in reduced pressure to afford white solids. The white solids were dissolved in 100 ml water. Saturated $NaHCO_3$ was used to conduct neutralization. Extraction was conducted with ethyl acetate. Organic phases were combined, washed with water and brine, dried with anhydrous sodium sulfate, decolorized with activated carbon, filtered, concentrated in vacuum and recrystallized with ethyl acetate. Examples 20 to 22 were treated according to the above procedures.

Example 20

Synthesis of ethyl 1-methyl-1,2,3,4-tetrahydro-β-carboline-3-carboxylate (11b)

white solids were obtained, and the yield was 71%.

Example 21

Synthesis of ethyl 1-ethyl-1,2,3,4-tetrahydro-β-carboline-3-carboxylate (12b)

white solids was obtained, and the yield was 52%.

Example 22

Synthesis of ethyl 1-propyl-1,2,3,4-tetrahydro-β-carboline-3-carboxylate (13b)

white solids were obtained, and the yield was 84%.

Example 23

General procedure for the preparation of ethyl 1-alkyl-β-carboline-3-carboxylates Ethyl 1-alkyl-1,2,3,4-tetrahydro-β-carboline-3-carboxylate 11b-13b (20 mmol), sulfur (60 mmol) and xylene (200 ml) were added into a 500 ml round-bottom flask and then refluxed for 10 h. The mixture was then cooled to room temperature. After being stored at 4° C. overnight, light yellow solids were precipitated. After filtration and wash with a small amount of cold xylene and wash well with petroleum ether, the solids were dissolved into 2000 ml of anhydrous ethanol. The solids were decolorized with activated carbon and filtered with 200 to 300 meshes silica gel. The filtrate was concentrated in vacuum and recrystallized with ethyl acetate. Examples 24 to 26 were conducted according to the above operation steps.

Example 24

Synthesis of ethyl 1-methyl-β-carboline-3-carboxylate (11)

white solids were obtained, the yield was 48%, and mp 217-218° C.

Example 25

Synthesis of ethyl 1-ethyl-β-carboline-3-carboxylate (12)

white solids were obtained, the yield was 47%, and mp 209-210° C.

Example 26

Synthesis of ethyl 1-propyl-β-carboline-3-carboxylate (13)

white solids were obtained, the yield was 58%, and mp 194-195° C.

Example 27

General procedure for the preparation of 1-aryl-1,2,3,4-tetrahydro-β-carboline-3-carboxylic acids L-tryptophan (50 mmol), a corresponding aromatic aldehyde (55 mmol), $H_2SO_4$ (0.5M, 50 ml), $H_2O$ (150 ml) and ethanol (100 ml) were added in a 550 ml round-bottom flask, and then refluxed for 5 h. After adding concentrated ammonia (100 ml), the mixture was refluxed for another hour. Ethanol was evaporated. The resulting solution was cooled and extracted with ethyl ether. The aqueous phase was concentrated to 50 ml and was adjusted to pH 5, and the precipitate were then filtered, washed well with water and dried. Examples 28 to 30 were conducted according to the above operational steps.

Example 28

Synthesis of 1-phenyl-1,2,3,4-tetrahydro-β-carboline-3-carboxylic acid (14a)

white solids were obtained, and the yield was 98%.

Example 29

Synthesis of 1-(4-methoxyphenyl)-1,2,3,4-tetrahydro-β-carboline-3-carboxylic acid (15a)

white solids were obtained, and the yield was 82%.

Example 30

Synthesis of 1-(4-hydroxyphenyl)-1,2,3,4-tetrahydro-β-carboline-3-carboxylic acid (16a)

light yellow solids were obtained, and the yield was 94%.

Example 31

General procedure for the preparation of 1-aryl-1,2,3,4-tetrahydro-β-carboline-3-carboxylates 1-Aryl-1,2,3,4-tetrahydro-β-carboline-3-carboxylic acid 14a-16a (50 mmol) and methanol (250 ml) were respectively added into a 500 ml round-bottom flask. Redistilled thionyl chloride (20 ml) was carefully added. The mixture was refluxed for 2 h. Methanol was evaporated in reduce pressure. After filtration and wash with a small amount of acetone, ash gray solids were obtained. The solids were dissolved in 300 ml cold water and adjusted to pH 9. The mixture was extracted with ethyl acetate. After wash with water and brine, the organic phase was dried over anhydrous sodium sulfate and then recrystallized with ethyl acetate. Examples 32 to 34 were treated according to the above procedures.

Example 32

Methyl 1-phenyl-1,2,3,4-tetrahydro-β-carboline-3-carboxylate (14b)

white solids were obtained, and the yield was 95%.

Example 33

Methyl 1-(4-methoxyphenyl)-1,2,3,4-tetrahydro-β-carboline-3-carboxylate (15b)

white solids were obtained, and the yield was 90%.

Example 34

Methyl 1-(4-hydroxyphenyl)-1,2,3,4-tetrahydro-β-carboline-3-carboxylate (16b)

white solids were obtained, and the yield was 85%.

Example 35

General procedure for the preparation of methyl 1-aryl-β-carboline-3-carboxylates Methyl 1-aryl-1,2,3,4-tetrahydro-β-carboline-3-carboxylate 14b-16b (20 mmol), sulfur (60 mmol), and xylene (200 ml) were respectively added into a 500 ml round-bottom flask. The mixture was refluxed for 18 h and then cooled to room temperature. After being stored at 4° C. overnight, light yellow solids were precipitated. After filtration and wash with a small amount of cold xylene and wash well with petroleum ether, the solids were dissolved into 1000 ml of ethyl acetate, decolorized with activated carbon and filtered with 200 to 300 meshes silica gel. The filtrate was concentrated in vacuum and recrystallized with ethyl acetate. Examples 36 to 38 were conducted according to the above operation steps.

Example 36

Synthesis of methyl 1-phenyl-β-carboline-3-carboxylate (14)

white solids were obtained, the yield was 69%, and mp 257-258° C.

Example 37

Synthesis of methyl 1-(4-methoxyphenyl)-β-carboline-3-carboxylate (15)

white solids were obtained, the yield was 63%, and mp 229-230° C.

Example 38

Synthesis of methyl 1-(4-hydroxyphenyl)-β-carboline-3-carboxylate (16)

white solids were obtained, the yield was 56%, and mp 267-269° C.

Example 39

Synthesis of β-carboline-3-carboxylic acid (17)

Compound 10 (1.2 g, 5 mmol), NaOH (0.8 g, 20 mmol), ethanol (20 ml) and H₂O (40 ml) were added into a 50 ml round-bottom flask. The mixture was refluxed for 2 h. Ethanol was then evaporated in reduced pressure. The mixture was adjusted to pH with 5M HCl. After cooling with cold water, filtration, wash well with water and recrystallization with ethanol, white solids (0.96 g, 90%) were obtained. and mp 307-309° C. (reference[1]: 310° C.).

Example 40

Synthesis of butyl β-carboline-3-carboxylate (18)

Compound 17 (2.1 g, 10 mmol), NaOH (0.8 g, 20 mmol), n-butanol (100 ml) and thionyl chloride (5 ml) were added into a 250 ml round-bottom flask. The mixture was refluxed for 6 h. Excessive n-butanol was then removed in reduced pressure. The residues were dissolved in water followed by the addition of ethyl acetate. While being stirred, the mixture was adjusted to pH 8 with NaHCO₃ solution. The organic layer was isolated. The aqueous phase was extracted with ethyl acetate. The organic phases were combined, washed with water and brine, dried over anhydrous sodium sulfate, decolorized with activated carbon and concentrated in vacuum. The residues were dissolved in ethyl acetate, and purified by silica gel column chromatography with ethyl acetate as the eluent, the recrystallized with ethyl ether/petroleum ether (2:5) to afford white needle crystals (1.8 g, 67%), and mp 211-212° C. (reference [1]: 210-211° C.).

Example 41

Synthesis of 3-ethylamino-β-carboline-3-formamide (19)

Ethylenediamine (24 ml, 27 mmol) was added into a dry 250 ml three-neck round-bottom flask and heated to 80-90° C.

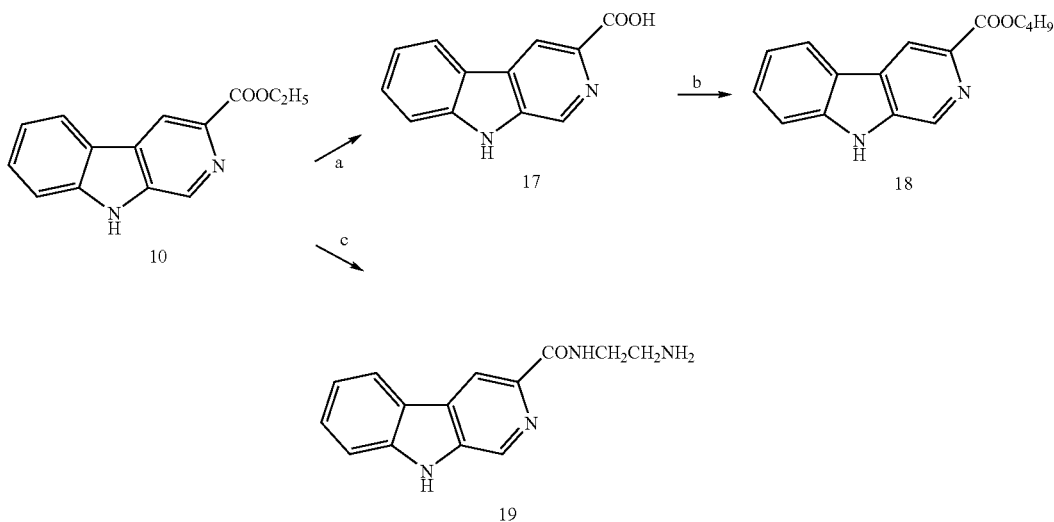

a) NaOH, EtOH; HCl
b) SOCl₂, n-BuOH;
c) CHCl₃, MeOH

While the mixture was stirred, compound 10 (2.4 g, 10 mmol) was added dropwise and dissolved in a solution of 40 ml chloroform and 30 ml methanol for about 1 h. The mixture was refluxed for 10 h, and the solvent was evaporated. A mixed solution of 50 ml chloroform and 20 ml water was added into the residues. After being stored at 4° C. overnight, light yellow solids were precipitated. After filtration and drying, white needle crystals (0.85 g, 30%) were obtained. and mp 233-236° C. (reference[1], 234-237° C., 25%).

Synthetic route III

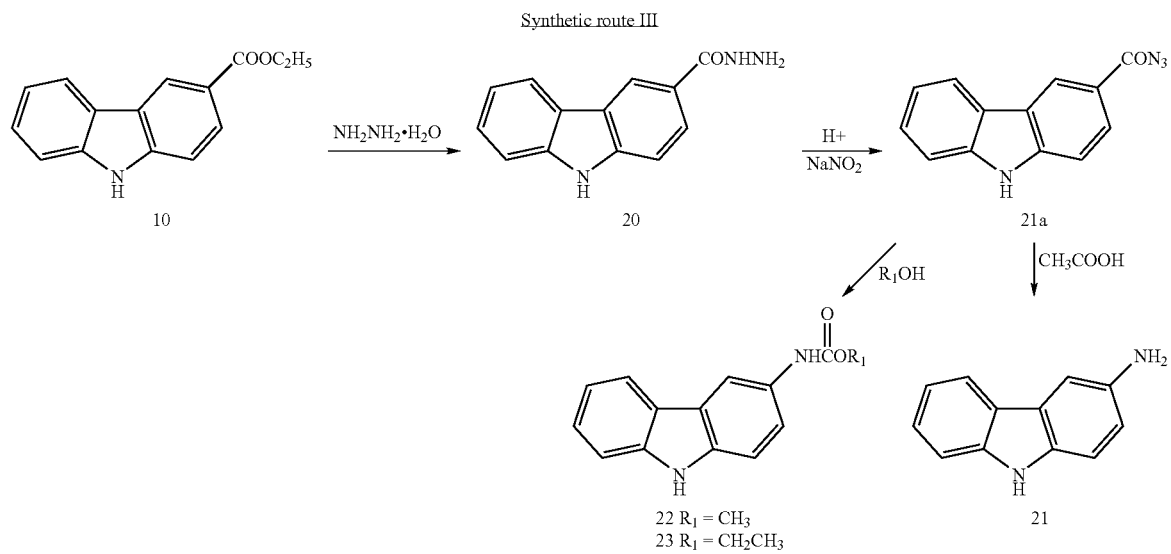

Example 42

Synthesis of β-carboline-3-carbohydrazine (20)

Ethyl β-carboline-3-carboxylate (10) (2.4 g, 10 mmol) was dissolved in ethanol (50 ml) followed by adding 85% hydrazine hydrate (15 ml). The mixture was refluxed for 6 h and concentrated to 30 ml in reduced pressure. After cooling, filtration, wash with ethanol, and natural drying in the air, white solids were obtained (2.0 g, 80%), Samples for analysis could be recrystallized with 90% ethanol to form white flaring crystals, and mp 289-290° C. (reference[100]: 289-291° C.).

Example 43

Synthesis of 3-(azidocarbonyl)-β-carboline (21a)

Concentrated HCl (1.0 ml) was added dropwise into a mixed suspension formed from compound 20 (2.0 g, 2.9 mmol) and water (50 ml). The light yellow solution was cooled in an ice bath to 0° C., and then an aqueous solution (10 ml) of nitrous acid (0.2 g, 2.9 mmol) was added dropwise to react with the light yellow solution at 0° C. for 30 minutes. The mixed reaction solution was then alkalified with a saturated NaHCO$_3$ solution. Solids were collected by filtration, washed by water and vacuumly dried to afford light yellow solids (0.51 g, 77%). Said solids were apt to be decomposed, and further purification was not necessary and used directly for the next steps.

Example 44

Synthesis of 3-amino-β-carboline (21)

Compound 21a (0.6 g, 2.5 mmol) was dissolved in a solution of 30 ml water/glacial acetic acid (1:1). The mixture was refluxed for 1 h. Accompanied with the formation of carbon dioxide gas, the raw materials was gradually disappeared. Then the solvent was evaporated in reduced pressure. The solid residues were recrystallized by ethyl acetate and then filtered to obtain yellow sheet-like crystals (0.35 g, 77%), and mp 288-290° C. (reference[100]: 289 to 291° C.).

Example 45

Synthesis of 3-[(methoxycarbonyl)amino]-β-carboline (22)

Compound 21a (0.2 g, 0.84 mmol) was dissolved in methanol (50 ml). The mixture was refluxed for 10 h. The reaction mixture was cooled, concentrated to 40 ml in vacuum, recrystallized and filtered to obtain white solids (0.12 g, 60%). Samples for analysis could be recrystallized with ethanol, and mp 180-182° C., and then decomposed at 230° C.

Example 46

Synthesis of 3-[(ethoxycarbonyl)amino]-β-carboline (23)

Compound 21a (0.2 g, 0.84 mmol) was dissolved in ethanol (50 ml). The mixture was refluxed for 10 h. The reaction liquid was cooled and concentrated to 40 ml in vacuum. After recrystallization and filtration, white solids (0.12 g, 60%) were obtained. Samples for analysis could be recrystallized with ethanol, and mp 222-224° C.

Synthetic route IV

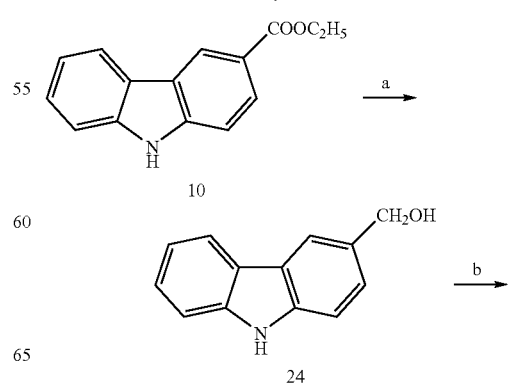

Example 47

Synthesis of 3-hydroxymethyl-β-carboline (24)

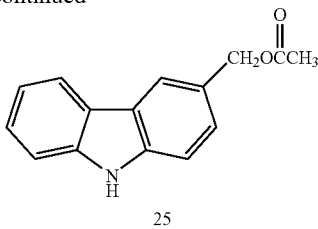

a) LiBH₄, THF; b) HAc

Compound 10 (7.0 g, 31 mmol) was dissolved in anhydrous THF (900 ml) followed by the addition of LiBH$_4$ (3.4 g, 155 mmol). The mixture was stirred at room temperature for 9 h and then cooled. Water (100 ml) was added into the mixture and stirred overnight. Then the solvent was removed in reduced pressure. With the addition of water (500 ml), extraction was conducted with dichloromethane (1 L) and then with ethyl acetate. The organic phases were combined, concentrated in vacuum and purified by silica gel column chromatography with ethyl acetate/methane (3:1) as the eluent to afford white solids (5.0 g, 82%), and mp 228-230° C. (reference[2]: 225-228° C.).

Example 48

Synthesis of 3-acetylmethoxy-β-carboline (25)

Compound 24 (1.98 g, 10 mmol) was mixed with acetic acid (50 ml).

The mixture was refluxed for 2 h. The solvent was removed in reduced pressure. Water (100 ml) was added. The mixture was extracted with ethyl acetate. The organic phases were combined, washed with water and brine, dried over anhydrous sodium sulfate, concentrated in vacuum, and recrystallized with ethyl ether to afford white needle crystals (2.2 g, 92%), and mp 131-132° C.

Physico-Chemical Properties, TLC and Spectra Analyses of 3- and 1,3-Substituted-β-Carboline Derivatives

TABLE 9

Physico-chemical data of 3- and 1,3-substituted-β-carboline derivatives

| Compd | Formula | FW | Yield (%) | Appearance | Solubility | Mp (° C.) |
|---|---|---|---|---|---|---|
| 9 | $C_{13}H_{10}N_2O_2$ | 226 | 66 | white solids | soluble in alcohols, esters etc. | 259-260 |
| 10 | $C_{14}H_{12}N_2O_2$ | 240 | 77 | white solids | soluble in alcohols, esters etc. | 230-231 |
| 11 | $C_{15}H_{14}N_2O_2$ | 254 | 48 | white solids | soluble in alcohols, esters etc. | 217-218 |
| 12 | $C_{16}H_{16}N_2O_2$ | 268 | 47 | white solids | soluble in alcohols, esters etc. | 209-210 |
| 13 | $C_{17}H_{18}N_2O_2$ | 282 | 58 | white solids | soluble in alcohols, esters etc. | 194-195 |
| 14 | $C_{19}H_{14}N_2O_2$ | 302 | 69 | white solids | soluble in alcohols, esters etc. | 257-258 |
| 15 | $C_{20}H_{16}N_2O_3$ | 332 | 63 | white solids | soluble in alcohols, esters etc. | 229-230 |
| 16 | $C_{19}H_{14}N_2O_3$ | 318 | 56 | white solids | soluble in alcohols, esters etc. | 267-269 |
| 17 | $C_{12}H_8N_2O_2$ | 212 | 90 | light yellow solids | soluble in alcohols and DMSO | 307-309 |
| 18 | $C_{16}H_{16}N_2O_2$ | 268 | 67 | white solids | soluble in alcohols, esters etc. | 211-212 |
| 19 | $C_{14}H_{14}N_4O$ | 254 | 30 | white solids | soluble in alcohols and DMSO | 233-236 |
| 20 | $C_{12}H_{10}N_4O$ | 226 | 80 | white flaring crystals | slightly soluble in alcohols, soluble in DMSO | 289-290 |
| 21 | $C_{11}H_9N_3$ | 183 | 77 | yellow solids | slightly soluble in alcohols, soluble in DMSO | 289-291 |
| 22 | $C_{13}H_{11}N_3O_2$ | 241 | 60 | white solids | soluble in alcohols, esters etc. | 180-182 |
| 23 | $C_{14}H_{13}N_3O_2$ | 255 | 60 | white solids | soluble in alcohols, esters etc. | 221-223 |

TABLE 9-continued

Physico-chemical data of 3- and 1,3-substituted-β-carboline derivatives

| Compd | Formula | FW | Yield (%) | Appearance | Solubility | Mp (° C.) |
|---|---|---|---|---|---|---|
| 24 | $C_{12}H_{10}N_2O$ | 198 | 82 | white solids | soluble in alcohols, esters etc. | 226-228 |
| 25 | $C_{14}H_{12}N_2O_2$ | 240 | 92 | white needle-like crystals | soluble in alcohols, ethers, esters, chlorofom etc. | 131-132 |

TABLE 10

FAB-MS, IR and UV data of 3- and 1,3-substituted-β-carboline derivatives

| Comp | Formula | FAB-MS m/e (M + 1) | IR (KBr, cm$^{-1}$) | UV$_{\lambda\,max}$ (nm) |
|---|---|---|---|---|
| 9 | $C_{13}H_{10}N_2O_2$ | 227 | 3258, 1724, 1627, 1502, 1434 1341, 1301, 1251, 1100, 1022 | ND |
| 10 | $C_{14}H_{12}N_2O_2$ | 241 | ND | ND |
| 11 | $C_{15}H_{14}N_2O_2$ | 255 | 3316, 3041, 2978, 1709, 1567, 1499, 1367, 1344, 1254, 1145, 1031 | 345, 330, 303, 270, 236, 219, 204 |
| 12 | $C_{16}H_{16}N_2O_2$ | 269 | 3327, 2974, 2930, 1705, 1566, 1498, 1451, 1346, 1257, 1143, 1043 | 345, 331, 303, 270, 236 |
| 13 | $C_{17}H_{18}N_2O_2$ | 283 | 3329, 2963, 1706, 1567, 1498, 1367, 1344, 1252, 746 | 346, 331, 302, 271, 237 |
| 14 | $C_{19}H_{14}N_2O_2$ | 303 | 3315, 1720, 1623, 1350, 1251, 1215, 1098, 739 | 355, 344, 279, 231 |
| 15 | $C_{20}H_{16}N_2O_3$ | 333 | 3639, 3320, 1714, 1611, 1512, 1351, 1255, 1103, 1033, 833, | 357, 347, 284, 268, 230, 215 |
| 16 | $C_{19}H_{14}N_2O_3$ | 319 | 3459, 3159, 1715, 1691, 1610, 1513, 1432, 1352, 1260, 839, | 387, 340, 327, 285, 215 |
| 17 | $C_{12}H_8N_2O_2$ | 213 | 2250-3750, 1630, 1585, 1372, 1219, 752 | 356, 337, 288, 282, 234, 212 |
| 18 | $C_{16}H_{16}N_2O_2$ | 269 | 3233, 2957, 2868, 1708, 1627, 1553, 1501, 1462, 1339, 1304, 1248, 1102 | ND |
| 19 | $C_{14}H_{14}N_4O$ | 255 | ND | ND |
| 20 | $C_{12}H_{10}N_4O$ | 227 | ND | ND |
| 21 | $C_{11}H_9N_3$ | 184 | ND | ND |
| 22 | $C_{13}H_{11}N_3O_2$ | 242 | ND | ND |
| 23 | $C_{14}H_{13}N_3O_2$ | 256 | ND | ND |
| 24 | $C_{12}H_{10}N_2O$ | 199 | ND | ND |
| 25 | $C_{14}H_{12}N_2O_2$ | 241 | 3371, 2938, 1743, 1692, 1616, 1450, 1372, 1238, 1053 | 326, 315, 284, 259, 230, 207 |

Note:
ND represents that said assessment was not conducted.

TABLE 11

$^1$H-NMR data of 3- and 1,3-substituted-β-carboline derivatives

| Compd | 1H-NMR (δ, CDCl3) |
|---|---|
| 11 | 10.50 (1H, s, NH), 8.78 (1H, s, H-4), 8.15-8.17 (1H, d, J = 8 Hz, H-8), 7.58-7.60 (1H, d, J = 8 Hz, H-5), 7.52-7.55 (1H, m, H-6), 7.30-7.33 (1H, m, H-7), 4.44-4.48 (2H, m, OCH$_2$CH$_3$), 2.68 (3H, s, CH$_3$), |
| 12 | 9.63 (1H, s, NH), 8.76 (1H, s, H-4), 8.16-8.17 (1H, d, J = 8 Hz, H-8), 7.60-7.62 (1H, d, J = 8.5 Hz, H-5), 7.54-7.57 (1H, m, H-6), 7.31-7.34 (1H, m, H-7), 4.47-4.51 (2H, m, OCH$_2$CH$_3$), 3.11-3.15 (2H, m, CH$_2$CH$_3$), 1.40-1.43 (3H, m, OCH$_2$CH$_3$), 1.29-1.32 (3H, m, CH$_2$CH$_3$) |
| 13 | 11.14 (1H, s, —NH), 8.79 (1H, s, H-4), 8.15-8.17 (1H, d, J = 7.5 Hz, H-8), 7.64-7.66 (1H, d, J = 8 Hz, H-5), 7.51-7.54 (1H, m, H-6), 7.25-7.31 (1H, m, H-7), 4.42-4.46 (2H, m, OCH$_2$CH$_3$), 2.76-2.79 (2H, m, ArCH$_2$CH$_2$CH$_3$), 1.45-1.51 (2H, m, ArCH$_2$CH$_2$CH$_3$), 1.25-1.32 (3H, m, OCH$_2$CH$_3$), 0.37-0.43 (3H, m, CH$_2$CH$_2$CH$_3$) |
| 14 | 8.91 (1H, s, NH), 8.86 (1H, s, H-4), 8.20-8.21 (1H, d, J = 8 Hz, H-8), 7.90-7.91 (2H, m, H-5, H-6) 7.58-7.60 (2H, m, H-7, Ar—H), 7.54-7.57 (2H, m, Ar—H), 7.41-7.44 (1H, m, Ar—H), 7.35-7.37 (1H, m, Ar—H), 4.04 (3H, s, OCH$_3$) |
| 15 | 9.40 (1H, s, NH), 8.76 (1H, s, H-4), 8.15-8.16 (1H, d, J = 8 Hz, H-8), 7.69-7.70 (2H, d, J = 8.5 Hz, H-5, H-6), 7.54-7.56 (2H, m, H-7, Ar—H), 7.31-7.34 (1H, m, Ar—H), 6.75-6.77 (2H, d, J = 8.5 Hz, Ar—H), 4.00 (3H, s, OCH$_3$), 3.69 (3H, s, Ar—OCH$_3$) |
| 16 | 9.51 (1H, s, NH), 8.83 (1H, d, J = 8 Hz, H-4), 8.20-8.21 (1H, d, J = 8 Hz, H-8), 7.83-7.85 (2H, d, J = 8.5 Hz, H-5, H-6), 7.60-7.61 (2H, m, H-7, Ar—H), 7.38-7.39 (1H, m, Ar—H), 7.03-7.04 (2H, d, J = 8 Hz, Ar—H), 4.06 (3H, s, OCH$_3$) |

TABLE 11-continued $^1$H-NMR data of 3- and 1,3-substituted-β-carboline derivatives

| Compd | 1H-NMR (δ, CDCl3) |
|---|---|
| 18 | 11.74 (1H, s, NH), 9.29 (1H, s, H-4), 8.89 (1H, s, H-1 ), 8.20-8.22 (1H, d, J = 8.0 Hz, H-8), 7.86-7.87 (1H, d, J = 8.5 Hz, H-5), 7.58-7.62 (1H, m, H-6), 7.33-7.36 (1H, m, H-7), 4.51-4.54 (2H, m, $CH_2CH_2CH_2$—$CH_3$), 1.81-1.87 (2H, m, $CH_2CH_2CH_3$), 1.48-1.56 (2H, m, $CH_2CH_2CH_2CH_3$), 0.97-1.00 (3H, m, $CH_2CH_2CH_2CH_3$) |
| 25 | 9.47 (1H, s, NH), 9.03 (1H, s, H-4), 8.32-8.34 (1H, d, J = 8 Hz, H-1), 8.26-8.28 (1H, d, J = 8.5 Hz, H-8), 8.19-8.20 (2H, m, H-5), 7.67-7.70 (1H, m, H-6), 7.47-7.51 (1H, m, H-7), 5.29 (2H, s, $CH_2$), 2.16 (3H, s, $CH_3$) |

Synthesis of 3,9-disubstituted-β-carboline derivatives

Experimental Instruments and Materials

Experimental instruments are as described above.

Chemical Reagents

NaH (Merck-Schuchardt Co. Germany), methyl iodide (analytically pure, Zhenjiang Yuhuan Biological Reagent Plant), ethyl iodide (analytically pure, Zhenjiang Yuhuan Biological Reagent Plant), iodo-n-butane (chemically pure, Shanghai Chemical Reagent Co., China National Pharmaceutical Group), 1-bromine-3-phenyl propane (Acros Organic, U.S.), α-bromine-2,3,4,5,6-pentafluorobenzyl (Acros Organic, U.S.), 2-bromine-acetyl benzophenone (Acros Organic, U.S.), 2-bromine-4-phenyl-acetyl benzophenone (Acros Organic, U.S.), tetrahydro potassium aluminium (Acros Organic, U.S.), and other domestically manufactured analytically pure or chemically pure reagents were used.

Synthetic Routes and Operational Steps

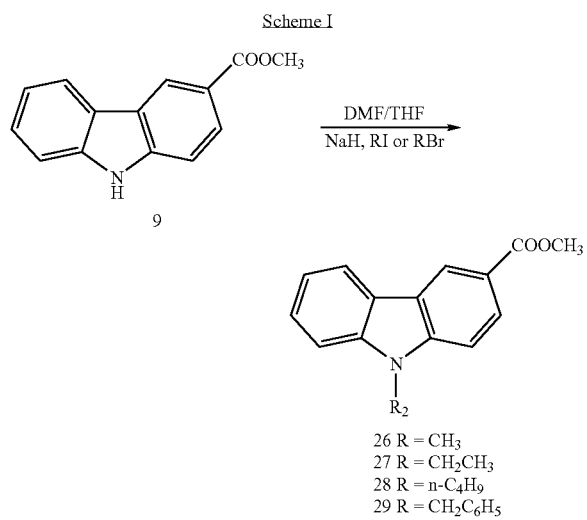

Scheme I

26 R = $CH_3$
27 R = $CH_2CH_3$
28 R = n-$C_4H_9$
29 R = $CH_2C_6H_5$

Example 49

General procedure for the preparation of 9-substituted-β-carboline-3-carboxylate β-carboline-3-carboxylate (10 mmol), DMF (50 ml) and THF (50 ml) were respectively added in a 250 ml round-bottom flask, and were stirred until the mixture became clear at room temperature. NaH (50 mmol) was added and stirred until there were no bubbles formed. Alkyl halide or aromatic halide (60 mmol) was added dropwise. The mixture was stirred to react at room temperature or by heating for 5 h. After the reaction was finished, THF was removed in reduce pressure, and 200 ml 2N HCl solution was added. The mixture was extracted with toluene. The aqueous phase was neutralized with saturated $NaHCO_3$ and extracted with ethyl acetate. The organic phases were combined, washed with water and brine, dried, filtered and concentrated in vacuum. The residues were purified by silica gel column chromatography with ethyl acetate as the eluent, and recrystallized with ethyl ether/petroleum ether. Examples 50 to 61 were treated according to the above procedures.

Example 50

Synthesis of methyl 9-methyl-β-carboline-3-carboxylate (26)

Afforded white needle crystals (1.8 g, 75%), and mp 215-216° C.

Example 51

Synthesis methyl 9-ethyl-β-carboline-3-carboxylate (27)

Afforded white needle crystals (2.0 g, 79%), and mp 155-156° C.

Example 52

Synthesis of methyl 9-n-butyl-β-carboline-3-carboxylate (28)

Afforded white needle crystals (2.3 g, 82%), and mp 181-183° C.

Example 53

Synthesis of methyl 9-benzyl-β-carboline-3-carboxylate (29)

Afforded white needle crystals (2.3 g, 73%), and mp 187-188° C.

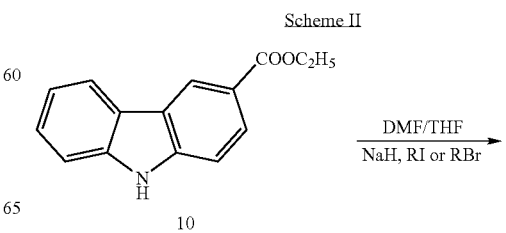

Scheme II

10

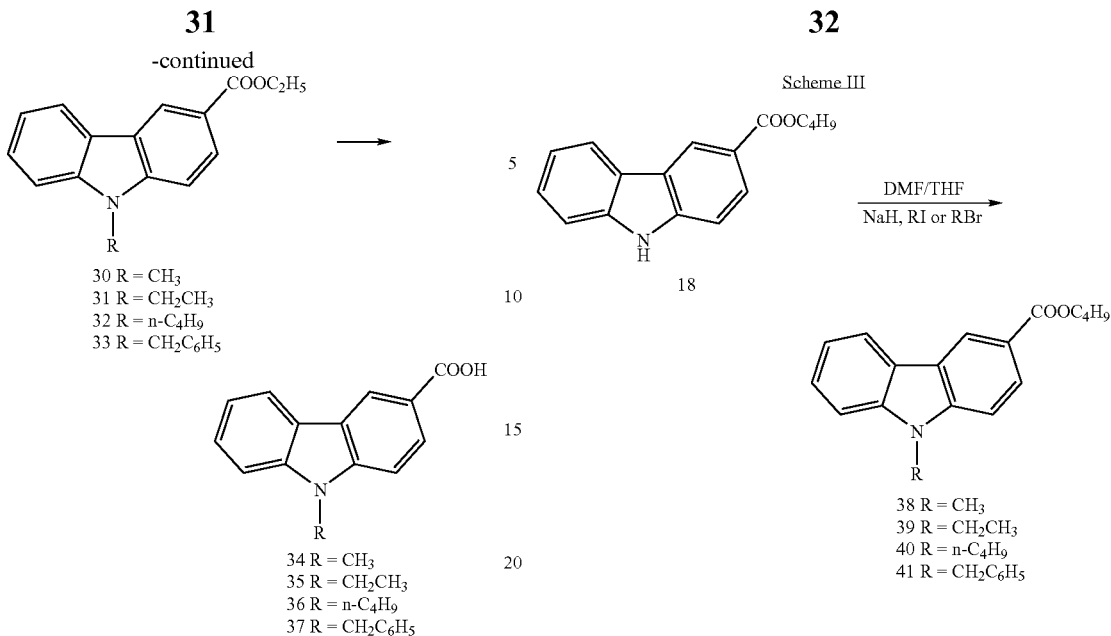

30 R = CH₃
31 R = CH₂CH₃
32 R = n-C₄H₉
33 R = CH₂C₆H₅

34 R = CH₃
35 R = CH₂CH₃
36 R = n-C₄H₉
37 R = CH₂C₆H₅

38 R = CH₃
39 R = CH₂CH₃
40 R = n-C₄H₉
41 R = CH₂C₆H₅

Example 54

Synthesis of ethyl 9-methyl-β-carboline-3-carboxylate (30)

white needle crystals (1.9 g, 75%) were obtained, mp 139-140° C.

Example 55

Synthesis of ethyl 9-ethyl-β-carboline-3-carboxylate (31)

white needle crystals (1.8 g, 67%) were obtained, mp 117-118° C.

Example 56

Synthesis of ethyl 9-butyl-β-carboline-3-carboxylate (32)

white needle crystals (2.3 g, 78%), mp 76-77° C.

Example 57

Synthesis of ethyl 9-benzyl-β-carboline-3-carboxylate (33)

Ethyl β-carboline-3-carboxylate 10 (4.8 g, 20 mmol), DMF (100 ml) and THF (100 ml) were respectively added in a 100 ml round-bottom flask, and were stirred at room temperature for 15 minutes, then 60% NaH (2.4 g, 60 mmol) was added and stirred until there were no bubbles formed. Benzyl bromide (15 ml) was added, and the mixture was refluxed for 12 h. Later the mixture was treated in a manner similar to that described for compound 29 to afford white crystals (4.6 g, 70%), mp 126-127° C.

Example 58

Synthesis of butyl 9-methyl-β-carboline-3-carboxylate (38)

white needle crystals (2.0 g, 70%) were obtained, mp 235-238° C.

Example 59

Synthesis of butyl 9-ethyl-β-carboline-3-carboxylate (39)

white needle crystals (2.0 g, 65%) were obtained, mp 86-88° C.

Example 60

Synthesis of butyl 9-butyl-β-carboline-3-carboxylate (40)

2.2 g white needle crystals were obtained, the yield was 74%, and mp 94-95° C.

Example 61

Synthesis of butyl 9-benzyl-β-carboline-3-carboxylate (41)

white crystals (11.0 g, 67%) were obtained, mp 104-105° C.

Example 62

General procedure for the preparation of 9-substituted-β-carboline-3-carboxylic acid 9-Substituted-β-carboline-3-carboxylate (20 mmol), 200 ml of water, 100 ml of ethanol and NaOH (4.0 g, 100 mmol) were added in a 250 ml round-bottom flask. The mixture was refluxed for 2 h and then cooled. The pH was adjusted to 6 with 5N HCl. After removing ethanol in reduced pressure, light yellow solids were precipitated which were then cooled, filtered, washed with water and dried. Examples 63 to 66 were conducted according to the above operational steps.

Example 63

Synthesis of 9-methyl-β-carboline-3-carboxylic acid (34)

light yellow solids were obtained, the yield was 99%, and mp 267-269° C.

Example 64

Synthesis of 9-ethyl-β-carboline-3-carboxylic acid (35)

light yellow solids were obtained, the yield was 98%, and mp 201-202° C.

Example 65

Synthesis of 9-butyl-β-carboline-3-carboxylic acid (36)

Compound 32 (3.0 g, 10 mmol), 100 ml of water, 50 ml of ethanol, and NaOH (2.0 g, 50 mmol) were added into a 100 ml round-bottom flask. The mixture was refluxed for 2 h. The subsequent operational steps were conducted according to those for synthesizing compound 3 to obtain light yellow solids (2.7 g, 99%), and mp 182-184° C.

Example 66

Synthesis of 9-benzyl-β-carboline-3-carboxylic acid (37)

yellow solids were obtained, the yield was 94%, and mp 261-262° C.

Scheme IV

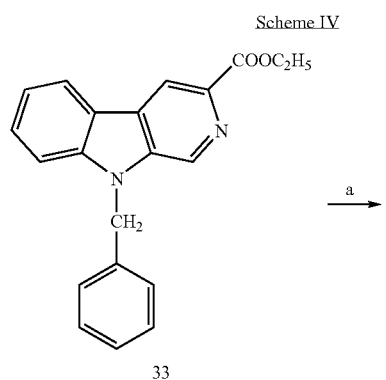

33

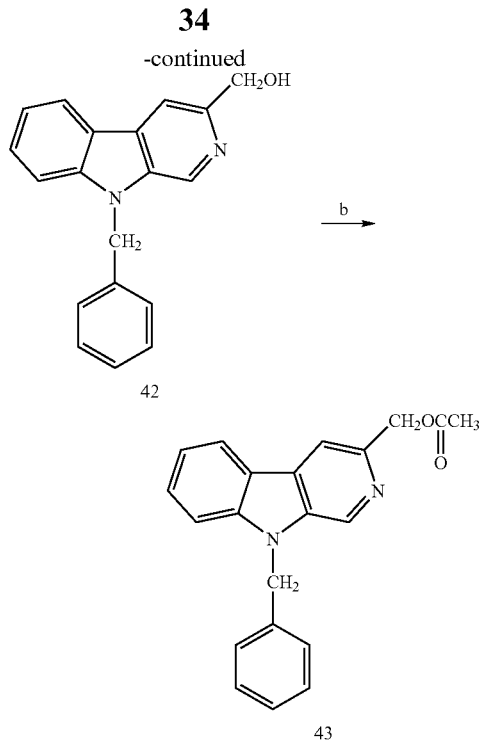

42

43 a) LiAlH4, THF; b) HAc

Example 67

Synthesis of 9-benzyl-3-hydroxymethyl-β-carboline (42)

Compound 33 (3.3 g, 10 mmol) was mixed with anhydrous THF (100 ml). The mixture was added dropwise to a mixed solution of $LiAlH_4$ (1.2 g, 30 mmol) and anhydrous THF (100 ml). After that, the mixture was refluxed for 10 h. Then the mixture was cooled to room temperature. 10% NaOH (50 ml) was added into the mixture and then stirred for 20 minutes. The mixture was extracted with ethyl acetate, the organic phases were combined and washed with water and brine, dried over anhydrous sodium sulfate, filtered, evaporated and purified by silica gel column chromatography with ethyl acetate as the eluent. Upon recrystallization, white solids (1.5 g, 52%) were obtained, mp 120-122° C.

Example 68

Synthesis of 9-benzyl-3-acetylmethoxy-β-carboline (43)

Compound 42 (1.44 g, 5 mmol) was mixed with acetic acid (50 ml). The mixture was refluxed for 2 h. After the reaction was finished, the solvent was evaporated in reduced pressure. Water (100 ml) was added into the residues, and then the mixture was extracted with ethyl acetate. The organic phases were combined, washed with water and brine, dried over anhydrous sodium sulfate, concentrated in vacuum, and recrystallized with ethyl acetate, white solids (1.5 g, 94%) were obtained, mp 141-142° C.

Scheme V

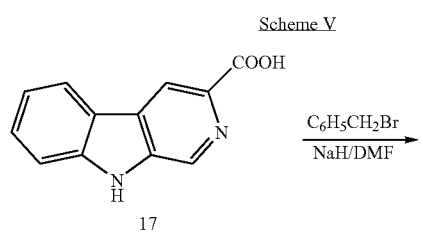

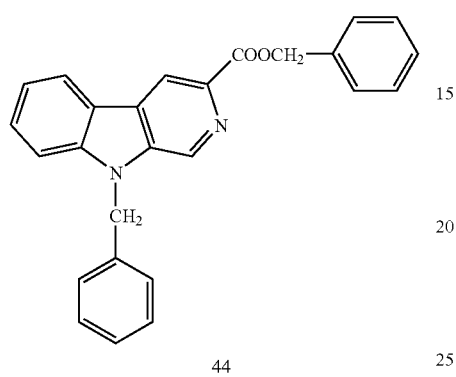

Example 69

Synthesis of benzyl 9-benzyl-β-carboline-3-carboxylate (44)

Compound 17 (2.12 g, 10 mmol) was mixed with DMF (50 ml). After stirring the mixture at room temperature for 30 minutes, NaH (1.6 g, 40 mmol) was added and stirred until the solution became clear. After that, benzyl bromide (5 ml) was added. The mixture was stirred and reacted at room temperature for 1 h. The reaction mixture was poured into cold water (200 ml) and the mixture was extracted with ethyl acetate. The organic phases were combined and washed with water and brine, then the organic phase was evaporated in reduced pressure, the residue was dissolved in anhydrous ethanol, and then the mixture was adjusted to pH 4 with concentrated HCl, and evaporated and recrystallized with acetone/ethyl ether, light yellow solids were obtained. The light yellow solids were dissolved in a mixed solution of water and ethyl acetate. The pH was adjusted to 8 with saturated NaHCO₃ solution. The organic phases were isolated. The aqueous layer was extracted with ethyl acetate. After drying, decolorization with activated carbon, filtration, concentration, and recrystallization with ethyl ether, white solids (2.3 g, 57%) were obtained, mp 169-170° C.

Scheme VI

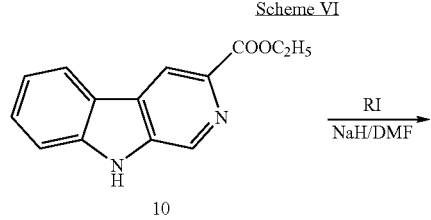

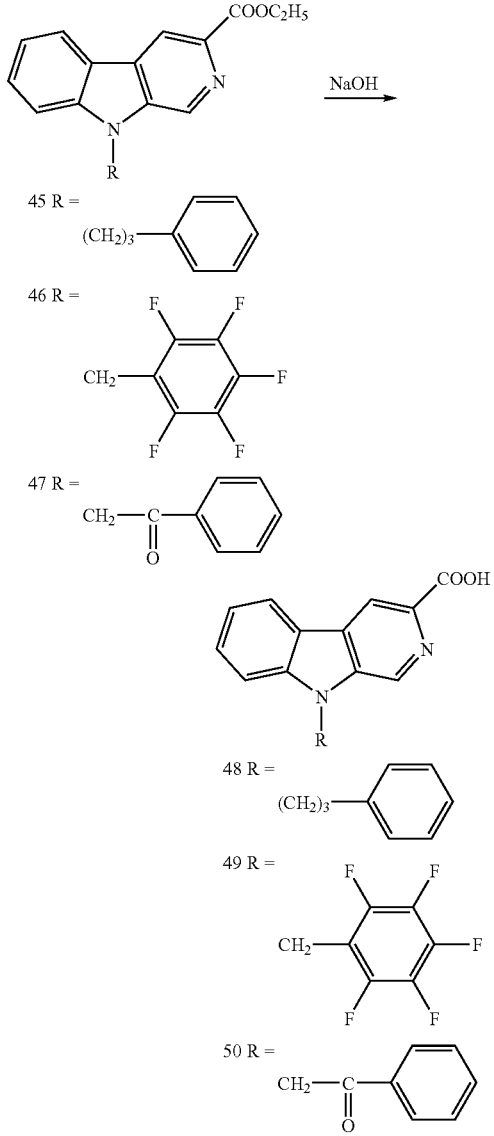

Example 70

Synthesis of ethyl 9-phenylpropyl-β-carboline-3-carboxylate (45)

Compound 10 (1.2 g, 5 mmol) was mixed with DMF (30 ml). After stirring the mixture at room temperature for 15 minutes, NaH (0.6 g, 15 mmol) was added and stirred until the solution became clear. After that, 1-bromine-3-phenylpropane (2 ml) was added. The mixture was refluxed for 4 h. THF was evaporated in reduced pressure. The resulting solution was added 200 ml 2N HCl solution. The mixture was extracted with ethyl ether. The aqueous phase was neutralized by saturated NaHCO₃ solution and then extracted with ethyl acetate. The organic phases were combined, washed with water and brine, dried over sodium sulfate, filtered, concentrated in vacuum and purified with silica gel column chromatography with ethyl acetate as the eluent. Upon recrystallization, white needle crystals (1.0 g, 56%) were obtained, mp 140-142° C.

Example 71

Synthesis of ethyl 9-(2',3',4',5',6'-pentafluoro)benzyl-β-carboline-3-carboxylate (46)

Compound 10 (1.2 g, 5 mmol) was mixed with DMF (30 ml). After stirring the mixture at room temperature for 15 minutes, NaH (0.6 g, 15 mmol) was added and stirred until the solution became clear. After that, α-bromine-2,3,4,5,6-pentafluorobenzyl (1 ml) was added. The mixture was stirred at room temperature for 1 hour. The subsequent steps were conducted according to those for synthesizing compound 45 to afford white crystals (1.3 g, 62%), mp 153-154° C.

Example 72

Synthesis of ethyl 9-acetophenone-β-carboline-3-carboxylate (47)

Compound 10 (1.2 g, 5 mmol) was mixed with DMF (30 ml). After stirring the mixture at room temperature for 15 minutes, NaH (0.6 g, 15 mmol) was added and stirred until the solution became clear. After that, 2-bromine-acetyl benzophenone (2.0 g) was added. The mixture was refluxed for 4 h. The subsequent steps were conducted according to those for synthesizing compound 45 to afford white crystals (0.9 g, 50%), and mp 246-248° C.

Example 73

General procedure for the preparation of 9-substituted-β-carboline-3-carboxylic acid 9-Substituted-β-carboline-3-carboxylate (10 mmol), NaOH (50 mmol), water (100 ml) and ethanol (50 ml) were mixed. The mixture was refluxed for 2 h. The reaction mixture was cooled to room temperature, and the pH was adjusted to 6 with 5M HCl. After cooling, filtration, wash with water, drying, light yellow solids were obtained. Examples 74 to 76 were treated according to the above operational steps.

Example 74

Synthesis of 9-phenylpropyl-β-carboline-3-carboxylic acid (48)

light yellow solids were obtained, the yield was 97%, and mp 213-215° C.

Example 75

Synthesis of 9-(2',3',4',5',6'-pentafluoro)benzyl-β-carboline-3-carboxylic acid (49)

white solids were obtained, the yield was 98%, and mp>270° C.

Example 76

Synthesis of 9-acetophenone-β-carboline-3-carboxylic acid (50)

light yellow solids (1.6 g, 97%) were obtained, mp>270° C.

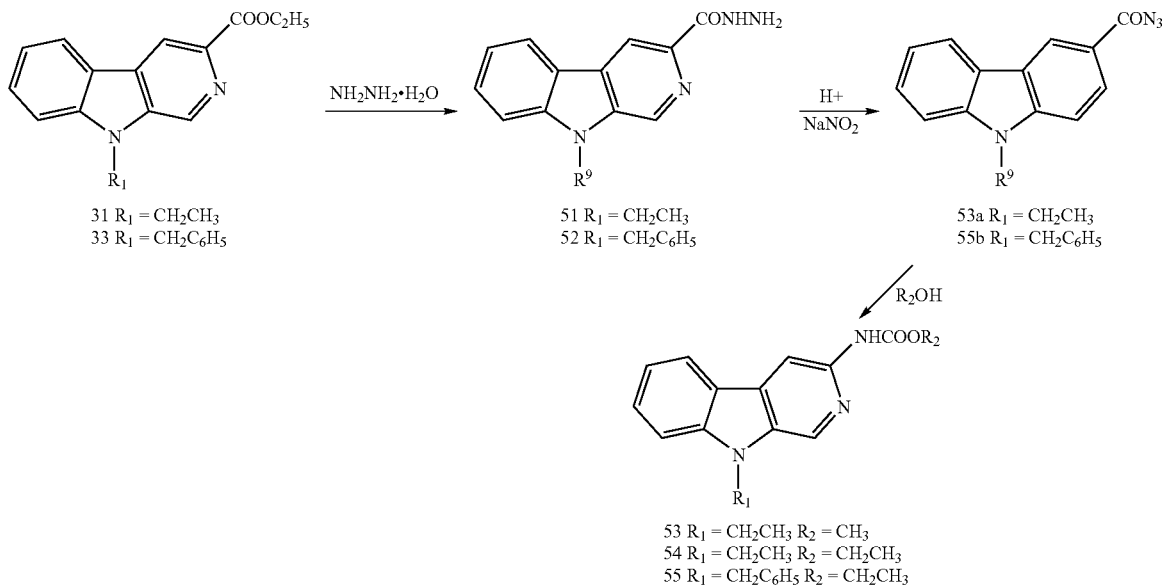

Scheme VII

Example 77

Synthesis of 3-carbohydrazine 9-ethyl-β-carboline (51)

Compound 31 (2.7 g, 10 mmol) was dissolved into ethanol (50 ml). 85% Hydrazine hydrate (15 ml) was added. The mixture was refluxed by heating for 6 h and concentrated to 30 ml in reduced pressure. After cooling, filtration, wash with ethanol, and natural drying in the air, white solids (2.0 g, 83%) were obtained. Samples for analysis could be recrystallized by 90% ethanol to obtain white flaring sheet-like crystals, mp 195-196° C.

Example 78

Synthesis of 3-(azidocarbonyl)-9-ethyl-β-carboline (53a)

Concentrated HCl (20 ml) was added dropwise into a mixed suspension formed from compound 51 (2.54 g, 10 mmol) and water (200 ml). The light yellow solution was cooled in an ice bath to 0° C., and then an aqueous solution (30 ml) of nitrous acid (2.1 g, 30 mmol) was added dropwise to react with the light yellow solution at 0° C. for 30 minutes. The mixed reaction solution was then alkalified with a saturated NaHCO$_3$ solution. Solids were collected by filtration. After being washed by water and vacuumly dried, yellow solids (2.3 g) were obtained. The solids were apt to be decomposed and further purification was not necessary and used directly for the next steps.

Example 79

Synthesis of 9-ethyl-3-[(methoxycarbonyl)amino]-β-carboline (53)

Compound 53a (0.6 g, 5 mmol) was dissolved into methanol (50 ml). The mixture was refluxed for 10 h. The reaction liquid was cooled and concentrated to 30 ml in vacuum. After recrystallization with anhydrous ethanol, filtration, wash with a small amount of ethanol, white solids (0.4 g, 59%) were obtained, mp 213-214° C.

Example 80

Synthesis of 3-[(ethoxycarbonyl)amino]-9-ethyl-β-carboline (54)

Compound 53a (1.32 g, 5 mmol) was dissolved into ethanol (100 ml). The mixture was refluxed for 10 h. The reaction liquid was cooled and concentrated to 30 ml in vacuum. After recrystallization and filtration, white solids (0.8 g, 56%) were obtained, mp 217-218° C.

Example 81

Synthesis of 3-carbohydrazide-9-benzyl-β-carboline (52)

Compound 33 (3.3 g, 10 mmol) was dissolved into ethanol (100 ml). 85% Hydrazine hydrate (20 ml) was added. The mixture was refluxed for 10 h and concentrated to 50 ml by decompression. After cooling, filtration, wash with ethanol, and natural drying in the air, white solids (2.8 g, 87%) were obtained, and mp 209-211° C.

Example 82

Synthesis of 3-(azidocarbonyl)-9-benzyl-β-carboline (55a)

Concentrated HCl (20 ml) was added dropwise into a mixed suspension formed from compound 55a (3.16 g, 10 mmol) and water (500 ml). The light yellow solution was cooled in an ice bath to 0° C., and then an aqueous solution (50 ml) of nitrous acid (2.1 g, 30 mmol) was added dropwise to react with the light yellow solution at 0° C. for 30 minutes. The mixed reaction solution was then alkalified with a saturated NaHCO$_3$ solution. Solids were collected by filtration. After being washed by water and vacuumly dried, yellow solids (2.9 g) were obtained with a tendency to decompose. The material was used without further purification for the following steps.

Example 83

Synthesis of 3-[(ethoxycarbonyl)amino]-9-benzyl-β-carboline (55)

Compound 55a (2.9 g, 8.86 mmol) was dissolved into ethanol (150 ml). The mixture was refluxed 10 h. The reaction liquid was cooled and concentrated to 30 ml in reduced pressure. After recrystallization with ethyl acetate, white solids (1.8 g, 57%) were obtained. Samples for analysis could be recrystallized by 90% ethanol, and mp 217-218° C.

Physico-Chemical Properties, TLC and Spectra Analyses of 3,9-Disubstituted-β-Carboline Derivatives

TABLE 12

Physico-chemical data of 3,9-disubstituted β-carboline derivatives

| Compd | Formula | FW | Yield (%) | Appearance | Solubility | Mp (° C.) |
|---|---|---|---|---|---|---|
| 26 | $C_{14}H_{12}N_2O_2$ | 240 | 75 | white needle-like crystals | soluble in alcohols, ethers, esters, chloroform etc. | 215-216 |
| 27 | $C_{15}H_{14}N_2O_2$ | 254 | 79 | white needle-like crystals | soluble in alcohols, ethers, esters, chloroform etc. | 155-156 |
| 28 | $C_{17}H_{18}N_2O_2$ | 282 | 82 | white needle-like crystals | soluble in alcohols, ethers, esters, chloroform etc. | 181-183 |
| 29 | $C_{20}H_{16}N_2O_2$ | 316 | 73 | white crystals | soluble in alcohols, ethers, esters, chloroform etc. | 187-188 |
| 30 | $C_{15}H_{14}N_2O_2$ | 254 | 75 | white needle-like crystals | soluble in alcohols, ethers, esters, chloroform etc. | 139-140 |

TABLE 12-continued

Physico-chemical data of 3,9-disubstituted β-carboline derivatives

| Compd | Formula | FW | Yield (%) | Appearance | Solubility | Mp (° C.) |
|---|---|---|---|---|---|---|
| 31 | $C_{16}H_{16}N_2O_2$ | 268 | 67 | white needle-like crystals | soluble in alcohols, ethers, esters, chloroform etc. | 117-118 |
| 32 | $C_{19}H_{22}N_2O_2$ | 296 | 78 | white needle-like crystals | soluble in alcohols, ethers, esters, chloroform etc. | 76-77 |
| 33 | $C_{21}H_{18}N_2O_2$ | 330 | 70 | white solids | soluble in alcohols, ethers, esters, chloroform etc. | 126-127 |
| 34 | $C_{13}H_{10}N_2O_2$ | 226 | 99 | light yellow solids | soluble in alcohols and DMSO | 267-269 |
| 35 | $C_{14}H_{12}N_2O_2$ | 240 | 98 | light yellow solids | soluble in alcohols and DMSO | 201-202 |
| 36 | $C_{16}H_{16}N_2O_2$ | 268 | 99 | light yellow solids | soluble in alcohols and DMSO | 182-184 |
| 37 | $C_{19}H_{14}N_2O_2$ | 302 | 94 | light yellow solids | soluble in DMSO | 261-262 |
| 38 | $C_{17}H_{18}N_2O_2$ | 282 | 70 | white needle crystals | soluble in alcohols, ethers, esters, chloroform etc. | 235-238 |
| 39 | $C_{18}H_{20}N_2O_2$ | 296 | 65 | white needle crystals | soluble in alcohols, ethers, esters, chloroform etc. | 86-88 |
| 40 | $C_{21}H_{24}N_2O_2$ | 324 | 74 | white needle crystals | soluble in alcohols, ethers, esters, chloroform etc. | 94-95 |
| 41 | $C_{23}H_{22}N_2O_2$ | 358 | 67 | white solids | soluble in alcohols, ethers, esters, chloroform etc. | 105-106 |
| 42 | $C_{19}H_{16}N_2O_2$ | 288 | 52 | white solids | soluble in alcohols, ethers, chloroform etc. | 120-122 |
| 43 | $C_{21}H_{18}N_2O_2$ | 330 | 94 | white needle crystals | soluble in alcohols, ethers, esters, chloroform etc. | 141-142 |
| 44 | $C_{26}H_{20}N_2O_2$ | 392 | 57 | white solids | soluble in alcohols, ethers, esters, chloroform etc. | 169-170 |
| 45 | $C_{23}H_{22}N_2O_2$ | 358 | 56 | white crystals | soluble in alcohols, ethers, esters, chloroform etc. | 140-142 |
| 46 | $C_{21}F_5H_{13}N_2O_2$ | 420 | 62 | white solids | soluble in alcohols, ethers, esters, chloroform etc. | 153-154 |
| 47 | $C_{22}H_{18}N_2O_3$ | 358 | 50 | white solids | soluble in alcohols, ethers, esters, chloroform etc. | 246-248 |
| 48 | $C_{21}H_{18}N_2O_2$ | 330 | 97 | light yellow solids | soluble in DMSO | 213-215 |
| 49 | $C_{19}F_5H_9N_2O_2$ | 392 | 98 | white solids | soluble in DMSO | >270 |
| 50 | $C_{20}H_{14}N_2O_3$ | 330 | 97 | light yellow solids | soluble in DMSO | >270 |
| 51 | $C_{14}H_{14}N_4O$ | 254 | 83 | white flaring crystals | soluble in alcohols and DMSO | 195-196 |
| 52 | $C_{19}H_{16}N_4O$ | 316 | 87 | white flaring crystals | soluble in alcohols and DMSO | 209-211 |
| 53 | $C_{15}H_{15}N_3O_2$ | 269 | 59 | white solids | soluble in alcohols and esters | 213-214 |
| 54 | $C_{16}H_{17}N_3O_2$ | 283 | 56 | white solids | soluble in alcohols and esters | 217-218 |

TABLE 12-continued

Physico-chemical data of 3,9-disubstituted β-carboline derivatives

| Compd | Formula | FW | Yield (%) | Appearance | Solubility | Mp (° C.) |
|---|---|---|---|---|---|---|
| 55 | $C_{21}H_{19}N_3O_2$ | 345 | 57 | white solids | soluble in alcohols and esters | 218-219 |

TABLE 13

FAB-MS, IR and UV data of 3,9-disubstituted β-carboline derivatives

| Compd | Formula | FAB-MS m/e (M + 1) | IR (KBr, cm$^{-1}$) | UV$_{\lambda\ max}$ (nm) |
|---|---|---|---|---|
| 26 | $C_{14}H_{12}N_2O_2$ | 241 | 3386, 3089, 2548, 2056, 1730, 1631, 1525, 1497, 1431, 1376, 1282, 1207, 1115 | 358, 343, 307, 272, 236, 219 |
| 27 | $C_{15}H_{14}N_2O_2$ | 255 | 3404, 3358, 2985, 1723, 1632, 1523, 1439, 1337, 1258 | 358, 345, 306, 273, 236, 205 |
| 28 | $C_{17}H_{18}N_2O_2$ | 283 | 3446, 2958, 2866, 1734, 1624, 1584, 1551, 1428, 1361, 1245, 1102 | 358, 344, 306, 273, 236, 222 |
| 29 | $C_{20}H_{16}N_2O_2$ | 317 | 3026, 2945, 1731, 1622, 1583, 1553, 1424, 1335, 1242, 1105 | 356, 341, 304, 272, 235, 205 |
| 30 | $C_{15}H_{14}N_2O_2$ | 255 | 3446, 3397, 2602, 2015, 1721, 1628, 1587, 1328, 1207, 1110, 1012 | 357, 342, 305, 272, 236, 219 |
| 31 | $C_{16}H_{16}N_2O_2$ | 269 | 3413, 2984, 1717, 1632, 1521, 1448, 1334, 1257, 1006 | 358, 344, 305, 273, 236, 221 |
| 32 | $C_{19}H_{22}N_2O_2$ | 297 | 3437, 2956, 1731, 1623, 1552, 1465, 1366, 1210, 1102, 1024 | 358, 343, 307, 273, 235, 220 |
| 33 | $C_{21}H_{18}N_2O_2$ | 331 | 3424, 3027, 2973, 1723, 1621, 1550, 1466, 1366, 1214, 1104 | 355, 341, 304, 272, 234, 204 |
| 34 | $C_{13}H_{10}N_2O_2$ | 227 | 3406, 2250-3250, 1716, 1630, 1599, 1405, 1314, 1200 | 384, 360, 273, 241, 217 |
| 35 | $C_{14}H_{12}N_2O_2$ | 241 | 3418, 2250, 3250, 1714, 1631, 1588, 1408, 1336, 1248, 1198 | 387, 359, 347, 273, 239, 220 |
| 36 | $C_{16}H_{16}N_2O_2$ | 269 | 3424, 3062, 2956, 1690, 1629, 1500, 1467, 1371, 1296, 1132 | 387, 359, 345, 272, 238, 221 |
| 37 | $C_{19}H_{14}N_2O_2$ | 303 | 3409, 3056, 2946, 1663, 1624, 1586, 1377, 1225 | 355, 342, 267, 239 |
| 38 | $C_{17}H_{18}N_2O_2$ | 283 | 3401, 2956, 2869, 1726, 1696, 1625, 1584, 1504, 1463, 1332, 1107 | 358, 342, 305, 272, 236, 219 |
| 39 | $C_{18}H_{20}N_2O_2$ | 297 | 3423, 3052, 2963,, 2401, 1998, 1884, 1722, 1627, 1587, 1496, 1269, 1121 | 359, 345, 306, 273, 239, 220 |
| 40 | $C_{21}H_{24}N_2O_2$ | 325 | 3433, 3061, 3023, 2956, 2866 1728, 1624, 1551, 1464, 1358, 1212, 1104 | 359, 344, 307, 273, 238, 220, 205 |
| 41 | $C_{23}H_{22}N_2O_2$ | 359 | 3051, 2959, 2930, 2869, 1700, 1620, 1582, 1550,, 1462, 1361, 1298, 1246, 1107, 1052 | 355, 341, 304, 273, 235, 205 |
| 42 | $C_{19}H_{16}N_2O$ | 289 | 3170, 2938, 1627, 1559, 1495, 1467, 1363, 1264, 1205, 1048 | 361, 347, 291, 284, 239, 215 |
| 43 | $C_{21}H_{18}N_2O_2$ | 331 | 3428, 3027, 2942, 2886, 1726 1622, 1496, 1452, 1352, 1245, 1026 | 360, 346, 291, 284, 239, 214 |
| 44 | $C_{26}H_{20}N_2O_2$ | 393 | 3400, 3064, 3035, 2935, 2889, 1709, 1623, 1584, 1497, 1461, 1336, 1244, 1109 | 356, 341, 305, 273, 236 |
| 45 | $C_{23}H_{22}N_2O_2$ | 359 | 3425, 3057, 3026, 2983, 2933 2905, 1724, 1622, 1550, 1500, 1461, 1367, 1246, 1107, 1023 | 358, 342, 305, 273, 236, 217, 207 |
| 46 | $C_{21}F_5H_{13}N_2O_2$ | 421 | 3399, 3065, 2987, 2904, 1709, 1659, 1626, 1523, 1502, 1467, 1337, 1296, 1245, 1104, 1019 | 335, 298, 270, 265, 236, 217 |
| 47 | $C_{22}H_{18}N_2O_3$ | 359 | 3420, 3058, 2979, 2930, 1721, 1692, 1625, 1586, 1502, 1468, 1339, 1224, 1107 | 354, 339, 300, 271, 239 |
| 48 | $C_{21}H_{18}N_2O_2$ | 331 | 3197, 3149, 3023, 2934, 1692, 1629, 1590, 1499 | 358, 346, 268, 239, 218, 210 |
| 49 | $C_{19}F_5H_9N_2O_2$ | 393 | 3435, 2900, 1688, 1632, 1597, 1380, 1230, 982, 756 | 351, 338, 261, 239, 215 |

TABLE 13-continued

FAB-MS, IR and UV data of 3,9-disubstituted β-carboline derivatives

| Compd | Formula | FAB-MS m/e (M + 1) | IR (KBr, cm$^{-1}$) | UV$_{\lambda\,max}$ (nm) |
|---|---|---|---|---|
| 50 | $C_{20}H_{14}N_2O_3$ | 331 | 3421, 2986, 1756, 1713, 1628, 1589, 1495, 1366, 1132, 1018 | 353, 265, 241 |
| 51 | $C_{14}H_{14}N_4O$ | 255 | 3298, 3202, 2955, 1666, 1627, 1590, 1531, 1497, 1458, 1331, 1261, 1128 | 359, 343, 303, 272, 238, 221 |
| 52 | $C_{19}H_{16}N_4O$ | 317 | 3349, 3300, 3201, 3059, 1619, 1556, 1496, 1461, 1336, 1200 | 356, 342, 272, 238, 207 |
| 53 | $C_{15}H_{15}N_3O_2$ | 270 | 3435, 3207, 2984, 1727, 1630, 1595, 1472, 1282, 1228, 1079 | 376, 365, 296, 251, 241, 203 |
| 54 | $C_{16}H_{17}N_3O_2$ | 284 | 3420, 3202, 2974, 1721, 1627, 1585, 1532, 1471, 1281, 1219 | 376, 364, 296, 240, 202 |
| 55 | $C_{21}H_{19}N_3O_2$ | 346 | 3248, 3200, 2981, 1722, 1629, 1590, 1534, 1467, 1281, 1217, 1063 | 373, 362, 295, 251 |

TABLE 14

$^1$H-NMR data of 3,9-disubstituted β-carboline derivatives

| Compd | $^1$H-NMR (δ, CDCl$_3$) |
|---|---|
| 26 | 8.94 (1H, s, Ar—H), 8.88 (1H, s, Ar—H), 8.20-8.21 (1H, d, J = 7.5 Hz, Ar—H), 7.65-7.68 (1H, m, Ar—H), 7.50-7.52 (1H, d, J = 8 Hz, Ar—H), 7.36-7.39 (1H, m, J = 8 Hz, Ar—H), 4.06 (3H, s, —OCH$_3$), 4.00 (3H, s, NCH$_3$) |
| 27 | 8.90-9.00 (2H, m, Ar—H), 8.21-8.23 (1H, d, J = 8 Hz, Ar—H), 7.65-7.68 (1H, m, Ar—H), 7.52-7.54 (1H, d, J = 8 Hz, Ar—H), 7.36-7.39 (1H, m, Ar—H), 4.51 (2H, s, NCH$_2$CH$_3$), 4.07 (3H, s, OCH$_3$), 1.52 (3H, s, NCH$_2$CH$_3$) |
| 28 | 8.94 (1H, s, H-4), 8.89 (1H, s, H-1), 8.19-8.21 (1H, d, J = 7 Hz, H-8), 7.62-7.65 (1H, m, H-5), 7.50-7.52 (1H, d, J = 7.5 Hz, H-6), 7.34-7.37 (1H, m, H-7), 4.41-4.44 (2H, m, CH$_2$CH$_2$CH$_2$—CH$_3$), 4.06 (3H, s, OCH$_3$), 1.87-1.93 (2H, m, CH$_2$CH$_2$CH$_2$CH$_3$), 1.35-1.42 (2H, m, CH$_2$CH$_2$—CH$_2$CH$_3$), 0.93-0.96 (3H, m, CH$_2$CH$_2$CH$_2$CH$_3$) |
| 29 | 8.89-8.90 (2H, d, J = 4 Hz, H-4, H-1), 8.21-8.22 (1H, d, J = 8 Hz, H-8), 7.58-7.61 (1H, m, H-5), 7.47-7.48 (1H, d, J = 8.5 Hz, H-6), 7.35-7.38 (1H, m, H-7), 7.24-7.28 (3H, m, Ar—H), 7.13-7.15 (2H, m, Ar—H), 5.60 (2H, s, CH$_2$—Ar), 4.05 (3H, s, OCH$_3$) |
| 30 | 8.94 (1H, s, H-4), 8.86 (1H, s, H-1), 8.19-8.20 (1H, d, J = 7.5 Hz, H-8), 7.66-7.67 (1H, m, H-5), 7.49-7.51 (1H, d, J = 8.5 Hz, H-6), 7.35-7.37 (1H, m, H-7), 4.52-4.56 (2H, m, OCH$_2$CH$_3$), 3.98 (3H, s, NCH$_3$), 1.48-1.51 (3H, s, OCH$_2$CH$_3$) |
| 31 | 8.93 (1H, s, H-4), 8.86 (1H, s, H-1), 8.18-8.21 (1H, d, J = 8 Hz, H-8), 7.62-7.64 (1H, m, H-5), 7.48-7.50 (1H, d, J = 8 Hz, H-6), 7.33-7.36 (1H, m, H-7), 4.42-4.56 (4H, m, OCH$_2$CH$_3$, NCH$_2$CH$_3$), 1.46-1.52 (6H, m, OCH$_2$CH$_3$, NCH$_2$CH$_3$) |
| 32 | 8.98 (1H, s, H-4), 8.89 (1H, s, H-1), 8.21-8.23 (1H, d, J = 8 Hz, H-8), 7.63-7.66 (1H, m, H-5), 7.51-7.53 (1H, d, J = 8.5 Hz, H-6), 7.36-7.38 (1H, m, H-7), 4.52-4.56 (2H, m, OCH$_2$CH$_3$), 4.42-4.44 (2H, m, CH$_2$CH$_2$CH$_2$CH$_3$), 1.88-1.94 (2H, m, CH$_2$CH$_2$CH$_2$CH$_3$), 1.49-1.52 (3H, m, OCH$_2$CH$_3$), 1.35-1.42 (2H, m, CH$_2$CH$_2$CH$_2$CH$_3$), 0.93-0.96 (3H, m, CH$_2$CH$_2$CH$_2$CH$_3$) |
| 33 | 8.91 (2H, m, H-4, H-1), 8.23-8.25 (1H, d, J = 8 Hz, H-8), 7.59-7.62 (1H, m, H-5), 7.49-7.50 (1H, d, J = 8 Hz, H-6), 7.36-7.39 (1H, m, H-7), 7.25-7.27 (3H, s, Ar—H), 7.14-7.16 (2H, m, Ar—H), 5.62 (2H, s, CH$_2$—Ar), 4.51-4.55 (2H, m, —OCH$_2$CH$_3$), 1.47-1.50 (3H, m, OCH$_2$CH$_3$) |
| 34 | 9.19 (1H, s, H-4), 9.12 (1H, s, H-1), 8.42-8.44 (1H, d, J = 8.0 Hz, H-8), 7.81-7.88 (2H, m, H-5, H-6), 7.50-7.53 (1H, m, H-7), 4.16 (1H, s, NCH$_3$) |
| 35 | 9.16 (1H, s, H-4), 8.97 (1H, s, H-1), 8.31-8.33 (1H, d, J = 8.0 Hz, H-8), 7.75-7.81 (2H, m, H-5, H-6), 7.43-7.46 (1H, m, H-7), 4.63-4.67 (1H, s, NCH$_2$CH$_3$), 1.46-1.52 (1H, m, NCH$_2$CH$_3$) |
| 36 | 9.14 (1H, s, H-4), 8.94 (1H, s, H-1), 8.42-8.44 (1H, d, J = 8.0 Hz, H-8), 7.77-7.79 (1H, d, =8.5 Hz, H-5), 7.65-7.68 (1H, m, H-6), 7.34-7.37 (1H, m, H-7), 4.56-4.59 (2H, m, NCH$_2$CH$_2$—CH$_2$CH$_3$), 1.79-1.85 (2H, m, NCH$_2$CH$_2$CH$_2$CH$_3$), 1.28-1.32 (2H, m, NCH$_2$CH$_2$CH$_2$CH$_3$), 0.87-0.90 (3H, m,, NCH$_2$CH$_2$CH$_2$CH$_3$) |
| 37 | 9.15 (1H, s, H-4), 8.96 (1H, s, H-1), 8.44-8.45 (1H, d, J = 8.0 Hz, H-8), 7.79-7.80 (1H, d, J = 8.0 Hz, H-5), 7.63-7.66 (1H, m, H-6), 7.35-7.38 (1H, m, H-7), 7.22-7.31 (5H, m, Ar—H), 5.85 (2H, s, NCH$_2$Ar) |
| 38 | 8.94 (1H, s, H-4), 8.83 (1H, s, H-1), 8.18-8.20 (1H, d, J = 7.5 Hz, H-8), 7.63-7.66 (1H, m, H-5), 7.48-7.50 (1H, d, J = 8.5 Hz, H-6), 7.34-7.37 (1H, m, H-7), 4.46-4.49 (2H, m, OCH$_2$CH$_2$CH$_3$), 3.97 (3H, s, NCH$_3$), 1.84-1.90 (2H, m, J = 7 Hz, OCH$_2$CH$_2$CH$_3$), 1.48-1.56 (2H, m, OCH$_2$CH$_2$CH$_3$), 0.99-1.02 (3H, m, OCH2CH2CH2CH3) |
| 39 | 9.02 (1H, s, H-4), 8.86 (1H, s, H-1), 8.20-8.22 (1H, d, J = 8 Hz, H-8), 7.63-7.67 (1H, m, H-5), 7.51-7.53 (1H, d, J = 7.5 Hz, H-6), 7.35-7.38 (1H, m, H-7), 4.47-4.51 (4H, m, OCH$_2$CH$_2$CH$_3$, NCH$_2$CH$_3$), 1.84-1.90 (2H, m, OCH$_2$CH$_2$CH$_3$), 1.49-1.56 (2H, m, OCH$_2$CH$_2$CH$_3$), 0.99-1.02 (3H, m, OCH$_2$CH$_2$CH$_3$) |
| 40 | 8.95 (1H, s, H-4), 8.85 (1H, s, H-1), 8.19-8.20 (1H, d, J = 7 Hz, H-8), 7.60-7.64 (1H, m, H-5), 7.49-7.50 (1H, d, J = 8.5 Hz, H-6), 7.32-7.36 (1H, m, H-7), 4.47-4.49 (2H, m, OCH$_2$CH$_2$CH$_3$), 4.37-4.42 (2H, m, NCH$_2$CH$_2$CH$_3$), 1.84-1.92 (4H, m, OCH$_2$CH$_2$CH$_2$CH$_3$, NCH$_2$CH$_2$CH$_3$), 1.49-1.56 (2H, m, OCH$_2$CH$_2$CH$_2$CH$_3$), 1.34-1.40 (2H, m, NCH$_2$CH$_2$CH$_3$), 0.99-1.02 (3H, m, NCH$_2$CH$_2$CH$_3$), 0.92-0.95 (3H, m, NCH$_2$CH$_2$CH$_3$) |
| 41 | 8.89 ((1H, s, H-4), 8.85 (1H, s, H-1), 8.19-8.20 (1H, d, J = 8 Hz, H-8), 7.56-7.59 (1H, m, H-5), 7.45-7.46 (1H, d, J = 8.5 Hz, H-6), 7.33-7.36 (1H, m, H-7), 7.22-7.26 (3H, m, Ar—H), 7.11-7.13 (2H, m, Ar—H), 5.56 (2H, s, —CH$_2$—Ar), 4.45-4.48 (2H, m, —OCH$_2$CH$_2$CH$_3$), 1.82-1.88 (2H, m, —OCH$_2$CH$_2$CH$_3$), 1.47-1.54 (2H, m, OCH$_2$CH$_2$CH$_3$), 0.98-1.01 (3H, m, OCH$_2$CH$_2$CH$_3$) |
| 42 | 8.73 (1H, s, H-4), 8.13-8.15 (1H, d, J = 8 Hz, H-1), 7.96 (1H, s, H-8), 7.54-7.58 (1H, m, H-5), 7.41-7.43 (1H, d, J = 8.5 Hz, H-6), 7.28-7.31 (1H, m, H-7), 7.23-7.27 (3H, m, Ar—H), 7.11-7.12 (2H, m, Ar—H), 5.51 (2H, s, CH$_2$Ar), 4.94 (2H, s, CH$_2$OH), 4.01 (1H, s, CH$_2$OH) |
| 43 | 9.01 (1H, s, H-4), 8.30-8.31 (1H, d, J = 8 Hz, H-1), 8.20 (1H, s, H-8), 7.73-7.75 (1H, d, J = 8.5 Hz, H-5), 7.58-7.61 (1H, m, H-6), 7.19-7.31 (6H, m, H-7, Ar—H), 5.76 (2H, s, NCH$_2$Ar), 5.28 (2H, s, CH$_2$), 2.11 (3H, s, CH$_3$) |
| 44 | 8.96 (1H, s, H-4), 8.91 (1H, s, H-1), 8.22-8.24 (1H, m, H-8), 7.60-7.64 (1H, m, H-5), 7.49-7.55 (3H, m, H-6, H-7, Ar—H), 7.31-7.40 (4H, m, Ar—H), 7.25-7.29 (3H, m, Ar—H), 7.12-7.14 (2H, m, Ar—H), 5.63 (2H, s, OCH$_2$Ar), 5.52 (2H, s, NCH$_2$Ar) |
| 45 | 8.89 (2H, m, H-4, H-1), 8.20-8.22 (1H, d, J = 7.5 Hz, H-8), 7.61-7.64 (1H, m, H-5), 7.41-7.42 (1H, m, H-6), 7.34-7.37 (1H, m, H-7), |

TABLE 14-continued

¹H-NMR data of 3,9-disubstituted β-carboline derivatives

| Compd | ¹H-NMR (δ, CDCl₃) |
|---|---|
|  | 7.26-7.30 (2H, m, Ar—H), 7.19-7.22 (1H, m, Ar—H), 7.13-7.15 (2H, m, Ar—H), 4.52-4.57 (2H, m, NCH₂CH₂CH₂Ar), 4.41-4.44 (2H, m, NCH₂CH₂CH₂Ar), 2.70-2.73 (2H, m, OCH₂CH₃), 2.24-2.30 (2H, m, NCH₂CH₂CH₂Ar)1.49-1.52 (3H, m, OCH₂CH₃) |
| 46 | 9.07 (1H, s, H-4), 8.86 (1H, s, H-1), 8.19-8.21 (1H, d, J = 8 Hz, H-8), 7.65-7.68 (1H, m, H-5), 7.59-7.61 (1H, d, J = 8.5 Hz, H-6), 7.38-7.41 (1H, m, H-7), 5.67 (2H, s, CH₂—Ar), 4.52-4.56 (2H, m, OCH₂CH₃), 1.49-1.51 (3H, m, OCH₂CH₃) |
| 47 | 8.73 (1H, s, H-4), 8.68 (1H, s, H-1), 8.18-8.19 (1H, d, J = 7.5 Hz, H-8), 7.52-7.55 (1H, m, H-5), 7.11-7.42 (7H, m, H-6, H-7, Ar—H), 5.51-5.55 (2H, s, CH₂COAr), 4.24-4.28 (2H, m, OCH₂CH₃), 1.25-1.31 (3H, m, OCH₂CH₃) |
| 48 | 9.13 (1H, s, H-4), 9.00 (1H, s, H-1), 8.46-8.48 (1H, d, J = 7.5 Hz, H-8), 7.76-7.78 (1H, d, J = 8.0 Hz, H-5), 7.69-7.72 (1H, m, H-6), 7.38-7.41 (1H, m, H-7), 7.21-7.26 (2H, m, Ar—H), 7.13-7.17 (3H, m, Ar—H), 4.63-4.66 (2H, m, NCH₂CH₂CH₂Ar), 2.49-2.51 (2H, m, NCH₂CH₂CH₂Ar), 2.14-2.20 (2H, m, NCH₂CH₂CH₂Ar) |
| 49 | 8.11-8.13 (1H, m, H-4), 8.00-8.02 (2H, m, H-1, H-8), 7.69-7.73 (1H, m, H-5), 7.69-7.72 (1H, m, H-6), 7.38-7.41 (1H, m, H-7), 7.21-7.26 (2H, m, Ar—H), 7.13-7.17 (3H, m, Ar—H), 4.63-4.66 (2H, m, NCH₂CH₂CH₂Ar), |
| 50 | 9.28 (1H, s, H-4), 9.16 (1H, s, H-1), 8.57-8.58 (1H, d, J = 7.5 Hz, H-8), 8.16-8.18 (2H, d, J = 8.5 Hz, H-5, H-6), 7.64-7.81 (5H, m, H-7, Ar—H), 7.43-7.46 (1H, m, Ar—H), 6.45 (2H, s, NCH₂—COAr) |
| 51 | 9.61 (1H, s, NH), 9.03 (1H, s, H-4), 8.82 (1H, s, H-1), 8.40-8.42 (1H, d, J = 7.5 Hz, H-8), 7.75-7.76 (1H, d, J = 8.5 Hz, H-5), 7.64-7.67 (1H, m, H-6), 7.32-7.35 (1H, m, H-7), 4.58-4.62 (2H, m, NCH₂CH₃), 4.54 (2H, s, NH₂), 1.37-1.40 (3H, m, NCH₂CH₃) |
| 52 | 9.62 (1H, s, NH), 9.04 (1H, s, H-4), 8.85 (1H, s, H-1), 8.43-8.45 (1H, d, J = 8 Hz, H-8), 7.77-7.79 (1H, d, J = 8.5 Hz, H-5), 7.61-7.65 (1H, m, H-6), 7.33-7.36 (1H, m, H-7), 7.21-7.30 (5H, m, ArH), 5.83 (2H, s, NCH₂Ar), 4.53-4.54 (2H, s, NH₂) |
| 53 | 8.67 (1H, s, H-4), 8.55 (1H, s, H-1), 8.16-8.17 (1H, d, J = 8 Hz, H-8), 7.56-7.59 (1H, m, H-5), 7.40-7.42 (1H, d, J = 8 Hz, H-6), 7.23-7.26 (1H, m, H-7), 4.37-4.41 (2H, m, NCH₂CH₃), 3.87 (3H, s, OCH₃)1.45-1.48 (3H, m, NCH₂CH₃) |
| 54 | 8.68 (1H, s, H-4), 8.59 (1H, s, H-1), 8.15-8.17 (1H, d, J = 8 Hz, H-8), 7.55-7.59 (1H, m, H-5), 7.39-7.40 (1H, d, J = 8.5 Hz, H-6), 7.23-7.26 (1H, m, H-7), 4.32-4.38 (4H, m, NCH₂CH₃, OCH₂CH₃), 1.41-1.47 (6H, m, NCH₂CH₃, OCH₂CH₃) |
| 55 | 8.88 (1H, s, H-4), 8.78 (1H, s, H-1), 8.21-8.22 (1H, d, J = 7.5 Hz, H-8), 8.06-8.08 (2H, d, J = 8 Hz, H-5, H-6), 7.67-7.70 (1H, m, H-7), 7.54-7.60 (3H, m, Ar—H), 7.35-7.38 (1H, m, Ar—H), 7.31-7.32 (1H, d, d = 8 Hz, Ar—H), 5.79 (2H, s, NCH₂—Ar), 4.51-4.55 (2H, m, OCH₂CH₃), 1.47-1.50 (3H, m, OCH₂CH₃) |

Synthesis of 1,3,9-trisubstituted β-carboline derivatives

Experimental Instruments and Reagents

The experimental instruments and reagents are as described above.

Synthetic Route and Operational Steps

Scheme I

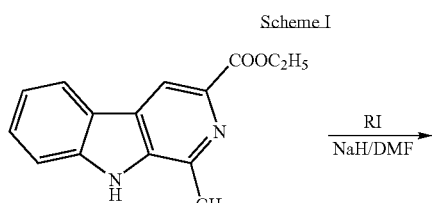

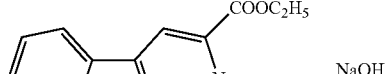

56 R = CH₃
57 R = CH₂CH₃
58 R = CH₂

59 R = (CH₂)₃—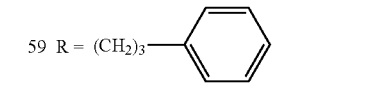

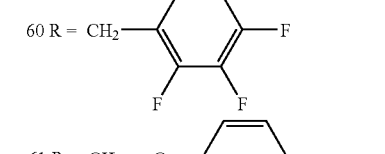

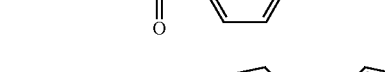

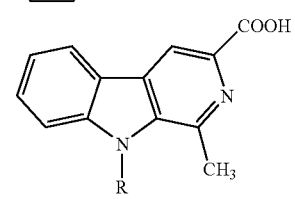

62 R = CH₃
63 R = CH₂CH₃
64 R = CH₂

65 R = (CH₂)₃—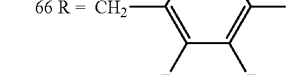

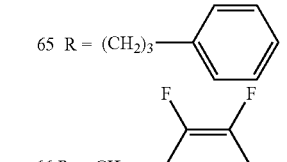

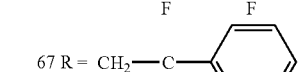

Example 84

General procedure for the preparation of 9-substituted-1-methyl-β-carboline-3-carboxylates Ethyl 1-methyl-β-carboline-3-carboxylate (10 mmol) was mixed with DMF (50 ml) and stirred at room temperature until the solution became clear. 60% NaH (50 mmol) was added and stirred for 5 minutes. Alkene halide or aromatics (50 mmol) was added. The mixture was reacted at room temperature or refluxed. TLC track measurement was conducted. After the reaction was finished, the reaction mixture was poured into cold water, extracted with ethyl acetate, washed with water and brine, dried, decolorized with activated carbon, filtered and evaporated in reduced pressure, and the residue was dissolved in 50 ml anhydrous ethanol. The pH was adjusted to 3-4 with concentrated HCl. After concentra-

Example 85

Synthesis of ethyl 1,9-dimethyl-β-carboline-3-carboxylate (56)

white crystals (2.2 g, 82%) were obtained, mp 141-142° C.

Example 86

Synthesis of ethyl 9-ethyl-1-methyl-β-carboline-3-carboxylate (57)

white crystals (2.3 g, 81%) were obtained, mp 96-98° C.

Example 87

Synthesis of ethyl 9-benzyl-1-methyl-β-carboline-3-carboxylate (58)

Compound 10 (2.54 g, 10 mmol) was mixed with DMF (50 ml) and stirred at room temperature until the solution became clear. 60% NaH (1.2 g) was added and stirred for 5 minutes. Benzyl bromide (6 ml) was added. TLC Track measurement with was conducted. The mixture was reacted at room temperature for 12 h. After the reaction was finished, the reaction mixture was poured into cold water, and extracted with ethyl acetate, washed with water and brine, dried, decolorized with activated carbon, evaporated. The residue was dissolved in 50 ml anhydrous ethanol. The pH of the solution was adjusted to 3-4 by introducing dry hydrogen chloride gas. After concentration, recrystallization with acetone/ethyl ether and filtration, hydrochloride salts was afforded, and 100 ml water was added. After neutralizing by sodium bicarbonate, extracting by ethyl acetate, drying over anhydrous sodium sulfate, decolorizing with activated carbon, filtration, concentration, purifying with silica gel column chromatography with ethyl acetate as eluent. Upon recrystallization, white crystals (2.5 g, 73%) was obtained, mp 155-156° C.

Example 88

Synthesis of ethyl 9-phenylpropyl-1-methyl-β-carboline-3-carboxylate (59)

Compound 10 (2.54 g, 10 mmol) was mixed with DMF (50 ml) and stirred at room temperature until the solution became clear. 60% NaH (1.2 g) was added and stirred for 5 minutes, followed by the addition of 1-bromine-3-phenyl propane (10 ml), and TLC track measurement. The mixture was reacted at room temperature for about 15 h. The subsequent steps were conducted according to those for synthesizing compound 58. Finally, white crystals (2.8 g, 75%) were obtained, mp 101-102° C.

Example 89

Synthesis of ethyl 9-(2',3',4',5',6'-pentafluoro)benzyl-1-methyl-β-carboline-3-carboxylate (60)

Compounds 10 (1.3 g, 10 mmol) was mixed with DMF (50 ml), and was stirred at room temperature until the mixture became clear. The mixture was added 60% NaH (1.2 g) and stirred for 5 minutes followed by the addition of α-bromine-2,3,4,5,6-pentafluorobenzyl (2 ml) and TLC track measurement. The mixture was reacted at room temperature for about 1 hour. The subsequent steps were conducted according to those for synthesizing compound 58 to afford white block crystals (1.5 g, 68%), mp 145-146° C.

Example 90

Synthesis of ethyl 9-acetophenone-1-methyl-β-carboline-3-carboxylate (61)

Afforded white solids (1.6 g, 43%), mp was 219-220° C.

Example 91

Synthesis of ethyl 1-propyl-9-methyl-β-carboline-3-carboxylate (68)

white crystals (2.2 g, 74%) were obtained, mp 108-109° C.

Example 92

Synthesis of ethyl 1-propyl-9-ethyl-β-carboline-3-carboxylate (69)

white crystals (2.0 g, 65%) were obtained, mp 86-87° C.

Example 93

Synthesis of ethyl 9-benzyl-1-propyl-β-carboline-3-carboxylate (70)

white crystals (1.8 g, 64%) were obtained, mp 158-159° C.

Example 94

Synthesis of ethyl 9-phenylpropyl-1-propyl-β-carboline-3-carboxylate (71)

white crystals (1.7 g, 57%) were obtained, mp 92-93° C.

Example 95

Synthesis of methyl 1-phenyl-9-methyl-β-carboline-3-carboxylate (76)

white crystals (2.4 g, 76%) were obtained, mp 205-207° C.

Example 96

Synthesis of methyl 1-phenyl-9-ethyl-β-carboline-3-carboxylate (77)

white crystals (2.3 g, 69%) were obtained, mp 169-170° C.

51

Scheme II

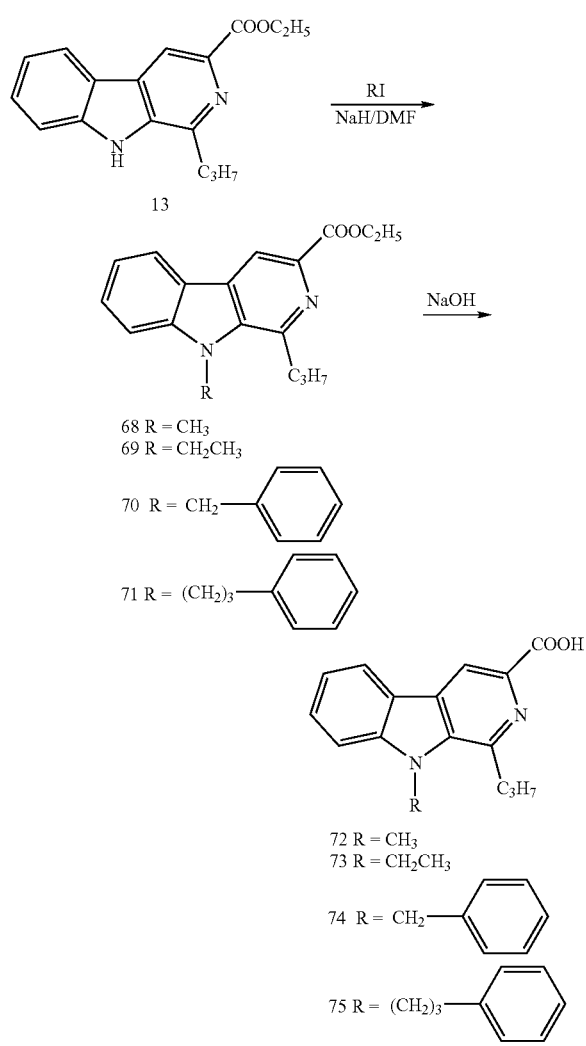

68 R = CH₃
69 R = CH₂CH₃
70 R = CH₂—Ph
71 R = (CH₂)₃—Ph

72 R = CH₃
73 R = CH₂CH₃
74 R = CH₂—Ph
75 R = (CH₂)₃—Ph

Example 97

General procedure for the preparation of 1,9-substituted-β-carboline-3-carboxylic acids 1,9-Disubstituted-β-carboline-3-carboxylate (10 mmol), water (100 ml), ethanol (50 ml) and NaOH (50 mmol) were mixed and refluxed by heating for 2 h. And the ethanol was removed under reduced pressure. The mixture was neutralized (pH 5) with 5M HCl and cooled. The precipitate was collected, washed well with water and dried. Examples 98 to 109 were conducted according to the operational steps as mentioned above.

Example 98

Synthesis of 1,9-dimethyl-β-carboline-3-carboxylic acid (62)

yellow solids (0.58 g, 97%) were obtained, mp 262-264° C.

52

Example 99

Synthesis of 9-ethyl-1-methyl-β-carboline-3-carboxylic acid (63)

yellow solids (0.62 g, 97%) were obtained, mp 243-245° C.

Example 100

Synthesis of 9-benzyl-1-methyl-β-carboline-3-carboxylic acid (64)

yellow solids (0.78 g, 98%) were obtained, mp 246-248° C.

Example 101

Synthesis of 9-phenylpropyl-1-methyl-β-carboline-3-carboxylic acid (65)

yellow solids (0.84 g, 97%) were obtained, mp 186-188° C.

Example 102

Synthesis of 9-(2',3',4',5',6'-pentafluoro)benzyl-1-methyl-β-carboline-3-carboxylic acid (66)

gray solids (11.0 g, 98%) were obtained, mp 191-193° C.

Scheme III

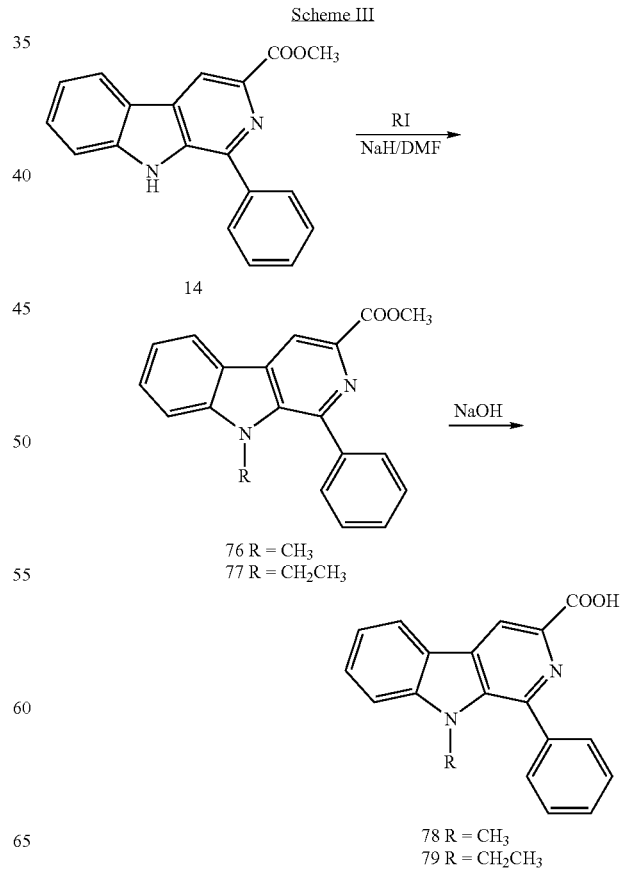

76 R = CH₃
77 R = CH₂CH₃

78 R = CH₃
79 R = CH₂CH₃

Example 103

Synthesis of 9-acetophenone-1-methyl-β-carboline-3-carboxylic acid (67)

white solids (0.84 g, 98%) were obtained, mp>270° C.

Example 104

Synthesis of 9-methyl-1-propyl-β-carboline-3-carboxylic acid (72)

yellow solids (0.52 g, 97%) were obtained, mp 181-183° C.

Example 105

Synthesis of 1-propyl-9-ethyl-β-carboline-3-carboxylic acid (73)

yellow solids (0.54 g, 96%) were obtained, mp 189-191° C.

Example 106

Synthesis of 9-benzyl-1-propyl-β-carboline-3-carboxylic acid (74)

yellow solids (0.66 g, 96%) were obtained, mp 193-194° C.

Example 107

Synthesis of 9-phenylpropyl-1-propyl-β-carboline-3-carboxylic acid (75)

yellow solids (0.72 g, 97%) were obtained, mp 223-224° C.

Example 108

Synthesis of 9-methyl-1-phenyl-β-carboline-3-carboxylic acid (78)

Afforded light yellow solids (0.74 g, 98%), mp 223-224° C.

Example 109

Synthesis of 9-ethyl-1-phenyl-β-carboline-3-carboxylic acid (79)

Afforded light yellow solids (0.77 g, 97%), mp 194-195° C.

Physico-Chemical Properties of, TLC and Spectra Analyses of 1,3,9-Trisubstituted β-Carboline Derivatives

TABLE 15

Physico-chemical data of 1,3,9-substituted β-carboline derivatives

| Compd | Formula | FW | Yield (%) | Appearance | Solubility | Mp (° C.) |
|---|---|---|---|---|---|---|
| 56 | $C_{16}H_{16}N_2O_2$ | 268 | 82 | white crystals | soluble in alcohols, ethers, chloroform etc. | 141-142 |
| 57 | $C_{17}H_{18}N_2O_2$ | 282 | 81 | white crystals | soluble in alcohols, ethers, chloroform etc. | 96-98 |
| 58 | $C_{22}H_{20}N_2O_2$ | 344 | 73 | white crystals | soluble in alcohols, ethers, chloroform etc. | 155-156 |
| 59 | $C_{24}H_{24}N_2O_2$ | 372 | 75 | white crystals | soluble in alcohols, ethers, chloroform etc. | 101-102 |
| 60 | $C_{22}F_5H_{15}N_2O_2$ | 434 | 68 | ash gray crystals | soluble in alcohols, ethers, chloroform etc. | 145-146 |
| 61 | $C_{23}H_{20}N_2O_3$ | 372 | 43 | white flocculent solids | soluble in alcohols, ethers, esters, chloroform etc. | 219-220 |
| 62 | $C_{14}H_{12}N_2O_2$ | 240 | 97 | light yellow solids | soluble in alcohols and DMSO | 262-264 |
| 63 | $C_{15}H_{14}N_2O_2$ | 254 | 97 | light yellow solids | soluble in alcohols and DMSO | 243-245 |
| 64 | $C_{20}H_{16}N_2O_2$ | 316 | 98 | light yellow solids | soluble in DMSO | 246-248 |
| 65 | $C_{22}H_{20}N_2O_2$ | 344 | 97 | light yellow solids | soluble in DMSO | 186-188 |
| 66 | $C_{20}F_5H_{11}N_2O_2$ | 406 | 97 | ash gray solids | soluble in DMSO | 191-193 |
| 67 | $C_{21}H_{16}N_2O_3$ | 344 | 98 | white solids | soluble in DMSO | >270 |
| 68 | $C_{18}H_{20}N_2O_2$ | 296 | 74 | white crystals | soluble in alcohols, ethers, esters, chloroform etc. | 119-110 |

TABLE 15-continued

Physico-chemical data of 1,3,9-substituted β-carboline derivatives

| Compd | Formula | FW | Yield (%) | Appearance | Solubility | Mp (° C.) |
|---|---|---|---|---|---|---|
| 69 | $C_{19}H_{22}N_2O_2$ | 310 | 65 | white crystals | soluble in alcohols, ethers, esters, chloroform etc. | 86-87 |
| 70 | $C_{24}H_{24}N_2O_2$ | 372 | 64 | white crystals | soluble in alcohols, ethers, esters, chloroform etc. | 158-159 |
| 71 | $C_{26}H_{28}N_2O_2$ | 400 | 57 | white crystals | soluble in alcohols, ethers and esters | 92-93 |
| 72 | $C_{16}H_{16}N_2O_2$ | 268 | 97 | light yellow solids | soluble in alcohols and DMSO | 181-183 |
| 73 | $C_{17}H_{18}N_2O_2$ | 282 | 96 | light yellow solids | soluble in alcohols and DMSO | 189-191 |
| 74 | $C_{22}H_{19}N_2O_2$ | 344 | 96 | light yellow solids | soluble in DMSO | 193-194 |
| 75 | $C_{24}H_{23}N_2O_2$ | 372 | 97 | light yellow solids | Soluble in DMSO | 176-178 |
| 76 | $C_{20}H_{16}N_2O_2$ | 316 | 76 | white crystals | soluble in alcohols, ethers, esters, chloroform etc. | 205-207 |
| 77 | $C_{21}H_{18}N_2O_2$ | 330 | 69 | white crystals | soluble in alcohols, ethers, esters, chloroform etc. | 169-170 |
| 78 | $C_{19}H_{14}N_2O_2$ | 302 | 98 | white solids | soluble in DMSO | 223-234 |
| 79 | $C_{20}H_{16}N_2O_2$ | 316 | 97 | white solids | soluble in DMSO | 194-195 |

TABLE 16

FAB-MS, IR and UV data of 1,3,9-trisubstituted β-carboline derivatives

| Compd | Formula | FAB-MS m/e (M + 1) | IR (KBr, cm$^{-1}$) | UV ($\lambda_{max}$, nm) |
|---|---|---|---|---|
| 56 | $C_{16}H_{16}N_2O_2$ | 269 | 3044, 2978, 2903, 1713, 1620, 1557, 1456, 1369, 1249, 1215, 1138, 1030 | 354, 338, 307, 272, 239 |
| 57 | $C_{17}H_{18}N_2O_2$ | 283 | 3359, 3057, 2974, 2931, 2902, 1687, 1620, 1556, 1449, 1368, 1342, 1275, 1243, 1133, 1026 | 354, 338, 307, 273, 240 |
| 58 | $C_{22}H_{20}N_2O_2$ | 345 | 3441, 3059, 2967, 2929, 1694, 1622, 1561, 1455, 1342, 1272, 1238, 1136, 1029 | 351, 337, 305, 272, 239 |
| 59 | $C_{24}H_{24}N_2O_2$ | 373 | 3059, 2977, 2930, 2852, 1694, 1620, 1557, 1454, 1366, 1341, 1257, 1135, 1028 | 355, 339, 308, 273, 240, 220 |
| 60 | $C_{22}F_5H_{15}N_2O_2$ | 435 | 3398, 2974, 2931, 1708, 1629, 1503, 1454, 1341, 1268, 1122, 1033 | 346, 332, 301, 271, 265, 238 |
| 61 | $C_{23}H_{20}N_2O_3$ | 373 | 3063, 3041, 2998, 1665, 1595, 1447, 1330, 1219, 1018, 711 | 250 |
| 62 | $C_{14}H_{12}N_2O_2$ | 241 | 3558, 3332, 2250-3250, 1936, 1712, 1621, 1344, 1215, 1050 | 355, 340, 269, 239 |
| 63 | $C_{15}H_{14}N_2O_2$ | 255 | 3393, 2250-3250, 1714, 1621, 1589, 1366, 1233, 1130, 1053 | 355, 270, 240, 223 |
| 64 | $C_{20}H_{16}N_2O_2$ | 317 | 2250-3750, 1720, 1615, 1340, 1206 | 352, 338, 268, 239 |
| 65 | $C_{22}H_{20}N_2O_2$ | 345 | 3417, 2500-3250, 1740, 1624, 1591, 1355, 1061 | 356, 269, 240 |
| 66 | $C_{20}F_5H_{11}N_2O_2$ | 407 | 3422, 2250-3250, 1754, 1652, 1625, 1592, 1491, 1360, 1131, 1017 | 349, 336, 268, 238 |
| 67 | $C_{21}H_{16}N_2O_3$ | 345 | 2250-3500, 1667, 1626, 1370, 1104 | 345, 334, 265, 239, 216 |
| 68 | $C_{18}H_{20}N_2O_2$ | 297 | 2957, 2868, 1703, 1555, 1466, 1367, 1263, 1135, 1053, 739 | 354, 339, 307, 272, 240 |

TABLE 16-continued

FAB-MS, IR and UV data of 1,3,9-trisubstituted β-carboline derivatives

| Compd | Formula | FAB-MS m/e (M + 1) | IR (KBr, cm$^{-1}$) | UV ($\lambda_{max}$, nm) |
|---|---|---|---|---|
| 69 | C$_{19}$H$_{22}$N$_2$O$_2$ | 311 | 3052, 2960, 2868, 1694, 1555, 1446, 1344, 1243, 1132 | 355, 340, 307, 273, 240 |
| 70 | C$_{24}$H$_{24}$N$_2$O$_2$ | 373 | 3430, 2960, 2934, 2868, 1727, 1619, 1556, 1462, 1339, 1259, 1223, 1147, 1052 | 352, 337, 304, 272, 240 |
| 71 | C$_{26}$H$_{28}$N$_2$O$_2$ | 401 | 3068, 2994, 2968, 2929, 2870, 1701, 1620, 1556, 1450, 1365, 1258, 1132, 1058 | 355, 339, 307, 273, 241, 201 |
| 72 | C$_{16}$H$_{16}$N$_2$O$_2$ | 269 | 3142, 3059, 2960, 2869, 1739, 1620, 1582, 1470, 1359, 1248, 1128 | 356, 342, 269, 240 |
| 73 | C$_{17}$H$_{18}$N$_2$O$_2$ | 283 | 3191, 2965, 2871, 1745, 1619, 1558, 1456, 1354, 1228, 1120 | 356, 342, 268, 240 |
| 74 | C$_{22}$H$_{19}$N$_2$O$_2$ | 345 | 3064, 2957, 2923, 2866, 1752, 1643, 1589, 1456, 1353, 1209, 1130 | 353, 339, 268, 240 |
| 75 | C$_{24}$H$_{23}$N$_2$O$_2$ | 373 | 3163, 3068, 2963, 2933, 1745, 1620, 1583, 1460, 1362, 1245, 1088 | 356, 343, 269, 240 |
| 76 | C$_{20}$H$_{16}$N$_2$O$_2$ | 317 | 3426, 3051, 2944, 1723, 1622, 1557, 1493, 1435, 1356, 1262, 1223, 1129 | 360, 346, 309, 275, 233 |
| 77 | C$_{21}$H$_{18}$N$_2$O$_2$ | 331 | 3429, 3054, 2980, 1724, 1621, 1556, 1429, 1351, 1247, 1133, 1051 | 360, 345, 309, 275, 234 |
| 78 | C$_{19}$H$_{14}$N$_2$O$_2$ | 303 | 2000-3250, 1754, 1681, 1622, 1557, 1392, 1262, 1051 | 360, 273, 237 |
| 79 | C$_{20}$H$_{16}$N$_2$O$_2$ | 317 | 3283, 2974, 1730, 1620, 1559, 1451, 1355, 1299 | 360, 273, 239 |

TABLE 17

$^1$H-NMR data of 1,3,9-trisubstituted β-carboline derivatives

| Compd | $^1$H-NMR (δ, DMSO) |
|---|---|
| 56 | 8.71 (1H, s, H-4), 8.14-8.16 (1H, d, J = 8 Hz, H-8), 7.60-7.63 (1H, m, H-5), 7.45-7.47 (1H, d, J = 8.5 Hz, H-6), 7.31-7.34 (1H, m, H-7), 4.50-4.54 (2H, m, OCH$_2$CH$_3$), 4.16 (3H, s, NCH$_3$), 3.15 (3H, s, CH$_3$), 1.48-1.50 (3H, m, OCH$_2$CH$_3$) |
| 57 | 8.74 (1H, s, H-4), 8.16-8.18 (1H, d, J = 7.5 Hz, H-8), 7.60-7.63 (1H, m, H-5), 7.48-7.50 (1H, d, J = 8.5 Hz, H-6), 7.31-7.35 (1H, m, H-7), 4.62-4.66 (2H, m, NCH$_2$CH$_3$), 4.50-4.55 (2H, m, OCH$_2$CH$_3$), 3.13 (3H, s, CH$_3$), 1.46-1.50 (6H, m, NCH$_2$CH$_3$, OCH$_2$CH$_3$) |
| 58 | 8.80 (1H, s, H-4), 8.22-8.23 (1H, d, J = 7.5 Hz, H-8), 7.55-7.58 (1H, m, H-5), 7.40-7.41 (1H, d, J = 8.5 Hz, H-6), 7.34-7.37 (1H, m, H-7), 7.24-7.28 (3H, m, Ar—H), 6.94-6.96 (2H, m, Ar—H), 5.85 (2H, s, NCH$_2$Ar), 4.50-4.54 (2H, m, OCH$_2$CH$_3$), 2.96 (3H, s, CH$_3$), 1.47-1.50 (3H, m, OCH$_2$CH$_3$) |
| 59 | 8.73 (1H, s, H-4), 8.15-8.17 (1H, d, J = 7.5 Hz, H-8), 7.56-7.59 (1H, m, H-5), 7.18-7.35 (7H, m, H-6, H-7, Ar—H), 4.49-4.58 (4H, m, OCH$_2$CH$_3$, NCH$_2$CH$_2$CH$_2$Ar), 2.97 (3H, s, CH$_3$), 2.74-2.77 (2H, m, NCH$_2$CH$_2$CH$_2$Ar), 2.14-2.20 (2H, m, NCH$_2$CH$_2$CH$_2$Ar), 1.47-1.50 (3H, m, OCH$_2$CH$_3$) |
| 60 | 8.75 (1H, s, H-4), 8.17-8.19 (1H, d, J = 8.5 Hz, H-8), 7.56-7.59 (1H, m, H-5), 7.34-7.38 (2H, m, H-6, H-7), 5.99 (2H, s, NCH$_2$Ar), 4.51-4.56 (2H, m, OCH$_2$CH$_3$), 3.16 (3H, s, CH$_3$), 1.48-1.51 (3H, m, OCH$_2$CH$_3$) |
| 62 | 8.89 (1H, s, H-4), 8.44-8.45 (1H, d, J = 8 Hz, H-8), 7.82-7.83 (1H, d, J = 8.5 Hz, H-5), 7.70-7.73 (1H, m, H-6), 7.37-7.40 (1H, m, H-7), 4.50-4.54 (3H, s, NCH$_3$), 3.18 (3H, s, CH$_3$) |
| 63 | 8.89 (1H, s, H-4), 8.45-8.46 (1H, d, J = 7.5 Hz, H-8), 7.83-7.85 (1H, d, J = 8.5 Hz, H-5), 7.70-7.73 (1H, m, H-6), 7.37-7.41 (1H, m, H-7), 4.72-4.76 (2H, m, NCH$_2$CH$_3$), 3.14 (3H, s, CH$_3$), 1.40-1.42 (3H, m, NCH$_2$CH$_3$) |
| 64 | 8.80 (1H, s, H-4), 8.31-8.35 (1H, d, J = 7.5 Hz, H-8), 7.65-7.68 (1H, d, J = 8.0 Hz, H-5), 7.58-7.60 (1H, m, H-6), 7.15-7.30 (6H, m, H-7, Ar—H), 5.78 (2H, m, NCH$_2$Ar), 2.95 (3H, s, CH$_3$) |
| 65 | 8.75 (1H, s, H-4), 8.36-8.37 (1H, d, J = 7.5 Hz, H-8), 7.68-7.69 (1H, d, J = 8.0 Hz, H-5), 7.61-7.64 (1H, m, H-6), 7.18-7.34 (6H, m, H-7, Ar—H), 4.64-4.67 (2H, m, NCH$_2$CH$_2$Ar), 2.90 (3H, s, CH$_3$), 2.73-2.76 (2H, m, CH$_2$CH$_2$CH$_2$Ar), 2.06-2.12 (2H, m, NCH$_2$CH$_2$Ar) |
| 66 | 8.80 (1H, s, H-4), 8.40-8.42 (1H, d, J = 8.0 Hz, H-8), 7.62-7.64 (2H, m, H-5, H-6), 7.34-7.37 (1H, m, H-7), 6.10 (2H, s, NCH$_2$Ar), 3.01-3.02 (3H, s, CH$_3$) |
| 68 | 8.69 (1H, s, H-4), 8.14-8.16 (1H, d, J = 8 Hz, H-8), 7.59-7.62 (1H, m, H-5), 7.46-7.47 (1H, d, J = 8.5 Hz, H-6), 7.30-7.33 (1H, m, H-7), 4.49--4.53 (2H, m, OCH$_2$CH$_3$), 4.11 (3H, s, NCH$_3$), 3.36-3.39 (2H, m, CH$_2$CH$_2$—CH$_3$), 1.87-1.92 (2H, m, CH$_2$CH$_2$CH$_3$), 1.46-1.49 (3H, m, OCH$_2$CH$_3$), 1.09-1.12 (3H, m, CH$_2$CH$_2$CH$_3$) |
| 69 | 8.73 (1H, s, H-4), 8.18-8.19 (1H, d, J = 8 Hz, H-8), 7.60-7.63 (1H, m, H-5), 7.50-7.52 (1H, d, J = 8.5 Hz, H-6), 7.32-7.35 (1H, m, H-7), 4.49-4.62 (4H, m, NCH$_2$CH$_3$, OCH$_2$CH$_3$), 3.30-3.34 (2H, m, CH$_2$—CH$_2$CH$_3$), 1.87-1.95 (2H, m, CH$_2$CH$_2$CH$_3$), 1.45-1.49 (6H, m, NCH$_2$CH$_3$, OCH$_2$CH$_3$), 1.10-1.13 (3H, m, CH$_2$CH$_2$CH$_3$) |

TABLE 17-continued

$^1$H-NMR data of 1,3,9-trisubstituted β-carboline derivatives

| Compd | $^1$H-NMR (δ, DMSO) |
|---|---|
| 70 | 8.78 (1H, s, H-4), 8.22-8.24 (1H, d, J = 8 Hz, H-8), 7.55-7.58 (1H, m, H-5), 7.41-7.42 (1H, d, J = 8.5 Hz, H-6), 7.34-7.37 (1H, m, H-7), 7.23-7.30 (3H, m, Ar—H), 6.94-6.95 (2H, m, Ar—H), 5.79 (2H, s, NCH$_2$Ar), 4.49-4.54 (2H, m, OCH$_2$CH$_3$), 3.12-3.16 (2H, m, CH$_2$CH$_2$CH$_3$), 1.78-1.84 (2H, m, CH$_2$CH$_2$CH$_3$), 1.46-1.52 (3H, m, OCH$_2$CH$_3$), 0.96-1.01 (3H, m, CH$_2$CH$_2$CH$_3$) |
| 71 | 8.71 (1H, s, H-4), 8.15-8.17 (1H, d, J = 8 Hz, H-8), 7.55-7.59 (1H, m, H-5), 7.34-7.36 (1H, d, J = 8.5 Hz, H-6), 7.29-7.32 (3H, m, H-7, Ar—H), 7.18-7.25 (3H, m, Ar—H), 4.46-4.53 (4H, m, NCH$_2$CH$_2$CH$_2$Ar, OCH$_2$CH$_3$), 3.15-3.18 (2H, m, CH$_2$CH$_2$CH$_3$), 2.74-2.77 (2H, m, NCH$_2$CH$_2$CH$_2$Ar), 2.11-2.11-(2H, m, NCH$_2$CH$_2$CH$_2$Ar), 1.77-1.84 (2H, m, CH$_2$CH$_2$CH$_3$), 1.46-1.49 (3H, m, OCH$_2$CH$_3$), 0.97-1.00 (3H, m, CH$_2$CH$_2$CH$_3$) |
| 72 | 8.76 (1H, s, H-4), 8.36-8.37 (1H, d, J = 7.5 Hz, H-8), 7.75-7.77 (1H, d, J = 8.0 Hz, H-5), 7.64-7.67 (1H, m, H-6), 7.32-7.35 (1H, m, H-7), 4.17 (3H, s, NCH$_3$), 3.35-3.38 (2H, m, CH$_2$CH$_2$CH$_3$), 1.85-1.89 (2H, m, CH$_2$CH$_2$CH$_3$), 1.04-1.07 (3H, m, CH$_2$CH$_2$CH$_3$) |
| 73 | 8.77 (1H, s, H-4), 8.37-8.39 (1H, d, J = 7.5 Hz, H-8), 7.77-7.79 (1H, d, J = 8.5 Hz, H-5), 7.64-7.67 (1H, m, H-6), 7.32-7.36 (1H, m, H-7), 4.63-4.68 (2H, m, NCH$_2$CH$_3$), 3.26-3.30 (2H, m, CH$_2$CH$_2$CH$_3$), 1.86-1.93 (2H, m, CH$_2$CH$_2$CH$_3$), 1.37-1.40 (3H, m, NCH$_2$CH$_3$), 1.05-1.08 (3H, m, CH$_2$CH$_2$CH$_3$) |
| 74 | 8.83 (1H, s, H-4), 8.43-8.45 (1H, d, J = 8 Hz, H-8), 7.70-7.71 (1H, d, J = 8.0 Hz, H-5), 7.60-7.63 (1H, m, H-6), 7.35-7.38 (1H, m, H-7), 7.22-7.29 (3H, m, Ar—H), 6.93-6.95 (2H, m, Ar—H), 5.92 (2H, s, NCH$_2$Ar), 3.07-3.10 (2H, m, CH$_2$CH$_2$CH$_3$), 1.67-1.75 (2H, m, CH$_2$CH$_2$CH$_3$), 0.86-0.89 (3H, m, CH$_2$CH$_2$CH$_3$) |
| 75 | 8.75 (1H, s, H-4), 8.36-8.38 (1H, d, J = 7.5 Hz, H-8), 7.71-7.72 (1H, d, J = 8.0 Hz, H-5), 7.62-7.65 (1H, m, H-6), 7.19-7.35 (6H, m, H-7, Ar—H), 4.57-4.60 (2H, s, NCH$_2$CH$_2$CH$_2$Ar), 3.06-3.09 (2H, m, CH$_2$CH$_2$CH$_3$), 2.74-2.77 (2H, m, NCH$_2$CH$_2$CH$_2$Ar), 2.05-2.11 (2H, m, CH$_2$CH$_2$CH$_3$), 1.73-1.79 (2H, m, NCH$_2$CH$_2$CH$_2$Ar), 0.92-0.96 (3H, m, CH$_2$CH$_2$CH$_3$) |
| 76 | 8.91 (1H, s, H-4), 8.24-8.25 (1H, d, J = 7.5 Hz, H-8), 7.63-7.66 (3H, m, H-5, H-6, H-7), 7.45-7.53 (4H, m, Ar—H), 7.37-7.40 (1H, m, Ar—H), 4.03 (3H, s, NCH$_3$), 3.47 (3H, s, OCH$_3$) |
| 77 | 8.92 (1H, s, H-4), 8.23-8.26 (1H, d, J = 8 Hz, H-8), 7.60-7.64 (3H, m, H-5, H-6, H-7), 7.45-7.53 (4H, m, Ar—H), 7.35-7.39 (1H, m, Ar—H), 3.96-4.03 (5H, s, NCH$_2$CH$_3$,OCH$_3$), 0.98-1.01 (3H, m,, NCH$_2$CH$_3$) |
| 78 | 8.93 (1H, s, H-4), 8.45-8.46 (1H, d, J = 7.5 Hz, H-8), 7.65-7.70 (4H, m, H-5, H-6, H-7, Ar—H), 7.56-7.60 (3H, m, Ar—H), 7.36-7.39 (1H, m, Ar—H), 3.44-3.47 (3H, s, NCH$_3$) |
| 79 | 8.98 (1H, s, H-4), 8.46-8.48 (1H, d, J = 8 Hz, H-8), 7.71-7.73 (1H, d, J = 8 Hz, H-5), 7.56-7.68 (6H, m, H-6, H-7, Ar—H), 7.36-7.39 (1H, m, Ar—H), 4.02-4.06 (2H, m, NCH$_2$CH$_3$), 0.86-0.89 (3H, m, NCH$_2$CH$_3$) |

Synthesis of 9-substituted β-carboline derivatives

Experimental Instruments and Reagents
Experimental instruments are as described above.
Chemical Reagents
L-tryptophan (Acros Organic, U.S.), 40% formaldehyde solution (analytically pure, Guangzhou Chemical Reagent Plant), selenium dioxide (Acros Organic, U.S.), benzyl bromide (chemically pure, Shanghai Chemical Reagent Co., China National Pharmaceutical Group), methyl iodide (analytically pure, Zhenjiang Yuhuan Biological Reagent Plant), ethyl iodide (analytically pure, Zhenjiang Yuhuan Biological Reagent Plant), iodo-n-butane (chemically pure, Shanghai Chemical Reagent Co., China National Pharmaceutical Group), and other domestically manufactured analytically pure or chemically pure reagents were used.

Scheme I

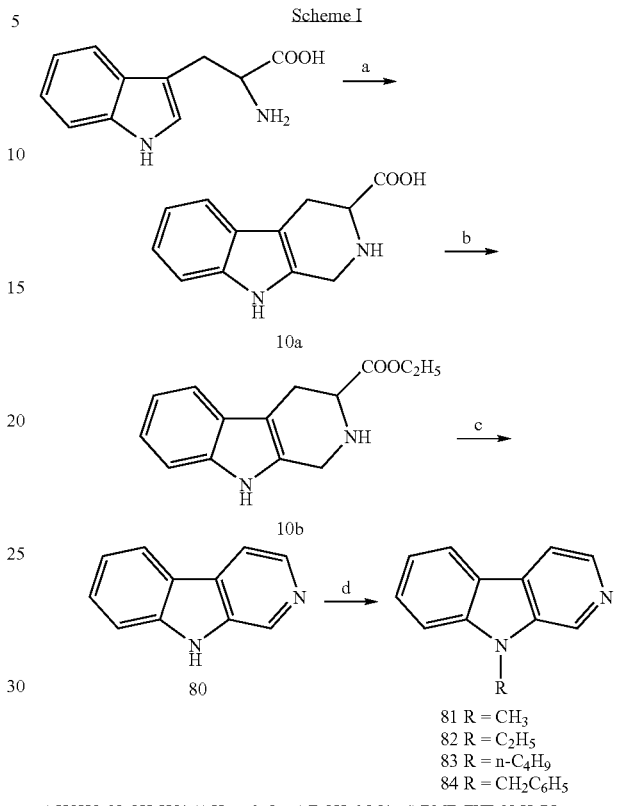

81 R = CH$_3$
82 R = C$_2$H$_5$
83 R = n-C$_4$H$_9$
84 R = CH$_2$C$_6$H$_5$ a) HCHO, NaOH, HCl; b) HAc, SeO$_2$; c) EtOH, SOCl$_2$, d) DMF, THF, NaH, RI

Example 110

Synthesis of β-carboline (80)

Compound 10b (24.4 g, 0.1 mol) was mixed with glacial acetic acid (500 ml) followed by the addition of selenium dioxide (20 g, 0.2 mol). The mixture was refluxed for 12 h. The glacial acetic acid was removed I. 1M NaOH solution (200 ml) was added into the residues, then the mixture was extracted with ethyl acetate. The organic phases were combined, washed by 1M NaOH solution, water and brine, dried, decolorized with activated carbon, filtered, evaporated and recrystallized with ethyl acetate to afford white solids (10.0 g, 60%), and mp 197-198° C. (reference[20]: 198 to 200° C.).

Example 111

General procedure for the preparation of 9-substituted β-carboline

β-carboline 80 (1.68 g, 10 mmol) was mixed with DMF (50 ml) followed by the addition of alkyl halide or aromatics halide (50 mmol). The mixture was stirred at room temperature for 5 h. TLC track measurement was conducted. After the reaction was finished, cold water was poured into the reaction mixture, and then extracted with ethyl acetate. The organic phases were combined, washed by water and brine, dried, decolorized with activated carbon, filtered and evaporated. The residues were purified by silica gel column chromatography with petroleum ether/acetone (2:1) as the eluent. The collected liquid was concentrated and recrystallized with ethyl acetate. Examples 112 to 115 were all treated according to the above procedures.

Example 112

Synthesis of 9-methyl-β-carboline (81)

Afforded white needle solids (1.4 g, 77%), and mp 108-109° C.

Example 113

Synthesis of 9-ethyl-β-carboline (82)

Afforded yellow oil (1.5 g, 76%).

Example 114

Synthesis of 9-n-butyl-β-carboline (83)

Afforded white needle solids (1.6 g, 71%), and mp 78-79° C.

Example 115

Synthesis of 9-Benzyl-β-carboline (84)

Afforded white needle solids (1.8 g, 69%), and mp 118-120° C.

Physico-Chemical Properties, TLC and Spectra Analyses of 9-Substituted β-Carboline Derivatives

TABLE 18 physico-chemical data of 9-substituted β-carboline derivatives

| Compd | Formula | FW | Yield (%) | Appearance | Solubility | Mp (° C.) |
|---|---|---|---|---|---|---|
| 80 | $C_{11}H_8N_2$ | 168 | 60 | white powder solids | soluble in alcohols, ethers, esters, chloroform etc. | 198-200 |
| 81 | $C_{12}H_{10}N_2$ | 182 | 65 | white needle-like crystals | soluble in alcohols, ethers, esters, chloroform etc. | 108-109 |
| 82 | $C_{13}H_{12}N_2$ | 196 | 76 | light yellow oil product | soluble in alcohols, ethers, esters, chloroform etc. | — |
| 83 | $C_{15}H_{16}N_2$ | 224 | 71 | white needle-like crystals | soluble in alcohols, ethers, esters, chloroform etc. | 78-79 |
| 84 | $C_{18}H_{14}N_2$ | 258 | 69 | white solids | soluble in alcohols, ethers, esters, chloroform etc. | 118-120 |

TABLE 19

FAB-MS, IR and UV data of 9-substituted β-carboline derivatives

| Compd | Formula | FAB-MS m/e (M + 1) | IR (KBr, cm$^{-1}$) | UV$_{\lambda max}$ (nm) |
|---|---|---|---|---|
| 80 | $C_{11}H_8N_2$ | 169 | ND | ND |
| 81 | $C_{12}H_{10}N_2$ | 183 | 2058, 1638, 1503, 1335, 1258, 835, 754, 718 | 360, 346, 289, 260, 236, 216 |
| 82 | $C_{13}H_{12}N_2$ | 197 | 3043, 2960, 2484, 2022, 1633, 1500, 1461, 1355, 1239, 831, 746, 719 | 365, 290, 260, 253, 218, 207 |
| 83 | $C_{15}H_{16}N_2$ | 225 | 3013, 2957, 2525, 2030, 1632, 1500, 1458, 1331, 823, 745, 720 | 362, 347, 290, 237, 217 |
| 84 | $C_{18}H_{14}N_2$ | 259 | 3023, 2939, 1619, 1447, 1332, 1200, 1025, 821, 752 | 358, 344, 289, 237, 212 |

TABLE 20

$^1$H-NMR data of 9-substituted β-carboline derivatives

| Comp | $^1$H-NMR (δ, CDCl$_3$) |
|---|---|
| 81 | 8.88 (1H, s, H-4), 8.46-8.47 (1H, d, J = 5 Hz, H-1), 8.13-8.14 (1H, d, J = 6 Hz, H-8), 7.94-7.95 (1H, d, J = 5 Hz, H-3), 7.59-7.62 (1H, m, H-5), 7.45-7.46 (1H, d, J = 8.5 Hz, H-6), 7.25-7.30 (1H, m, H-7), 3.93 (3H, s, CH$_3$) |
| 82 | 8.84 (1H, s, H-4), 8.42-8.43 (1H, d, J = 5 Hz, H-1), 8.04-8.05 (1H, d, J = 8 Hz, H-8), 7.85-7.86 (1H, d, J = 5 Hz, H-3), 7.50-7.53 (1H, m, H-5), 7.34-7.36 (1H, d, J = 8 Hz, H-6), 7.20-7.23 (1H, m, H-7), 4.26-4.30 (2H, m, CH$_2$CH$_3$), 1.35-1.38 (3H, m, CH$_2$CH$_3$) |

TABLE 20-continued

¹H-NMR data of 9-substituted β-carboline derivatives

| Comp | ¹H-NMR (δ, CDCl₃) |
|---|---|
| 83 | 8.86 (1H, s, H-4), 8.43-8.44 (1H, d, J = 5.5 Hz, H-1), 8.06-8.08 (1H, d, J = 8 Hz, H-8), 7.88-7.89 (1H, d, J = 4.5 Hz, H-3), 7.52-7.55 (1H, m, H-5), 7.38-7.40 (1H, d, J = 8.5 Hz, H-6), 7.21-7.25 (1H, m, H-7), 4.25-4.28 (2H, m, $CH_2CH_2CH_2CH_3$), 1.79-1.85 (2H, m, $CH_2CH_2CH_2$—$CH_3$), 1.30-1.38 (2H, m, $CH_2CH_2CH_2CH_3$), 0.86-0.91 (3H, m, $CH_2CH_2CH_2CH_3$) |
| 84 | 8.84 (1H, s, H-4), 8.48 (1H, s, H-1), 8.15-8.16 (1H, d, J = 8 Hz, H-8), 7.98 (1H, s, H-3), 7.53-7.56 (1H, m, H-5), 7.41-7.43 (1H, d, J = 8 Hz, H-6), 7.13-7.31 (6H, m, J = 8 Hz, H-7, Ar—H), 5.55 (2H, s, $CH_2Ar$) |

Synthesis of 2,9-disubstituted β-carboline derivatives

Experimental Instruments and Reagents

The experimental instruments are as described above.

Chemical Reagents

The chemical reagents are as described above.

Synthetic Routes and Operational Steps

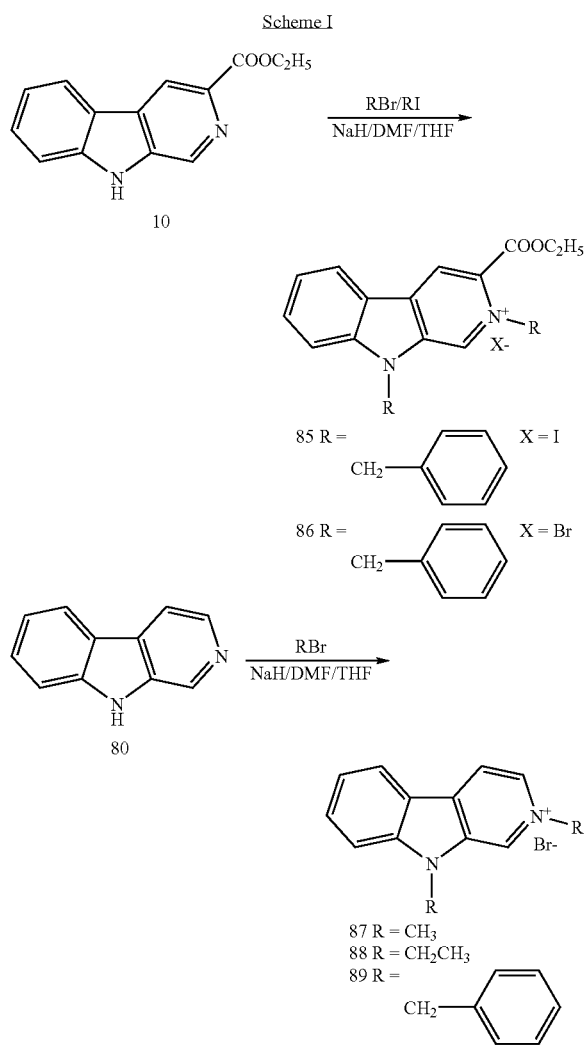

Example 116

Synthesis of 2,9-dibenzyl-3-ethoxycarbonyl-β-carbolinium iodate (85)

Compound 10 (1.2 g, 5 mmol) was mixed with DMF (50 ml) and 60% NaH (0.6 g, 15 mmol). The mixture was stirred at room temperature for 5 minutes followed by the addition of benzyl iodide (5 ml). The mixture was further stirred and reacted at 50 to 60° C. for 2 h. The reaction mixture was poured into 50 ml cold water and extracted by ethyl acetate. The organic phase was dried with anhydrous sodium sulfate and then concentrated to afford gold solids. The solids were recrystallized with anhydrous ethanol twice to afford gold solids (2.3 g, 84%), mp>270° C.

Example 117

Synthesis of Synthesis of 2,9-dibenzyl-3-ethoxycarbonyl-β-carbolinium bromate (86)

Compound 10 (1.2 g, 5 mmol) was mixed with DMF (50 ml) and 60% NaH (0.6 g, 15 mmol) followed by the addition of benzyl bromide (4 ml). The mixture was stirred and reacted at 50 to 60° C. for 5 h. The reaction mixture was poured into 50 ml cold water and extracted by ethyl acetate. The organic phase was dried with anhydrous sodium sulfate and then concentrated to afford gold solids. The solids were recrystallized with anhydrous ethanol to afford gold solids (1.8 g, 72%), mp>270° C.

Example 118

Synthesis of 2,9-dimethyl-β-carbolinium bromate (87)

Compound 80 (0.84 g, 5 mmol) was mixed with DMF (30 ml) and 60% NaH (0.3 g, 15 mmol) followed by the addition of methyl bromide (30 mmol). The mixture was stirred and reacted at 50 to 70° C. for 0.5 hour. The reaction mixture was poured into 100 ml cold water and extracted by ethyl acetate. The extract was dried with anhydrous sodium sulfate and then concentrated to afford yellow solids. The solids were recrystallized with anhydrous ethanol to afford white solids (1.8 g, 73%), mp>270° C.

Example 119

Synthesis of 2,9-diethyl-β-carbolinium bromate (88)

Compound 80 (0.84 g, 5 mmol) was mixed with DMF (30 ml) and 60% NaH (0.3 g, 15 mmol) followed by the addition of ethyl bromide (30 mmol). The mixture was stirred and reacted at 50 to 60° C. for 2 h. The reaction mixture was poured into 100 ml cold water and extracted with ethyl acetate. The extract was dried with anhydrous sodium sulfate and then concentrated to afford yellow solids. The solids were recrystallized with anhydrous ethanol to afford yellow solids (1.1 g, 63%), mp>270° C.

Example 120

Synthesis of 2,9-dibenzyl-β-carbolinium bromate (89)

Compound 80 (0.84 g, 5 mmol) was mixed with DMF (30 ml) and 60% NaH (0.3 g, 15 mmol). The mixture was stirred and reacted at room temperature for 10 minutes followed by the addition of benzyl bromide (50 mmol). The mixture was stirred and reacted at 50 to 60° C. for 5 h. The reaction mixture was poured into 75 ml cold water and extracted with ethyl acetate. The extract was dried with anhydrous sodium sulfate and then concentrated to afford light yellow solids. The solids were recrystallized with anhydrous ethanol to afford yellow solids (1.8 g, 76%), mp>270° C.

Physico-Chemical Constants, TLC and Spectra Analyses of 2,9-Disubstituted β-Carboline Derivatives

TABLE 21 physico-chemical data of 2,9-disubstituted β-carboline derivatives

| Compd | Formula | FW | Yield (%) | Appearance | Solubility | Mp (° C.) |
|---|---|---|---|---|---|---|
| 85 | $C_{28}H_{25}N_2IO_2$ | 548 | 84 | gold solids | soluble in alcohols, DMSO and water | >270 |
| 86 | $C_{28}H_{25}N_2BrO_2$ | 501 | 72 | gold solids | soluble in alcohols, DMSO and water | >270 |
| 87 | $C_{13}H_{13}IN_2$ | 324 | 73 | light yellow solids | soluble in methanol, DMSO and water | >270 |
| 88 | $C_{15}H_{17}IN_2$ | 352 | 63 | light yellow solids | soluble in methanol, DMSO and water | >270 |
| 89 | $C_{25}H_{21}IN_2$ | 476 | 76 | light yellow solids | soluble in methanol, DMSO and water | >270 |

TABLE 22

FAB-MS, IR and UV data of 2,9-disubstituted β-carboline derivatives

| Compd | Formula | FAB-MS m/e (M + 1) | IR (KBr, cm$^{-1}$) | UV$_{\lambda max}$ (nm) |
|---|---|---|---|---|
| 85 | $C_{28}H_{25}N_2IO_2$ | 421 | ND | ND |
| 86 | $C_{28}H_{25}N_2BrO_2$ | 421 | 3421, 2976, 1726, 1630, 1517, 1457, 1367, 1304, 1257, 1096, 1006 | 397, 317, 284, 243 |
| 87 | $C_{13}H_{13}IN_2$ | 197 | 3447, 2985, 1807, 1642, 1517, 1467, 1376, 1335, 1262, 1153 | 390, 309, 261, 257, 220, 210 |
| 88 | $C_{15}H_{17}IN_2$ | 225 | 3437, 2977, 1815, 1639, 1509, 1458, 1335, 1243, 1158, 1083 | 389, 310, 261, 257, 220210 |
| 89 | $C_{25}H_{21}IN_2$ | 349 | 3409, 2982, 2935, 1644, 1511, 1453, 1337, 1211, 1134 | 390, 313, 262, 235, 205 |

TABLE 23

$^1$H-NMR data of 2,9-disubstituted β-carboline derivatives

| Compd | $^1$H-NMR (δ, DMSO-d$_6$) |
|---|---|
| 86 | 9.88 (1H, s, H-4), 9.30 (1H, s, H-1), 8.55-8.57 (1H, d, J = 7.5 Hz, H-8), 7.87-7.92 (2H, m, H-5, H-6), 7.55-7.59 (1H, m, H-7), 7.20-7.36 (1OH, m, Ar—H), 6.39 (2H, s, $^+$N—CH$_2$—Ar), 5.98 (2H, s, NCH$_2$—Ar), 4.44-4.48 (2H, m, OCH$_2$CH$_3$), 1.34-1.37 (3H, m, OCH$_2$CH$_3$) |
| 87 | 9.42 (1H, s, H-4), 8.66-8.67 (1H, d, J = 6.5 Hz, H-1), 8.51-8.52 (1H, d, J = 6.0 Hz, H-8), 8.43-8.45 (1H, d, J = 8 Hz, H-3), 7.83-7.91 (2H, m, H-5, H-6), 7.50-7.53 (1H, m, H-7), 4.57 (3H, m, $^+$NCH$_3$), 4.13 (3H, m, NCH$_3$) |
| 88 | 9.61 (1H, s, H-4), 8.68-8.69 (1H, d, J = 6.5 Hz, H-1), 8.61-8.63 (1H, d, J = 6.5 Hz, H-8), 8.42-8.44 (1H, d, J = 8 Hz, H-3), 7.84-7.89 (2H, m, H-5, H-6), 7.48-7.51 (1H, m, H-7), 4.83-4.87 (2H, m,$^+$NCH$_2$CH$_3$), 4.67-4.72 (2H, m, NCH$_2$CH$_3$), 1.75-1.78 (3H, m, $^+$NCH$_2$CH$_3$), 1.51-1.54 (3H, m, NCH$_2$CH$_3$) |
| 89 | 9.57 (1H, s, H-4), 8.71 (2H, s, H-1, H-8), 8.42-8.44 (1H, d, J = 8.5 Hz, H-3), 7.81-7.82 (2H, m, H-5, H-6), 7.40-7.50 (6H, m, H-7, Ar—H), 7.19-7.28 (5H, m, Ar—H), 5.95 (2H, s, N$^+$CH$_2$Ar), 5.86 (2H, s, NCH$_2$Ar) |

Example 121

Assay of Acute Toxicities

Materials and methods

1. Materials (1) Chemicals: compounds 11, 16, 33, 36, 37, 42, 48, 55, 84 and 86

(2) Animals: Healthy mice, Kunming species (provided by Shanghai Experimental Animal Center, the Chinese Academy of Sciences, Certificate No.: Hudonghezhengzidi 107), weighing 19-20 g, each group contained 10 mice (five males and five females)
(3) Solvents: physiological saline and 0.5% CMC-Na solution 2. Methods
(1) Dosage Setting Five grades of dosages for each sample according to the results of the preliminary test, each dosage being 0.8 larger than the previous one (2) Formulation of the Medicament During the experiment, each sample was added a small amount of Tween-80 to facilitate dissolution after the sample was weighed, and then 0.5% CMC-Na solution was gradually added to achieve the desired concentration. The experimental volume was 0.5 ml/20 g mouse.

(3) Administration Manner

Single injection via intraperitoneal (i.p.) to different groups mice.

(4) Test on Acute Toxicity

Kunming mice were divided into different groups randomly according to their sex. The medicament was intraperitoneally administered to each group of mice according to the dosage setting. After the administration of the medicaments, mice were observed continuously for the first 2 h for any gross behavioral changes and deaths. Dead animals were dissected and examined for any possible organ damage. Survived animals were observed for another two weeks. Conditions of animals died within two week were recorded. After two weeks, all survived animals were sacrificed and checked macroscopically for possible damage to the heart, liver, kidneys and so on. Viscera that had substantive pathological changes were pathologically examined. According to the number of dead animals in each group, semi-lethal dosage ($LD_{50}$ value) was calculated, and the maximum tolerance dosage (MTD) of compounds that had lower toxicity was calculated too.

TABLE 24

Acute toxic effect of compound 11 in mice (administration via intraperitoneal)

| Sex | Dosage (mg/kg) | Number of animals | Death distribution (day) 12345678910--21 | Death rate | $LD_{50}$ (95% CL) (mg/kg) |
|---|---|---|---|---|---|
| male | 300 | 5 | 5000000000---0 | 100 | |
| | 240 | 5 | 4000000000---0 | 80 | |
| | 192 | 5 | 2000000000---0 | 40 | |
| | 153.6 | 5 | 1000000000---0 | 20 | |
| | 122.9 | 5 | 0000000000---0 | 0 | |
| female | 300 | 5 | 5000000000---0 | 100 | |
| | 240 | 5 | 5000000000---0 | 100 | |
| | 192 | 5 | 3000000000---0 | 60 | |
| | 153.6 | 5 | 2000000000---0 | 40 | |
| | 122.9 | 5 | 0000000000---0 | 0 | |
| 50% male | 300 | 10 | 10000000000---0 | 100 | 183.47 (159.21-211.43) |
| 50% female | 240 | 10 | 9000000000---0 | 90 | |
| | 192 | 10 | 5000000000---0 | 50 | |
| | 153.6 | 10 | 3000000000---0 | 30 | |
| | 122.9 | 10 | 0000000000---0 | 0 | |

TABLE 25

Acute toxic effect of compound 16 in mice (administration via intraperitoneal)

| Sex | Dosage (mg/kg) | Number of animals | Death distribution (day) 12345678910--21 | Death rate | $LD_{50}$ (95% CL) (mg/kg) | Sex |
|---|---|---|---|---|---|---|
| Male | 300 | 5 | 1000000000---0 | 20 | 19.6/25.2 | |
| | 240 | 5 | 0000000000---0 | 0 | 19.7/25.7 | |
| | 192 | 5 | 0000000000---0 | 0 | 19.8/26.1 | |
| | 153.6 | 5 | 0000000000---0 | 0 | 19.8/26.4 | |
| | 122.9 | 5 | 0000000000---0 | 0 | 19.8/26.3 | |
| female | 300 | 5 | 2000000000---0 | 40 | 20.0/23.3 | |
| | 240 | 5 | 0000000000---0 | 0 | 20.2/24.2 | |
| | 192 | 5 | 0000000000---0 | 0 | 19.9/24.9 | |
| | 153.6 | 5 | 0000000000---0 | 0 | 20.1/24.7 | |
| | 122.9 | 5 | 0000000000---0 | 0 | 20.1/24.8 | |
| 50% male | 300 | 10 | 3000000000---0 | 30 | | 240 |
| 50% female | 240 | 10 | 0000000000---0 | 0 | | |
| | 192 | 10 | 0000000000---0 | 0 | | |
| | 153.6 | 10 | 0000000000---0 | 0 | | |
| | 122.9 | 10 | 0000000000---0 | 0 | | |

TABLE 26

Acute toxic effect of compound 33 in mice (administration via intraperitoneal)

| Sex | Dosage (mg/kg) | Number of animals | Death distribution (day) 12345678910--21 | Death rate | LD$_{50}$ (95% CL) (mg/kg) |
|---|---|---|---|---|---|
| male | 300 | 5 | 4000000000---0 | 80 | |
| | 240 | 5 | 2000000000---0 | 40 | |
| | 192 | 5 | 0000000000---0 | 0 | |
| | 153.6 | 5 | 0000000000---0 | 0 | |
| | 122.9 | 5 | 0000000000---0 | 0 | |
| female | 300 | 5 | 5000000000---0 | 100 | |
| | 240 | 5 | 3000000000---0 | 60 | |
| | 192 | 5 | 1000000000---0 | 20 | |
| | 153.6 | 5 | 0000000000---0 | 0 | |
| | 122.9 | 5 | 0000000000---0 | 0 | |
| 50% male | 300 | 10 | 9000000000---0 | 90 | 240.38 (211.28-273.50) |
| 50% female | 240 | 10 | 5000000000---0 | 50 | |
| | 192 | 10 | 1000000000---0 | 10 | |
| | 153.6 | 10 | 0000000000---0 | 0 | |
| | 122.9 | 10 | 0000000000---0 | 0 | |

TABLE 27

Acute toxic effect of compound 36 in mice (administration via intraperitoneal)

| Sex | Dosage (mg/kg) | Number of animals | Death distribution (day) 12345678910--21 | Death rate | LD$_{50}$ (95% CL) (mg/kg) | Sex |
|---|---|---|---|---|---|---|
| male | 300 | 5 | 1000000000---0 | 20 | 20.0/25.5 | |
| | 240 | 5 | 0000000000---0 | 0 | 20.2/25.0 | |
| | 192 | 5 | 0000000000---0 | 0 | 20.1/26.2 | |
| | 153.6 | 5 | 0000000000---0 | 0 | 20.1/26.2 | |
| | 122.9 | 5 | 0000000000---0 | 0 | 20.2/26.4 | |
| female | 300 | 5 | 2000000000---0 | 40 | 19.7/24.3 | |
| | 240 | 5 | 0000000000---0 | 0 | 19.5/24.5 | |
| | 192 | 5 | 0000000000---0 | 0 | 19.8/24.9 | |
| | 153.6 | 5 | 0000000000---0 | 0 | 19.7/24.8 | |
| | 122.9 | 5 | 0000000000---0 | 0 | 19.9/25.2 | |
| 50% male | 300 | 10 | 3000000000---0 | 30 | >300 | |
| 50% female | 240 | 10 | 0000000000---0 | 0 | | |
| | 192 | 10 | 0000000000---0 | 0 | | |
| | 153.6 | 10 | 0000000000---0 | 0 | | |
| | 122.9 | 10 | 0000000000---0 | 0 | | |

TABLE 28

Acute toxic effect of compound 37 in mice (administration via intraperitoneal)

| Sex | Dosage (mg/kg) | Number of animals | Death distribution (day) 12345678910--21 | Death rate | LD$_{50}$ (95% CL) (mg/kg) |
|---|---|---|---|---|---|
| male | 300 | 5 | 5000000000---0 | 100 | |
| | 240 | 5 | 5000000000---0 | 100 | |
| | 192 | 5 | 3000000000---0 | 60 | |
| | 153.6 | 5 | 2000000000---0 | 40 | |
| | 122.9 | 5 | 0000000000---0 | 0 | |
| female | 300 | 5 | 5000000000---0 | 100 | |
| | 240 | 5 | 5000000000---0 | 100 | |
| | 192 | 5 | 4000000000---0 | 80 | |
| | 153.6 | 5 | 2000000000---0 | 40 | |
| | 122.9 | 5 | 1000000000---0 | 10 | |
| 50% male | 300 | 10 | 10000000000---0 | 100 | 163.48 (141.56-188.76) |
| 50 female | 240 | 10 | 10000000000---0 | 100 | |
| | 192 | 10 | 7000000000---0 | 70 | |
| | 153.6 | 10 | 4000000000---0 | 40 | |
| | 122.9 | 10 | 1000000000---0 | 10 | |

TABLE 29

Acute toxic effect of compound 42 in mice (administration via intraperitoneal)

| Sex | Dosage (mg/kg) | Number of animals | Death distribution (day) 12345678910--21 | Death rate | LD$_{50}$ (95% CL) (mg/kg) |
|---|---|---|---|---|---|
| male | 300 | 5 | 4000000000---0 | 80 | |
| | 240 | 5 | 2000000000---0 | 40 | |
| | 192 | 5 | 0000000000---0 | 0 | |
| | 153.6 | 5 | 0000000000---0 | 0 | |
| | 122.9 | 5 | 0000000000---0 | 0 | |
| female | 300 | 5 | 4000000000---0 | 80 | |
| | 240 | 5 | 3000000000---0 | 60 | |
| | 192 | 5 | 1000000000---0 | 20 | |
| | 153.6 | 5 | 0000000000---0 | 0 | |
| | 122.9 | 5 | 0000000000---0 | 0 | |
| 50% male | 300 | 10 | 8000000000---0 | 80 | 247.13 (213.51-286.03) |
| 50% female | 240 | 10 | 5000000000---0 | 50 | |
| | 192 | 10 | 1000000000---0 | 10 | |
| | 153.6 | 10 | 0000000000---0 | 0 | |
| | 122.9 | 10 | 0000000000---0 | 0 | |

TABLE 30

Acute toxic effect of compound 48 in mice (administration via intraperitoneal)

| Sex | Dosage (mg/kg) | Number of animals | Death distribution (day) 12345678910--21 | Death rate | LD$_{50}$ (95% CL) (mg/kg) |
|---|---|---|---|---|---|
| male | 300 | 5 | 5000000000---0 | 100 | |
| | 240 | 5 | 3000000000---0 | 60 | |
| | 192 | 5 | 1000000000---0 | 20 | |
| | 153.6 | 5 | 0000000000---0 | 0 | |
| | 122.9 | 5 | 0000000000---0 | 0 | |
| female | 300 | 5 | 5000000000---0 | 100 | |
| | 240 | 5 | 3000000000---0 | 60 | |
| | 192 | 5 | 2000000000---0 | 40 | |
| | 153.6 | 5 | 0000000000---0 | 0 | |
| | 122.9 | 5 | 0000000000---0 | 0 | |
| 50% male | 300 | 10 | 10000000000---0 | 100 | 219.19 (193.25-248.61) |
| 50% female | 240 | 10 | 6000000000---0 | 60 | |
| | 192 | 10 | 3000000000---0 | 30 | |
| | 153.6 | 10 | 0000000000---0 | 0 | |
| | 122.9 | 10 | 0000000000---0 | 0 | |

TABLE 31

Acute toxic effect of compound 55 in mice (administration via intraperitoneal)

| Sex | Dosage (mg/kg) | Number of animals | Death distribution (day) 12345678910--21 | Death rate | LD$_{50}$ (95% CL) (mg/kg) | Sex |
|---|---|---|---|---|---|---|
| male | 300 | 5 | 2000000000---0 | 40 | 20.1/25.3 | |
| | 240 | 5 | 0000000000---0 | 0 | 20.2/25.7 | |
| | 192 | 5 | 0000000000---0 | 0 | 20.0/25.9 | |
| | 153.6 | 5 | 0000000000---0 | 0 | 20.0/26.2 | |
| | 122.9 | 5 | 0000000000---0 | 0 | 20.0/26.1 | |
| female | 300 | 5 | 3000000000---0 | 60 | 19.5/24.0 | |
| | 240 | 5 | 0000000000---0 | 0 | 19.8/24.5 | |
| | 192 | 5 | 0000000000---0 | 0 | 19.7/24.7 | |
| | 153.6 | 5 | 0000000000---0 | 0 | 19.7/24.6 | |
| | 122.9 | 5 | 0000000000---0 | 0 | 19.9/24.9 | |
| 50% male | 300 | 10 | 5000000000---0 | 50 | | 240 |
| 50% female | 240 | 10 | 0000000000---0 | 0 | | |
| | 192 | 10 | 0000000000---0 | 0 | | |
| | 153.6 | 10 | 0000000000---0 | 0 | | |
| | 122.9 | 10 | 0000000000---0 | 0 | | |

TABLE 32

Acute toxic effect of compound 84 in mice
(administration via intraperitoneal)

| Sex | Dosage (mg/kg) | Number of animals | Death distribution (day) 12345678910--21 | Death rate | LD$_{50}$ (95% CL) (mg/kg) | Sex |
|---|---|---|---|---|---|---|
| male | 300 | 5 | 1000000000---0 | 20 | 20.0/25.5 | |
| | 240 | 5 | 0000000000---0 | 0 | 20.2/25.1 | |
| | 192 | 5 | 0000000000---0 | 0 | 20.1/26.2 | |
| | 153.6 | 5 | 0000000000---0 | 0 | 20.0/26.3 | |
| | 122.9 | 5 | 0000000000---0 | 0 | 20.2/26.4 | |
| female | 300 | 5 | 2000000000---0 | 40 | 19.7/24.4 | |
| | 240 | 5 | 0000000000---0 | 0 | 19.6/24.6 | |
| | 192 | 5 | 0000000000---0 | 0 | 19.8/24.9 | |
| | 153.6 | 5 | 0000000000---0 | 0 | 19.8/24.7 | |
| | 122.9 | 5 | 0000000000---0 | 0 | 19.9/25.0 | |
| 50% male | 300 | 10 | 3000000000---0 | 30 | | 240 |
| 50% male | 240 | 10 | 0000000000---0 | 0 | | |
| 50% famle | 192 | 10 | 0000000000---0 | 0 | | |
| | 153.6 | 10 | 0000000000---0 | 0 | | |
| | 122.9 | 10 | 0000000000---0 | 0 | | |

TABLE 33

Acute toxic effect of compound 86 in mice
(administration via intraperitoneal)

| Sex | Dosage (mg/kg) | Number of animals | Death distribution (day) 12345678910--21 | Death rate | LD$_{50}$ (95% CL) (mg/kg) |
|---|---|---|---|---|---|
| male | 100 | 5 | 1350000000---0 | 90 | |
| | 80 | 5 | 0132000000---0 | 60 | |
| | 64 | 5 | 0031100000---0 | 50 | |
| | 51.2 | 5 | 0011100000---0 | 20 | |
| | 40.96 | 5 | 0000000000---0 | 0 | |
| female | 100 | 5 | 2341000000---0 | 100 | |
| | 80 | 5 | 0322000000---0 | 70 | |
| | 64 | 5 | 0121000000---0 | 40 | |
| | 51.2 | 5 | 0111000000---0 | 30 | |
| | 40.96 | 5 | 0000000000---0 | 0 | |
| 50% male | 100 | 10 | 3691000000---0 | 95 | 65.7 (58.25-74.11) |
| 50% female | 80 | 10 | 0454000000---0 | 65 | |
| | 64 | 10 | 0152100000---0 | 45 | |
| | 51.2 | 10 | 0122000000---0 | 25 | |
| | 40.96 | 10 | 0000000000---0 | 0 | |

3. Results
3.1 Observations of Ordinary Symptoms

After drug administration, all the mice exhibited symptoms such as quivering of abdominal muscles, stretch, loose hairs, and retardant action, but did not show obvious symptoms of nervous toxicity such as trembling, twists, and jumps. Death peak of the animal occurred the very day when the medicament was administered, except for compound 86. As for compound 86, the death peak occurred 2 to 3 days after the medicament was administered. Generally, no obvious abnormal organs were observed after the dead animals were dissected. Survived animals recovered to normal state gradually.
3.2 Results of Neurotoxicity and Acute Toxicity (LD$_{50}$/MTD)

See table 120-1 to table 120-10 for results of dosage-reaction value and LD$_{50}$ value or MTD value.

For the convenience of comparison, the results [153] of the previous tests on acute toxicity and the results of the present tests are shown in table 34.

TABLE 34

Results of neurotoxicities and the acute toxicities
(LD$_{50}$/MTD) of β-carboline derivatives

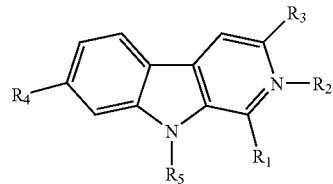

| Compd | R$_1$ | R$_2$ | R$_3$ | R$_4$ | R$_5$ | LD$_{50}$ | MTD | Neurotoxic |
|---|---|---|---|---|---|---|---|---|
| 1* | CH$_3$ | H | H | CH$_3$O | H | 59.00 | — | ++ |
| 2* | CH$_3$ | H | H | CH$_3$O | CH$_3$ | 28.92 | — | ++ |
| 3* | CH$_3$ | H | H | CH$_3$O | C$_2$H$_5$ | 24.25 | — | ++ |
| 4* | CH$_3$ | H | H | CH$_3$O | n-C$_4$H$_9$ | 26.45 | — | ++ |
| 6* | CH$_3$ | H | H | CH$_3$O | CH$_2$C$_6$H$_5$ | 147.82 | — | ++ |
| 11 | CH$_3$ | H | CO$_2$C$_2$H$_5$ | H | H | 183.47 | — | — |
| 16 | C$_6$H$_5$-p-OH | H | CO$_2$CH$_3$ | H | H | — | 240 | — |
| 17* | H | H | COOH | H | H | 135.22 | — | — |
| 26* | H | H | CO$_2$C$_2$H$_3$ | H | CH$_3$ | 70.61 | — | + |
| 27* | H | H | CO$_2$C$_2$H$_5$ | H | C$_2$H$_5$ | 95.06 | — | + |
| 33 | H | H | CO$_2$C$_2$H$_5$ | H | CH$_2$C$_6$H$_5$ | 240.38 | — | — |
| 36 | H | H | COOH | H | n-C$_4$H$_9$ | — | >300 | — |
| 37 | H | H | COOH | H | CH$_2$C$_6$H$_5$ | 163.48 | — | — |
| 42 | H | H | CH$_2$OH | H | CH$_2$C$_6$H$_5$ | 247.13 | — | — |
| 48 | H | H | COOH | H | (CH$_2$)$_3$C$_6$H$_5$ | 219.19 | — | — |
| 55 | H | H | NHCO$_2$C$_2$H$_5$ | H | CH$_2$C$_6$H$_5$ | — | 240 | — |
| 84 | H | H | H | H | CH$_2$C$_6$H$_5$ | — | 240 | — |
| 86 | H | CH$_2$C$_6$H$_5$ | CO$_2$C$_2$H$_5$ | H | CH$_2$C$_6$H$_5$ | 65.7 | — | — |

Example 122

In Vitro Cytotoxicy Assays

1. Materials and Method
1.1 Materials
(1) Reagents

RPMI1640 culture medium (GIBCO, U.S.), MTT (Sigma, U.S.), Fetal Bovine Serum (GIBCO or Hyclone, U.S.), HEPES (Sigma, U.S.), trypsin operating fluid (0.125% trypsin, Sigma, 0.01% EDTA, dissolved in D-Hanks solution), DMSO (Sigma, U.S.), cell freezing solution (90% FBS+10% DMSO), D-Hanks balanced salt solution (i.e. Hanks solution free of calcium and magnesium ions: 8 g NaCl, 0.4 g KCl, 0.06 g $Na_2HPO_4.2H_2O$, 0.06 g $KH_2PO_4.2H_2O$, 0.35 g $NaHCO_3$ were dissolved in tri-distilled water with no phenol red), PBS (8 g NaCl, 0.2 g KCl, 1.56 g $Na_2HPO_4.2H_2O$, 0.2 g $KH_2PO_4.2H_2O$ were dissolved in tri-distilled water) were used. Chemicals: 88 compounds synthesized as described in the second part of the description and harmine of formula 1.

Cells: HepG2, PLA-801, Bel-7402, BGC-823, Hela, Lovo and NIH3T3.

(2) Instruments

A super clean bench, a $CO_2$ cell culture incubator, an universal microplate Reader (BIO-TEK INSTRUMENT, INC.), an inverted microscope, a liquid nitrogen tank, an ultrapure water system (Millipore, Inc), various models of filters, a positive air filtration system, a centrifuge, and a constant temperature water bath were used.

Other reagents and instruments used included penicillin sodium sulfate, streptomycin sulfate, DMSO (Sigma), sodium bicarbonate, alcohol, benzalkonium bromide solution, various models of cell culture bottles and dishes, 96 pore/24 pore/6 pore cell culture plates, glass centrifuge tubes, glass pipettes, suckers, cannula, cell counting plates, various models of pipettors, cell freezing tubes, forceps and the like.

1.2 Methods
(1) Culture Solutions

Culture medium powder RPMI1640 was dissolved in a proper amount of tri-distilled water according to the instruction of the product. For every 1000 ml culture solution, 5.94 g HEPES and 2.0 g sodium bicarbonate were added. It was the basic culture solution. The complete culture solution was added with FBS having a final concentration of 10%, 100 U/ml penicillin and 100 g/ml streptomycin. The solution was fully stirred by a magnetic blender, and the pH of the solution was adjusted to 6.8-7.0. The volume was kept constant. After being filtered and disinfected, the solution was kept into several containers which were sealed and stored at 4° C.

(2) Culture and Subculture

The cells were placed in a culture dish followed by the addition of complete culture liquid RPMI1640 and then cultured in a incubator comprising 5% $CO_2$ at 37° C. In the exponential growth phase, the cells grew vigorously. If the culture liquid became yellow, the liquid should be replaced instantly.

Prior to the plateau phase, the cells needed to be subcultured. During the passage of the anchorage-dependent cells, the old culture liquid was removed. A proper amount of trypsin operating solution was added to digest the cells. When the cells became round and began to fall off, the complete culture liquid was added to terminate the digestion. The cells on the wall were blown off using a pipette. The cells were centrifugalized in a centrifuge tube at 1000 rpm for 5 minutes, and the supernatant was removed. The cells were blown off by the addition of culture liquid and then inoculated in the culture dish at a cell concentration of from 1/10 to 1/20. During the passage of the suspended or semi-suspended cells, the cells were blown homogenous by using a pipette and directly inoculated in a new culture liquid at a concentration of from 1/10 to 1/20.

(3) The Frozen and Recovery of the Cells

The cells in the exponential phase (the anchorage-dependent cells were digested by trypsin at first and then collected by centrifugalization, and the suspended and semi-suspended cells were directly collected by centrifugalization) were added into a pre-formulated cell freezing solution which was stored at 4° C., and were blown to form a unicellular suspension. The concentration of the suspension was adjusted to $10^6$ to $5\times10^6$ cell/ml, and then the suspension was transferred to a freezing tube surround by cloth. The tube was placed at 4° C., 20° C., and −80° C. respectively and finally suspended under liquid nitrogen such that the temperature of the tube would be lowered gradually. The tube was placed into a liquid nitrogen tank the next day.

During recovery, the freezing tube was taken out of the liquid nitrogen tank and quickly placed into a water bath at 37° C. The tube was stirred continuously such that the cells were quickly defrosted. The cells were transferred to a glass centrifuge tube at a sterile air bench followed by the addition of a small amount of culture liquid to wash the cells. The cells were centrifugalized at 1000 rpm. After the supernatant was removed, the cells were washed once again and then transferred to a culture dish to be cultured in a $CO_2$ incubator.

(4) Morphologic Observations of the Growth Condition of Tumor Cell Strains

The cells were cultured at a 96-pore culture plate while the cells were in the logarithmic growth phase. While samples having a preset concentration to be tested were placed at the plate, an equivalent amount of dissolvent for dissolving the medicament was added to serve as a comparison. The cells treated by the medicament and the control cells were observed in an optical microscope at different times. The morphologic changes of the cells were recorded and photographed.

(5) Measurement of $IC_{50}$ Value by MTT Method

The cells, at a concentration of $10^5$/ml, were inoculated at a 96-pore culture plate. In each pore, 100 μl cells were inoculated. The cells were placed in a $CO_2$ incubator until the cells were in the logarithmic growth phase. The samples to be tested were added according to the preset concentration gradient. For each gradient, the test was conducted at least three times. An equivalent amount of solvent for dissolving the samples was added in the control group. After 48 h of culture, each pore was added 20 μl MTT (5 mg/ml). The cells were cultured at 37° C. for 4 h. After the supernatant was carefully removed, 100 μl DMSO was added in each pore. The plate was agitated for about 10 minutes such that the precipitates were dissolved. After that, OD value was identified with a Microplate Reader at the wavelength of 490 nm. The survival rate of the cells at various concentrations was calculated according to the following formula:

Survival rate %=average OD value of the sample group/average OD value of the control group× 100%

Plots of log survival rate of the cells vs. concentration of the medicament were constructed, and the $IC_{50}$ value of each sample was calculated according to graphing methods.

3. Results
3.1 Morphologic Observations of the Growth Conditions of the Tumor Cell Strains See FIG. 12 for the morphologic observations of the growth conditions of the tumor cells.

It can be seen from the figure that the cell configuration was significantly changed after human liver cancer HepG2 cells were affected by β-carboline derivatives.

3.2 $IC_{50}$ Value Measured by MTT Methods

$IC_{50}$ Value of 1,7,9-Trisubstituted β-Carboline Derivatives $IC_{50}$ values of 1,7,9-trisubstituted β-carboline derivatives against tumor cell lines are shown in table 35.

TABLE 35

The $IC_{50}$ of 1,7,9-trisubstituted β-carboline derivatives against tumor cell lines (μmol/ml)

| | Cell strains | | | | | | |
|---|---|---|---|---|---|---|---|
| Compd | PLA-801 | HepG2 | BeI7402 | BGC823 | Hela | Lovo | NIH3T3 |
| 1 | 0.05 | 0.05 | 0.02 | 0.07 | 0.06 | 0.07 | 0.06 |
| 2 | 0.03 | 0.02 | 0.06 | 0.05 | 0.01 | 0.04 | 0.04 |
| 3 | 0.02 | 0.01 | 0.03 | 0.05 | 0.02 | 0.17 | 0.07 |
| 4 | 0.11 | 0.06 | 0.06 | 0.07 | 0.03 | 0.09 | 0.04 |
| 5 | 0.08 | 0.31 | 0.24 | 0.20 | 0.03 | 0.03 | 0.08 |
| 6 | 0.06 | 0.09 | 0.06 | 0.10 | 0.27 | 0.05 | 0.05 |
| 7 | 0.42 | 0.05 | 0.04 | 0.02 | 0.04 | 0.04 | 0.05 |
| 8 | 0.05 | 0.04 | 0.04 | 0.05 | 0.02 | 0.03 | 0.02 |

2. $IC_{50}$ values of 3- and 1,3-Disubstiuted β-Carboline Derivatives

See table 36 for the $IC_{50}$ values of 3- and 1,3-disubstituted β-carboline derivatives against tumor cell lines.

TABLE 36

The $IC_{50}$ values of 3- and 1,3-disubstituted β-carboline derivatives against tumor cell lines (μmol/ml)

| | Cell strains | | | | | | |
|---|---|---|---|---|---|---|---|
| Compd | PLA-801 | HepG2 | BeI7402 | BGC823 | Hela | Lovo | NIH3T3 |
| 9* | 0.31 | 2.51 | 0.30 | 0.29 | 0.10 | 0.17 | 0.20 |
| 10* | 0.28 | 1.25 | 2.91 | 1.28 | 0.06 | 1.01 | 0.08 |
| 11* | 0.26 | 0.09 | 0.23 | 0.11 | 0.10 | 0.08 | 0.10 |
| 12* | >3.0 | >3.0 | >3.0 | >3.0 | >3.0 | 1.57 | >3.0 |
| 13* | 0.67 | 1.06 | >3.0 | >3.0 | >3.0 | 0.74 | 0.75 |
| 14* | 1.90 | 1.18 | >5.0 | 1.68 | 0.32 | 2.48 | 0.49 |
| 15* | >3.0 | >3.0 | >3.0 | >3.0 | >3.0 | >3.0 | >3.0 |
| 16* | 1.02 | >5.0 | 1.08 | 0.97 | 0.15 | 0.62 | 2.18 |
| 17 | 0.30 | 0.28 | 0.23 | 0.28 | 0.22 | 0.17 | 0.06 |
| 18 | 0.68 | 0.27 | 0.31 | 0.39 | 0.29 | 0.10 | 0.15 |
| 19 | 0.14 | 0.08 | 0.16 | 0.08 | 0.09 | 0.10 | 0.20 |
| 20 | 0.74 | 0.36 | 1.43 | 0.74 | 0.40 | 0.31 | 0.32 |
| 21 | 0.57 | 0.34 | 1.57 | 0.86 | 0.31 | 0.24 | 0.29 |
| 22 | 0.20 | 0.23 | 0.13 | 0.21 | 0.17 | 0.16 | 0.32 |
| 23 | 2.16 | >3.0 | >3.0 | >3.0 | >3.0 | >3.0 | >3.0 |
| 24 | 1.08 | 0.58 | 0.74 | 0.78 | 0.62 | 0.49 | 0.36 |
| 25 | 0.78 | 1.13 | 0.59 | 0.64 | 0.78 | 0.25 | 0.31 |

3. $IC_{50}$ Values of 3,9-Disubstituted β-Carboline Derivatives

See table 37 for the $IC_{50}$ values of 3,9-disubstituted β-carboline derivatives against tumor cell lines.

TABLE 37

The $IC_{50}$ values of 3,9-disubstituted β-carboline derivatives against tumor cell lines (μmol/ml)

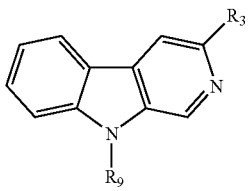

| Compd | $R_3$ | $R_9$ | PLA-801 | HepG2 | Bel7402 | BGC823 | Hela | Lovo | NIH3T3 |
|---|---|---|---|---|---|---|---|---|---|
| 26 | COOCH$_3$ | CH$_3$ | 0.12 | 0.12 | 0.19 | 0.18 | 0.18 | 0.18 | 0.09 |
| 27 | COOCH$_3$ | C$_2$H$_5$ | 0.29 | 0.16 | 0.53 | 0.25 | 0.21 | 0.11 | 0.13 |
| 28 | COOCH$_3$ | n-C$_4$H$_9$ | 0.14 | 0.46 | 0.43 | 0.31 | 0.29 | 0.17 | 0.08 |
| 29 | COOCH$_3$ | CH$_2$C$_6$H$_5$ | 0.48 | 1.77 | 0.06 | 0.95 | 0.12 | 0.31 | 0.36 |
| 30 | COOC$_2$H$_5$ | CH$_3$ | 0.12 | 0.15 | 0.14 | 0.15 | 0.18 | 0.10 | 0.10 |
| 31 | COOC$_2$H$_5$ | C$_2$H$_5$ | 0.17 | 0.11 | 0.26 | 0.14 | 0.14 | 0.07 | 0.10 |
| 32 | COOC$_2$H$_5$ | n-C$_4$H$_9$ | 0.07 | 0.48 | 0.78 | 0.76 | 0.49 | 0.17 | 0.06 |
| 33 | COOC$_2$H$_5$ | CH$_2$C$_6$H$_5$ | 0.17 | 0.08 | 0.34 | 0.15 | 0.01 | 0.12 | 0.05 |
| 34 | COOH | CH$_3$ | 0.27 | 0.15 | 0.33 | 0.13 | 0.09 | 0.09 | 0.13 |
| 35 | COOH | C$_2$H$_5$ | 0.21 | 0.18 | 0.23 | 0.16 | 0.18 | 0.06 | 0.14 |
| 36 | COOH | n-C$_4$H$_9$ | 0.09 | 0.17 | 0.09 | 0.12 | 0.06 | 0.01 | 0.02 |
| 37 | COOH | CH$_2$C$_6$H$_5$ | 0.10 | 0.10 | 0.11 | 0.05 | 0.09 | 0.04 | 0.05 |
| 38 | COOC$_4$H$_9$ | CH$_3$ | >3.0 | 1.61 | >3.0 | >3.0 | >3.0 | 2.52 | >3.0 |
| 39 | COOC$_4$H$_9$ | C$_2$H$_5$ | 0.11 | 0.07 | 0.07 | 0.08 | 0.07 | 0.08 | 0.08 |
| 40 | COOC$_4$H$_9$ | n-C$_4$H$_9$ | 2.12 | 1.08 | 1.08 | 0.07 | 0.95 | 0.04 | 0.05 |
| 41 | COOC$_4$H$_9$ | CH$_2$C$_6$H$_5$ | 0.99 | >3.0 | >3.0 | >3.0 | >3.0 | 1.08 | >3.0 |
| 42 | CH$_2$OH | CH$_2$C$_6$H$_5$ | 0.16 | 0.09 | 0.11 | 0.11 | 0.12 | 0.10 | 0.09 |
| 43 | CH$_2$OOCCH$_3$ | CH$_2$C$_6$H$_5$ | 0.25 | 0.30 | 0.13 | >3.0 | 0.50 | >3.0 | >3.0 |
| 44 | COOCH$_2$C$_6$H$_5$ | CH$_2$C$_6$H$_5$ | >3.0 | >3.0 | >3.0 | >3.0 | >3.0 | >3.0 | >3.0 |
| 45 | COOC$_2$H$_5$ | (CH$_2$)$_3$C$_6$H$_5$ | >3.0 | >3.0 | 0.387 | >3.0 | >3.0 | >3.0 | >3.0 |
| 46 | COOC$_2$H$_5$ | CH$_2$C$_6$F$_5$ | 0.05 | 0.12 | 0.01 | 0.05 | 0.98 | 0.04 | 0.06 |
| 47 | COOC$_2$H$_5$ | CH$_2$COC$_6$H$_5$ | >3.0 | >3.0 | 1.02 | >3.0 | >3.0 | >3.0 | >3.0 |
| 48 | COOH | (CH$_2$)$_3$C$_6$H$_5$ | 0.26 | 0.03 | 0.05 | 0.03 | 0.10 | 0.01 | 0.03 |
| 49 | COOH | CH$_2$C$_6$F$_5$ | 0.09 | 0.03 | 0.06 | 0.04 | 0.04 | 0.01 | 0.02 |
| 50 | COOH | CH$_2$COC$_6$H$_5$ | 0.14 | 0.09 | 0.14 | 0.06 | 0.07 | 0.07 | 0.05 |

TABLE 37-continued

The IC$_{50}$ values of 3,9-disubstituted β-carboline derivatives against tumor cell lines (μmol/ml)

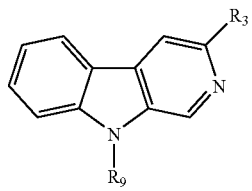

| Compd | R$_3$ | R$_9$ | PLA-801 | HepG2 | Bel7402 | BGC823 | Hela | Lovo | NIH3T3 |
|---|---|---|---|---|---|---|---|---|---|
| 51 | CONHNH$_2$ | C$_2$H$_5$ | 0.51 | 0.26 | 0.37 | 0.11 | 0.24 | 0.19 | 0.51 |
| 52 | CONHNH$_2$ | CH$_2$C$_6$H$_5$ | 0.52 | 0.14 | 0.06 | 0.27 | 0.25 | 0.25 | 0.22 |
| 53 | NHCOOCH$_3$ | C$_2$H$_5$ | >3.0 | >3.0 | >3.0 | >3.0 | >3.0 | >3.0 | >3.0 |
| 54 | NHCOOC$_2$H$_5$ | C$_2$H$_5$ | >3.0 | >3.0 | 1.68 | >3.0 | >3.0 | >3.0 | >3.0 |
| 55 | NHCOOC$_2$H$_5$ | CH$_2$C$_6$H$_5$ | 0.52 | >3.0 | 2.44 | >3.0 | >3.0 | 2.13 | 1.79 |

4. IC$_{50}$ Values of 1,3,9-Trisubstituted β-Carboline Derivatives

See table 38 for the IC$_{50}$ values of 1,3,9-trisubstituted β-carboline derivatives against tumor cell lines.

TABLE 38

The IC$_{50}$ values of 1,3,9-trisubstituted β-carboline derivatives against tumor cell lines (μmol/ml)

| | Cell strains | | | | | | |
|---|---|---|---|---|---|---|---|
| Compd | PLA-801 | HepG2 | Bel7402 | BGC823 | Hela | Lovo | NIH3T3 |
| 56 | 0.14 | 0.10 | 0.49 | 0.13 | 0.11 | 0.05 | 0.06 |
| 57 | 0.16 | 0.08 | 0.88 | 0.07 | 0.06 | 0.05 | 0.06 |
| 58 | 1.39 | 2.00 | 0.21 | 2.08 | 0.25 | 0.17 | 1.82 |
| 59 | 0.11 | 0.04 | 0.18 | 0.04 | 0.04 | 0.02 | 0.03 |
| 60 | 0.05 | 0.03 | 0.10 | 0.004 | 0.02 | 0.04 | 0.04 |
| 61 | 0.16 | 0.07 | 0.46 | 0.09 | 0.06 | 0.05 | 0.09 |
| 62 | 2.35 | 1.38 | 1.50 | 0.64 | 1.11 | 0.44 | 0.63 |
| 63 | 2.33 | 2.80 | 1.82 | 1.66 | 0.97 | 0.59 | 0.71 |
| 64 | 0.41 | 0.28 | 0.69 | 0.28 | 0.37 | 0.20 | 0.14 |
| 65 | 0.21 | 0.14 | 0.56 | 0.27 | 0.22 | 0.05 | 0.11 |
| 66 | 0.19 | 0.12 | 0.12 | 0.16 | 0.11 | 0.08 | 0.08 |
| 67 | 2.00 | 2.23 | >3.0 | 1.52 | 2.48 | 1.34 | 1.46 |
| 68 | 0.14 | 0.10 | 0.46 | 0.11 | 1.36 | 0.06 | 0.08 |
| 69 | 0.71 | 0.11 | 0.33 | 0.23 | 0.09 | 0.10 | 0.10 |
| 70 | 0.16 | 0.79 | 1.01 | 1.01 | 0.81 | 1.17 | 1.57 |
| 71 | 0.26 | 0.12 | 0.91 | 1.32 | 0.06 | 0.06 | 0.19 |
| 72 | 1.40 | 1.17 | >3.0 | 0.54 | 0.96 | 0.21 | 0.57 |
| 73 | 0.71 | 0.54 | 0.57 | 0.39 | 0.42 | 0.26 | 0.39 |
| 74 | 0.27 | 0.17 | 0.18 | 0.27 | 0.16 | 0.14 | 0.16 |
| 75 | 0.23 | 0.13 | 0.20 | 0.24 | 0.14 | 0.08 | 0.11 |
| 76 | >3.0 | >3.0 | 0.62 | >3.0 | >3.0 | >3.0 | >3.0 |
| 77 | >3.0 | >3.0 | 0.38 | >3.0 | 2.66 | 0.070 | 0.140 |
| 78 | 0.65 | 0.16 | 0.28 | 0.21 | 0.17 | 0.11 | 0.15 |
| 79 | 0.11 | 0.16 | 0.14 | 0.25 | 0.14 | 0.10 | 0.12 |

5. IC$_{50}$ Values of 9-Substituted β-Carboline Derivatives

See table 39 for the IC$_{50}$ values of 9-substituted β-carboline alkaloid derivatives against tumor cell lines.

TABLE 39

The IC$_{50}$ values of 9-substituted β-carboline derivatives against tumor cell lines (μmol/ml)

| | Cell strains | | | | | | |
|---|---|---|---|---|---|---|---|
| Compd | PLA-801 | HepG2 | Bel7402 | BGC823 | Hela | Lovo | NIH3T3 |
| 80 | 0.02 | 0.23 | 0.38 | 0.27 | 0.35 | 0.04 | 0.02 |
| 81 | 0.22 | 0.10 | 0.30 | 0.20 | 0.33 | 0.22 | 0.12 |
| 82 | 0.13 | 0.17 | 0.31 | 0.17 | 0.23 | 0.16 | 0.10 |
| 83 | 0.13 | 0.10 | 0.16 | 0.10 | 0.09 | 0.13 | 0.08 |
| 84 | 0.12 | 0.11 | 0.08 | 0.07 | 0.05 | 0.12 | 0.11 |

6. IC$_{50}$ Values of 2,9-Disubstituted β-Carboline Derivatives

See table 40 for the IC$_{50}$ values of 9-substituted β-carboline derivatives against tumor cell lines.

TABLE 40

The IC$_{50}$ values of 2,9-disubstituted β-carboline derivatives against tumor cell lines (μmol/ml)

| | Cell strains | | | | | | |
|---|---|---|---|---|---|---|---|
| Compd | PLA-801 | HepG2 | Bel7402 | BGC823 | Hela | Lovo | NIH3T3 |
| 85 | 0.03 | 0.02 | 0.04 | 0.04 | 0.03 | 0.03 | 0.02 |
| 86 | 0.01 | 0.04 | 0.05 | 0.04 | 0.03 | 0.02 | 0.02 |
| 87 | 0.28 | 0.20 | 0.37 | 0.26 | 0.07 | 1.82 | 0.38 |
| 88 | 1.20 | 0.43 | 1.31 | 1.31 | 0.86 | 2.15 | 0.63 |
| 89 | 0.10 | 0.03 | 0.07 | 0.06 | 0.02 | 0.03 | 0.03 |

Example 123

Assay of Anti-Tumor Activity

1 Materials and Methods
1.1. Materials
(1) Chemicals

Compounds 10, 11, 14, 15, 16, 31, 33, 37, 36, 42, 48, 55, 84 and 86 (see tables 12-3 for the chemical structures), and cyclophosphamide for injection used for positive control sample (available in Shanghai Hualian Pharmaceutical Group) was used.

(2) Animals

Mice C$_{57}$BL/6 and Kunming mice, (provided by Shanghai Experimental Animal Center, the Chinese Academy of Sciences, Certificate No.: Hudonghezhengzidi 107), weighing 18-20 g, The mice for each group of tests could be of the same sex. There was one group of 8 to 10 mice $C_{57}BL/6$ and Kunming mice for the anti-tumor tests and two groups of mice for negative control.

(3) Sources of tumors: Lewis lung cancer cells and S180 sarcoma in mice, which were sub-cultured and maintained by Pharmacological Center of Shanghai Pharmaceutical Industrial Research Institute.

(4) Solvents: Physiological Saline, and 0.5% CMC-Na Solution 1.2 Methods (1) Setting of the Dosage The medicaments tested were divided into a high dosage group and a low dosage group, which were respectively based on ⅕ and ⅒ of the $LD_{50}$ value or MTD value of said medicaments that were intraperitoneally administered once.

(2) Formulation of the Medicament

All samples were weighed and added a small amount of Tween-80 to facilitate dissolution during the experiment, and then 0.5% CMC-Na solution was gradually added to achieve the desired concentration. The volume for experiment was 0.5 ml/20 g mouse.

(3) Administration Scheme

The medicaments were intraperitoneally administered once a day continuously for 10 days.

For the negative control group, a vehicle of the same volume was intraperitoneally administered once a day continuously for 10 days. For the positive control group, CTX was administered in the dosage of 30 mg/kg once a day continuously for 7 days.

(4) Procedures of Assay of the Anti-Tumor Activity in Mice

In vivo anti-tumor subcutaneous vaccination in the axilla was employed. Wildly grown tumor source was taken under sterile conditions to form a cell suspension of about $1 \times 10^7$ ml by homogenization method. For a corresponding mouse host, the suspension was injected in the axilla in an amount of 0.2 ml/mouse. The next day, the medicaments were administered according to the design of the tests. About three weeks later, all the groups of animals were executed. The tumors were taken from the animals and weighed. The inhibition rate of tumors was calculated according to the following formula:

$$(C-T)/C \times 100$$

T: average tumor weight of treated group; C: average tumor weight of negative control group.

After the administration of the medicaments, mice were observed immediately for any gross behavioral changes and deaths as well as any neurotoxic symptoms, such as jumping, quivering, twisting and so on.

TABLE 41

The antitumor activity of β-carboline derivatives against mouse Lewis lung cancer

| Compd | Dosage (mg/ml) | Administration scheme | Number of animals (beginning/end) | Body weight of the animals (g) (beginning/end) First time | Body weight of the animals (g) (beginning/end) Second time | Weight of the tumor X ± SD (g) First time | Weight of the tumor X ± SD (g) Second time | Inhibition rate (%) First time | Inhibition rate (%) Second time |
|---|---|---|---|---|---|---|---|---|---|
| 10 | 100 | ip × 10qd | 8/8 | 20.3/23.6 | — | 1.41 ± 0.21*** | — | 41.98 | — |
|  | 50 | ip × 10qd | 8/8 | 20.1/2.35 | — | 1.63 ± 0.16*** | — | 32.92 | — |
| 11 | 50 | ip × 10qd | 8/8 | 18.3/23.0 | 19.8/23.8 | 1.40 ± 0.16*** | 1.35 ± 0.14*** | 44.22 | 42.8 |
|  | 25 | ip × 10qd | 8/8 | 18.7/23.4 | 19.9/24.5 | 1.78 ± 0.16 | 1.58 ± 0.09*** | 29.08 | 33.05 |
| 14 | 100 | ip × 10qd | 8/8 | 20.7/23.1 | — | 1.60 ± 0.19*** | — | 34.16 | — |
|  | 50 | ip × 10qd | 8/8 | 20.1/23.8 | — | 1.76 ± 0.25 | — | 27.57 | — |
| 15 | 100 | ip × 10qd | 8/8 | 20.3/24.0 | — | 1.65 ± 0.17*** | — | 32.10 | — |
|  | 50 | ip × 10qd | 8/8 | 20.4/23.9 | — | 1.81 ± 0.28 | — | 25.51 | — |
| 17 | 100 | ip × 10qd | 8/8 | 19.0/24.8 | 20.4/24.9 | 1.84 ± 0.48*** | 1.51 ± 0.09*** | 37.20 | 37.86 |
|  | 50 | ip × 10qd | 8/8 | 19.2/25.4 | 20.2/25.4 | 2.01 ± 0.28*** | 1.75 ± 0.09*** | 31.40 | 27.98 |
| 31 | 100 | ip × 10qd | 8/8 | 20.5/23.7 | — | 1.55 ± 0.22*** | — | 36.21 | — |
|  | 50 | ip × 10qd | 8/8 | 20.6/24.3 | — | 1.70 ± 0.12*** | — | 30.04 | — |
| 33 | 100 | ip × 10qd | 8/8 | 19.9/24.7 | 19.0/24.5 | 1.39 ± 0.15*** | 1.66 ± 0.12*** | 42.80 | 43.34 |
|  | 50 | ip × 10qd | 8/8 | 20.3/25.4 | 18.9/24.9 | 1.60 ± 0.09*** | 2.02 ± 0.18*** | 34.16 | 31.06 |
| 36 | 100 | ip × 10qd | 8/8 | 19.3/25.2 | 20.1/25.0 | 1.70 ± 0.17*** | 1.29 ± 0.13*** | 41.98 | 46.91 |
|  | 50 | ip × 10qd | 8/8 | 18.8/25.6 | 20.1/25.3 | 2.00 ± 0.28*** | 1.66 ± 0.17*** | 31.74 | 31.69 |
| 37 | 50 | ip × 10qd | 8/8 | 18.9/23.9 | 19.5/24.3 | 1.53 ± 0.14*** | 1.34 ± 0.14*** | 39.04 | 43.22 |
|  | 25 | ip × 10qd | 8/8 | 18.6/24.1 | 19.6/24.9 | 1.83 ± 0.17 | 1.67 ± 0.16 | 27.09 | 29.24 |
| 42 | 100 | ip × 10qd | 8/8 | 20.3/25.1 | 18.9/25.1 | 1.62 ± 0.12*** | 1.92 ± 0.26*** | 33.33 | 34.47 |
|  | 50 | ip × 10qd | 8/8 | 20.0/24.7 | 19.1/24.7 | 2.14 ± 0.26 | 1.89 ± 0.14 | 22.22 | 26.96 |
| 48 | 100 | ip × 10qd | 8/8 | 19.8/24.8 | 19.3/25.2 | 1.58 ± 0.08*** | 1.77 ± 0.15*** | 34.98 | 39.59 |
|  | 50 | ip × 10qd | 8/8 | 20.1/25.3 | 19.0/25.0 | 1.82 ± 0.10 | 2.09 ± 0.19 | 25.10 | 28.67 |
| 55 | 100 | ip × 10qd | 8/8 | 19.1/23.5 | 19.7/23.9 | 1.76 ± 0.10*** | 1.63 ± 0.18*** | 29.88 | 30.93 |
|  | 50 | ip × 10qd | 8/8 | 18.7/23.8 | 19.6/24.5 | 1.96 ± 0.12*** | 1.78 ± 0.19*** | 21.91 | 24.58 |
| 84 | 100 | ip × 10qd | 8/8 | 18.5/24.2 | 19.4/24.7 | 1.63 ± 0.11*** | 1.48 ± 0.15*** | 35.06 | 37.29 |
|  | 50 | ip × 10qd | 8/8 | 19.0/24.1 | 19.7/25.2 | 1.83 ± 0.11 | 1.63 ± 0.16*** | 27.09 | 30.93 |
| 86 | 20 | ip × 10qd | 8/8 | 20.0/25.2 | 18.7/23.9 | 1.42 ± 0.11*** | 1.61 ± 0.17*** | 41.56 | 45.05 |
|  | 10 | ip × 10qd | 8/8 | 20.2/24.5 | 19.1/25.1 | 1.58 ± 0.11*** | 1.84 ± 0.17*** | 34.98 | 37.20 |
| CTX | 30 | Iv × 7qd | 8/8 | 20.1/21.3 | 18.9/21.3 | 0.32 ± 0.12*** | 0.27 ± 0.11*** | 86.83 | 90.82 |
| CTX | 30 | Iv × 7qd | 8/8 | 18.8/20.2 | 19.8/21.0 | 0.28 ± 0.14*** | 0.32 ± 0.13*** | 88.69 | 86.44 |

TABLE 41-continued

The antitumor activity of β-carboline derivatives against mouse Lewis lung cancer

| Compd | Dosage (mg/ml) | Administration scheme | Number of animals (beginning/end) | Body weight of the animals (g) (beginning/end) First time | Body weight of the animals (g) (beginning/end) Second time | Weight of the tumor X ± SD (g) First time | Weight of the tumor X ± SD (g) Second time | Inhibition rate (%) First time | Inhibition rate (%) Second time |
|---|---|---|---|---|---|---|---|---|---|
| negative control | vehicle | Iv × 10qd | 16/16 | 20.2/25.9 | 19.1/25.5 | 2.43 ± 0.25 | 2.93 ± 0.29 | — | — |
| negative control | vehicle | Iv × 10qd | 16/16 | 18.9/24.2 | 19.7/25.8 | 2.51 ± 0.24 | 2.36 ± 0.23 | — | — |

Note 1:
***represents that $P < 0.01$ compared with the negative control group.

TABLE 42

The antitumor activity of β-carboline derivatives against mouse S180 sarcoma

| Compd | Dosage (mg/ml) | Administration scheme | Number of animals (beginning/end) | Body weight of the animals (g) (beginning/end) First time | Body weight of the animals (g) (beginning/end) Second time | Weight of the tumor X ± SD (g) First time | Weight of the tumor X ± SD (g) Second time | Inhibition rate (%) First time | Inhibition rate (%) Second time |
|---|---|---|---|---|---|---|---|---|---|
| 10 | 100 | ip × 10qd | 8/8 | 20.1/25.5 | — | 1.56 ± 0.17*** | — | 40.46 | — |
|  | 50 | ip × 10qd | 8/8 | 20.0/26.4 | — | 1.81 ± 0.20*** | — | 30.92 | — |
| 11 | 50 | ip × 10qd | 10/10 | 19.5/25.9 | 20.6/23.9 | 1.59 ± 0.16*** | 1.62 ± 0.38*** | 44.21 | 43.16 |
|  | 25 | ip × 10qd | 10/10 | 19.5/26.3 | 20.4/24.2 | 1.86 ± 0.18*** | 1.94 ± 0.16*** | 34.74 | 31.93 |
| 14 | 100 | ip × 10qd | 8/8 | 19.9/25.5 | — | 1.78 ± 0.20*** | — | 32.06 | — |
|  | 50 | ip × 10qd | 8/8 | 19.8/26.7 | — | 1.98 ± 0.28 | — | 24.43 | — |
| 15 | 100 | ip × 10qd | 8/8 | 19.9/26.0 | — | 1.69 ± 0.16*** | — | 35.50 | — |
|  | 50 | ip × 10qd | 8/8 | 19.8/26.4 | — | 2.00 ± 0.16 | — | 23.66 | — |
| 17 | 100 | ip × 10qd | 10/10 | 19.3/24.2 | 18.6/25.3 | 1.73 ± 0.16*** | 1.81 ± 0.20*** | 35.21 | 32.96 |
|  | 50 | ip × 10qd | 10/10 | 19.2/24.7 | 18.5/25.9 | 2.03 ± 0.24 | 2.02 ± 0.21 | 23.97 | 25.19 |
| 31 | 100 | ip × 10qd | 8/8 | 20.0/26.1 | — | 1.65 ± 0.16*** | — | 37.02 | — |
|  | 50 | ip × 10qd | 8/8 | 19.7/26.7 | — | 1.88 ± 0.21 | — | 28.04 | — |
| 33 | 100 | ip × 10qd | 10/10 | 19.4/24.6 | 18.6/25.1 | 1.53 ± 0.15*** | 1.62 ± 0.30*** | 42.70 | 40.00 |
|  | 50 | ip × 10qd | 10/10 | 19.4/24.4 | 18.7/25.6 | 1.78 ± 0.17*** | 1.83 ± 0.19*** | 33.33 | 32.22 |
| 36 | 100 | ip × 10qd | 10/10 | 19.0/24.5 | 18.7/25.5 | 1.52 ± 0.15*** | 1.62 ± 0.12*** | 43.07 | 40.00 |
|  | 50 | ip × 10qd | 10/10 | 19.1/24.9 | 18.3/25.3 | 1.87 ± 0.16*** | 1.86 ± 0.28*** | 29.96 | 31.11 |
| 37 | 50 | ip × 10qd | 10/10 | 19.7/26.3 | 20.6/24.7 | 1.87 ± 0.13*** | 1.91 ± 0.23*** | 34.39 | 32.98 |
|  | 25 | ip × 10qd | 10/10 | 19.6/26.9 | 20.4/25.1 | 2.17 ± 0.18 | 2.16 ± 0.27 | 23.86 | 24.21 |
| 42 | 100 | ip × 10qd | 10/10 | 19.2/24.3 | 18.9/25.1 | 1.92 ± 0.25 | 2.02 ± 0.36 | 28.09 | 25.15 |
|  | 50 | ip × 10qd | 10/10 | 19.5/24.7 | 18.4/25.6 | 2.16 ± 0.23 | 2.14 ± 0.23 | 19.10 | 20.74 |
| 48 | 100 | ip × 10qd | 10/10 | 19.4/24.8 | 18.5/26.0 | 1.84 ± 0.11*** | 1.83 ± 0.16*** | 31.09 | 32.22 |
|  | 50 | ip × 10qd | 10/10 | 19.4/24.8 | 18.6/25.8 | 2.15 ± 0.39 | 2.11 ± 0.25 | 19.48 | 21.85 |
| 55 | 100 | ip × 10qd | 10/10 | 19.4/26.7 | 20.3/24.9 | 2.02 ± 0.22*** | 2.05 ± 0.17*** | 29.12 | 28.07 |
|  | 50 | ip × 10qd | 10/10 | 19.8/27.0 | 20.9/24.8 | 2.18 ± 0.23 | 2.28 ± 0.18 | 23.51 | 20.00 |
| 84 | 100 | ip × 10qd | 10/10 | 19.7/26.4 | 20.2/25.0 | 1.79 ± 0.27*** | 1.79 ± 0.16*** | 37.19 | 37.19 |
|  | 50 | ip × 10qd | 10/10 | 19.6/26.8 | 20.4/25.4 | 2.01 ± 0.24*** | 1.96 ± 0.16*** | 29.47 | 31.23 |
| 86 | 20 | ip × 10qd | 10/10 | 19.0/23.7 | 18.9/24.4 | 1.63 ± 0.26*** | 1.59 ± 0.17*** | 38.95 | 41.11 |
|  | 10 | ip × 10qd | 10/10 | 19.3/24.5 | 18.7/24.9 | 1.84 ± 0.16*** | 1.92 ± 0.20 | 31.09 | 28.89 |
| CTX | 30 | ip × 7qd | 10/10 | 19.4/20.9 | 19.8/23.2 | 0.33 ± 0.14*** | 0.36 ± 0.13*** | 87.55 | 87.37 |
| CTX | 30 | ip × 7qd | 10/10 | 18.7/22.3 | 20.3/20.9 | 0.33 ± 0.12*** | 0.27 ± 0.13*** | 87.93 | 90.53 |
| negative control | vehicle | iv × 10qd | 20/20 | 19.2/24.6 | 19.6/27.0 | 2.67 ± 0.30 | 2.85 ± 0.33 | — | — |
| negative control | vehicle | iv × 10qd | 10/10 | 18.8/25.9 | 20.5/25.3 | 2.70 ± 0.31 | 2.85 ± 0.33 | — | — |

Note 1:
***represents that $P < 0.01$ compared with the negative control group.

2. Results
2.1 Observations of Ordinary Symptoms

After the administration of all 14 compounds tested, no symptoms of nervous toxicity, such as quivering, jumping and twisting, occurred. It was thus demonstrated that all compounds do not have nervous toxicity.

2.2 Results of the Anti-Tumor Activity

The results of the therapeutic effect on Lewis lung cancer cells are shown in table 41. See FIG. 13 for the real image of the therapeutic effect. The results of the therapeutic effect on S180 sarcoma are shown in table 42. See FIG. 14 for the real image of the therapeutic effect.

For the sake of comparison, the test results of the in vivo anti-tumor therapeutic effect are shown in table 43.

It can be seen from the results shown in table 43 that (1) among all 22 compounds tested, there are 7 compounds (compounds 4, 6, 10, 11, 33, 36 and 86) that exhibit an inhibition rate of tumors greater than 40% against both Lewis lung cancer cells and S180 sarcomata, and there are two compounds (compounds 3 and 37) that exhibit an inhibition rate of tumors greater than 40% merely against Lewis lung cancer cells; (2) compounds 6 and 36 have the strongest anti-tumor effect on Lewis lung cancer cells and have an inhibition rate of up to 46.9%; (3) among all 22 compounds tested, except compounds 14, 15, 27 and 55 have an anti-tumor activity against Lewis lung cancer cells a little worse than or equivalent to that of harmines (compound 1), all the other compounds anti-tumor activity is higher than that of harmines, and (4) Lewis lung cancer cells are more sensitive to the anti-tumor activity of β-carboline alkaloid derivatives than S180 sarcoma.

TABLE 43

The antitumor activity of β-carboline derivatives in vivo

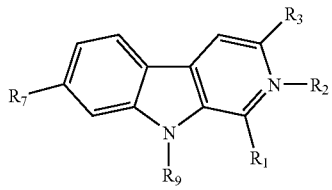

| Compd | $R_1$ | $R_2$ | $R_3$ | $R_7$ | $R_9$ | Inhibition rate (%) Lewis cancer | Inhibition rate (%) S180 sarcomata |
|---|---|---|---|---|---|---|---|
| 1* | $CH_3$ | H | H | $CH_3O$ | H | 34.1 | 15.3 |
| 2* | $CH_3$ | H | H | $CH_3O$ | $CH_3$ | 38.1 | 32.1 |
| 3* | $CH_3$ | H | H | $CH_3O$ | $C_2H_5$ | 42.0 | 37.6 |
| 4* | $CH_3$ | H | H | $CH_3O$ | $n$-$C_4H_9$ | 44.0 | 40.9 |
| 6* | $CH_3$ | H | H | $CH_3O$ | $CH_2C_6H_5$ | 46.9 | 45.2 |
| 10 | H | H | $CO_2C_2H_5$ | H | H | 41.98 | 40.46 |
| 11 | $CH_3$ | H | $CO_2C_2H_5$ | H | H | 44.22 | 44.21 |
| 14 | $C_6H_5$ | H | $CO_2CH_3$ | H | H | 32.06 | 34.16 |
| 15 | $C_6H_5$-p-$OCH_3$ | H | $CO_2CH_3$ | H | H | 35.50 | 32.10 |
| 16 | $C_6H_5$-p-OH | H | $CO_2CH_3$ | H | H | 37.86 | 32.96 |
| 17* | H | H | COOH | H | H | 33.4 | 32.2 |
| 26* | H | H | $CO_2CH_3$ | H | $CH_3$ | 35.0 | 31.1 |
| 27* | H | H | $CO_2CH_3$ | H | $C_2H_5$ | 30.5 | 29.0 |
| 31 | H | H | $CO_2C_2H_5$ | H | $C_2H_5$ | 37.02 | 36.21 |
| 33 | H | H | $CO_2C_2H_5$ | H | $CH_2C_6H_5$ | 43.3 | 42.11 |
| 36 | H | H | COOH | H | $n$-$C_4H_9$ | 46.91 | 43.07 |
| 37 | H | H | COOH | H | $CH_2C_6H_5$ | 43.22 | 34.39 |
| 42 | H | H | $CH_2OH$ | H | $CH_2C_6H_5$ | 34.47 | 28.09 |
| 48 | H | H | COOH | H | $(CH_2)_3C_6H_5$ | 39.59 | 32.22 |
| 55 | H | H | $NHCO_2C_2H_5$ | H | $CH_2C_6H_5$ | 30.93 | 29.12 |
| 84 | H | H | H | H | $CH_2C_6H_5$ | 37.29 | 37.19 |
| 86 | H | $CH_2C_6H_5$ | $CO_2C_2H_5$ | H | $CH_2C_6H_5$ | 41.56 | 41.11 |

Example 124

DNA Photocleavage Effect of β-Carboline Derivatives

Materials and Methods

1. Materials
(1) Instruments
DYY-2C electrophoresis apparatus (Beijing Liuyi Instrument Factory), DYCP-31D electrophoresis cell (Beijing Liuyi Instrument Factory) and gel image system was used.
(2) Reagents
Plasmid pGBK (8.0 Kb, stored by this lab), agarose, Tris-HCl buffer solution (pH: 7.5), and E.Z.N.A. plasmid minipreps kit I (OmegaBio-Tek, U.S.) was used.
Chemicals: compounds 1, 2, 3, 4, 5, 6, 7, 8, 11, 13, 17, 34, 35, 36, 37, 56, 57, 58, 68, 69, 70, 80, 81, 82, 83 and 84. See table 1 for the structures of said compounds.

2. Methods
(1) Plasmids pGBK
Plasmid pGBK was prepared using *Escherichia coli* culture and then was purified using an E.Z.N.A. Plasmid Minipreps Kit I. The plasmid was suspended in Tris-EDTA buffer and detected with agarose gel electrophoresis, and then stored at −20° C.
(2) DNA Photocleavage Examination
The experiments were carried out in a volume of 20 μl containing 0.3 μg of plasmid pGBK DNA in Tris-HCl buffer (50 mM Tris-HCl, pH 7.5) and various harmine derivatives with different concentration. Reaction volumes were held in polyethylene microcentrifuge tubes, and then irradiated under a mercury-vapor ultraviolet light (8 w, 365 nm, 5 cm distance). Samples were irradiated for 2 h at room temperature. Identical treatments were placed in dark at room temperature. After irradiation, a 2 μl of a mixture containing 50% sucrose and 0.25% bromophenol blue was added to the irradiated solution. Samples were analyzed by electrophoresis on 0.7% agarose horizontal slab gel containing 0.5 ug/mL-1 ethidium bromide in Tris-EDTA buffer (40 mM Tris, 20 mM acetic acid, 1 mM EDTA, pH 8.0). Untreated pGBK DNA was used as control. Electrophoretic analyses were carried out at 100 Vcm-1 for 1 h. Gels were photographed under UV light with Bio-Rad digital camara.
3. Results
According to the ratio of the circular nicked DNA formed under such conditions to the supercoiled DNA, the photo-induced DNA cleaving abilities of various β-carboline derivatives were confirmed.
The results are shown in FIGS. 1A-D.
We can primarily arrive at the following structure-activity relationships according to the above results: (1) the photocleavage activity of β-carboline derivatives is dependent on the presence, position and properties of the substituents on the β-carboline ring, and (2) electron-releasing substituents on the β-carboline ring facilitate the photo-induced DNA cleavage ability, whereas electron-withdrawing substituents were detrimental to their DNA cleavage activity.

Example 125

DNA Thermal Denaturation Studies of β-Carboline Derivatives

1. Materials

Instruments: UV 2501PC spectrograph (Shimadzu, Japan), SP-752 UV spectrophotometer (installed with constant temperature water bath accessory and analysis software, Shanghai Spectrograph Plant), CT-DNA (Sigma), PE buffer solution (1 mM $Na_2HPO_4$, 0.1 mM EDTA, pH 7.6) were used.

Chemicals: 19 β-carboline derivatives: 1, 2, 3, 4, 5, 6, 7, 8, 33, 36, 39, 42, 49, 66, 80, 81, 82, 83, and 84. See table 2 for their structures. Adriamycin hydrochloride and camptothecin (Sigma Company).

2. Methods (1) Determination of $_\Delta T_m$

Experiments were carried out in PE buffer (1 mM Na2HPO4, 0.1 mM EDTA, pH 7.6) in a thermostatically controlled cell hold, and the quartz cuvette (1 cm path length) was heated by circulating water at a heating rate of 0.5° C./min from 25 to 95° C. Amsacrine and Doxorubicin Hydrochloride were used as standards. In all cases, the concentration of CT-DNA was 15 ug/ml. The 'melting' temperature $T_m$ was taken as the mid-point of the hyperchromic transition.

According to the above operational conditions, 20 uM various β-carboline derivatives were added each time, and the changes of the Tm curves prior to the addition of the compounds and after the addition of the compounds were observed. ΔTm value of each compound was calculated according to the following formula:

$$_\Delta T_m = T_m^{drug\text{-}DNA\ complex} - T_m^{DNA\ alone}$$

The $_\Delta$Tm of each compound was calculated, Experiments were repeated three times, and an average value was calculated.

(2) UV Absorption Spectrum Method

CT-DNA (40 ug/ml) was added into a PE suffer solution (pH7.6), and its scan curve was identified by a UV 2501PC UV spectrograph at a wavelength of from 200 to 400 nm. Compounds to be tested (20 uM) were added into the PE buffer solution, and its scan curve was identified by the spectrograph at a wavelength of from 200 to 400 nm. CT-DNA (40 ug/ml) and compounds to be tested (20 uM) were added into the PE buffer solution. The mixture was cultured at 37° C. for 2 h, and its scan curve was identified by the UV spectrograph at a wavelength of from 200 to 400 nm. A curve showing that DNA did not react with the medicaments tested was calculated by the addition of the scan curve of CT-DNA with the scan curve of the compounds tested to calculate the OD value at 260 nm of the curve. After that, the OD value at 260 nm of the scan curve of the medicaments tested and that of the CT-DNA mixture OD value at 260 nm of the scan curve were calculated and compared to determine the influences of the medicaments tested on the UV absorption spectrum of the DNA molecules.

Results (1) Influences of β-Carboline Derivatives on the $T_m$ of the CT-DNA

Figure 2:
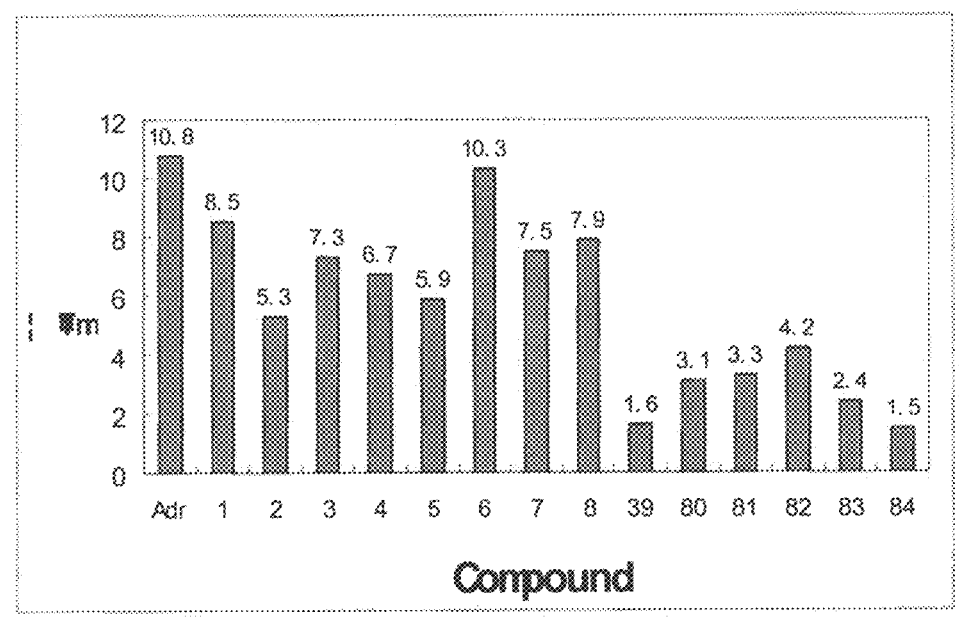
FIG. 2 illustrates the effect of binding by β-carboline derivatives on the thermal stability of the CT-DNA.

See table 44 for the influences of β-carboline alkaloid derivatives on the Tm value of the CT-DNA, and FIG. 2 for the graphic exhibition. Under the conditions of these tests, the Tm value of CT-DNA is 61° C. We can see from the figures that β-carboline derivatives can increase the Tm value of CT-DNA and that compound 6 has the greatest influence on the Tm value of the CT-DNA. Compound 6 increased the Tm value of the CT-DNA by 10.3° C., which is equivalent to the insertion effect of adriamycin ($_\Delta$Tm=10.8° C.) on the positive control group. The influence of compound 84 on the Tm value of the CT-DNA is relatively small, the $_\Delta$Tm value is only 1.5° C. In particular, we also observed in the tests that the camptothecin for the positive control group and β-carboline compounds 33, 36 and 42 reduced the Tm of the CT-DNA. The ΔTm values are respectively −2.5° C. (camptothecin), −1.2° C. (compound 33), −1.5° C. (compound 36) and −0.3° C. (compound 42).

TABLE 44

Effect of binding by β-carboline derivatives on the thermal stability of the CT-DNA

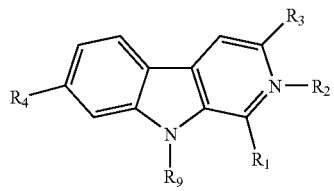

| Compounds | $R_1$ | $R_2$ | $R_3$ | $R_7$ | $R_9$ | ΔTm |
|---|---|---|---|---|---|---|
| 1 | $CH_3$ | H | H | $CH_3$ | H | 8.5 |
| 2 | $CH_3$ | H | H | $CH_3$ | $CH_3$ | 5.3 |
| 3 | $CH_3$ | H | H | $CH_3$ | $C_2H_5$ | 7.3 |
| 4 | $CH_3$ | H | H | $CH_3$ | n-$C_4H_9$ | 6.7 |
| 5 | $CH_3$ | H | H | $CH_3$ | $C_2H_4OH$ | 5.9 |
| 6 | $CH_3$ | H | H | $CH_3$ | $CH_2C_6H_5$ | 10.3 |
| 7 | $CH_3$ | H | H | $CH_3$ | $CH_2C_6F_5$ | 7.5 |
| 8 | $CH_3$ | H | H | $CH_3$ | $(CH_2)_3C_6H_5$ | 7.9 |
| 33 | $CH_3$ | H | $COOC_2H_5$ | H | $CH_2C_6H_5$ | −1.2 |
| 36 | H | H | COOH | H | n-$C_4H_9$ | −1.5 |
| 39 | H | H | $COOC_4H_9$ | H | $C_2H_5$ | 1.6 |
| 42 | H | H | $CH_2OH$ | H | $CH_2C_6H_5$ | −0.3 |
| 80 | H | H | H | H | H | 3.1 |
| 81 | H | H | H | H | $CH_3$ | 3.3 |
| 82 | H | H | H | H | $C_2H_5$ | 4.2 |
| 83 | H | H | H | H | n-$C_4H_9$ | 2.4 |
| 84 | H | H | H | H | $CH_2C_6H_5$ | 1.5 |
| Adriamycin | | | | | | 10.8 |
| Camptothecin | | | | | | −2.5 |

(2) Effect of Absorbance by β-Carboline Derivatives on the UV Spectrum of the CT-DNA.

Figure 3:
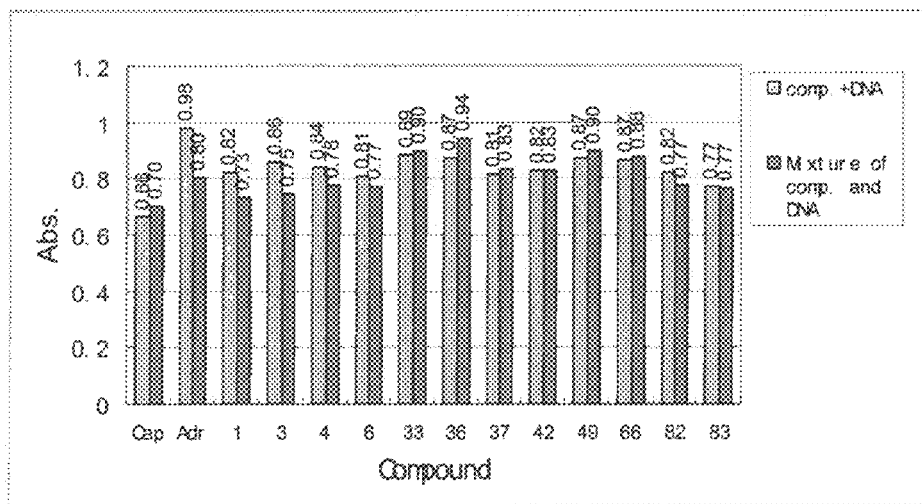
FIG. 3 illustrates the effect of absorbance by β-carboline derivatives on the UV spectrum of the CT-DNA.
Figure 4A:
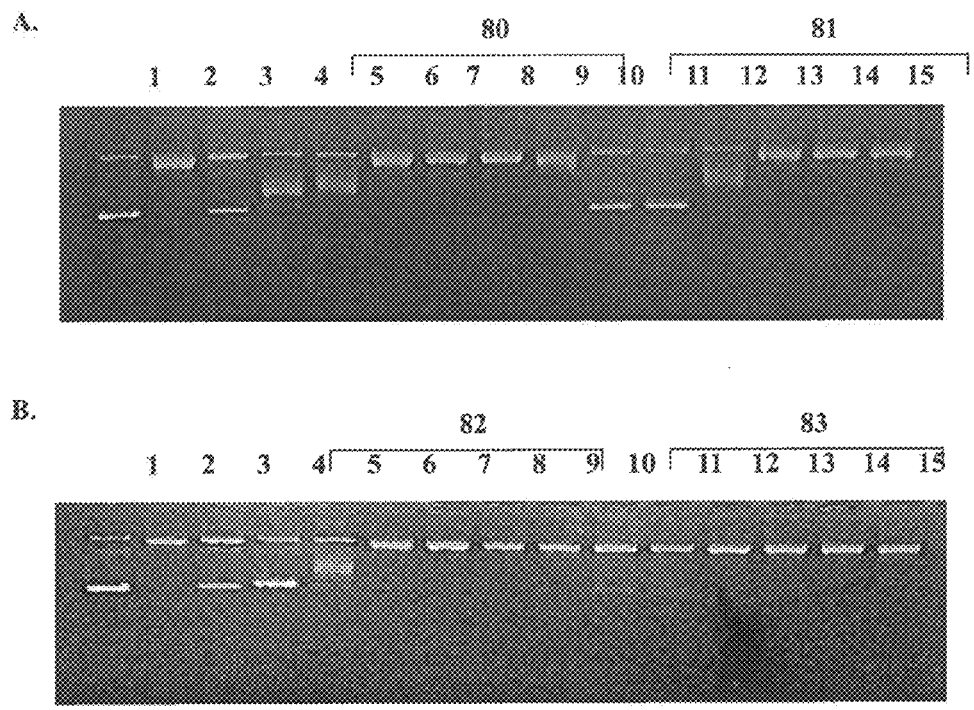

See FIG. 3 for the influence of β-carboline derivatives on the UV absorption spectrum of CT-DNA. It can be seen from the figure that (1) compounds 1, 3, 4, 6, 82 and 83 and the adriamycin can reduce the UV absorption of DNA, and the influence of adriamycin is the most significant, followed by compound 3; and (2) on the contrary, compounds 36, 37, 43, 49 and 66 and the camptothecin can increase the UV absorption of DNA, and the influence of compound 36 on the increase of UV absorption value of the DNA is the most obvious.

REFERENCES

1. Duan Jinao, Zhou Ronghan, Zhao Shouxun et al., Study I on the Components of *Peganum* multisectum Bobr, Components of Seed alkaloids and Anti-Tumor Activity thereof, *Journal of China Pharmaceutical University,* 1998, 29: 21-23
2. Li Chunjie, Liu Dexi, Mamtiyimin et al., Isolation and Determination of the Anti-Cancer Chemical Components of Harmel *Peganum* and Pharmacological Experimental Study thereof, *Journal of Xinjiang Medical College*, 1987, 10 (1): 27-30
3. Pan Qichao, Yang Xiaoping, Li Guowei et al., Anti-Tumor Effect of Mixed Alkaloid L of the Seeds of Harmel *Peganum, Cancer,* 1985, 6(5): 40-41
4. Pan Qichao, Yang Xiaoping, Li Guowei et al., Anti-Tumor Effect of Indole Alkaloid of the Seeds of Harmel *Peganum, Cancer,* 1985, 4(4): 192-194
5. Pan Qichao, Yang Xiaoping, Li Chunjie et al., Study on Pharmacological Effect of Harmaline, *Academic Journal of Sun Yat-Sen University of Medical Sciences,* 1997, 18(3): 165-167
6. Pan Qichao, Yang Xiaoping, and Li Chunjie, In Vivo and In Vitro Effect of Harmaline on Inhibiting Liver Cancer and Gastric Carcinoma in Humans, *Cancer,* 1991, 10(6): 463-465
7. Xu Zhaodong and Pan Qichao, Study on the Anti-Cancer Effect of Harmel *Peganum, Cancer,* 1989; 8(2); 94-97
8. Yang Xiaoping, Pan Qichao and L1 Chunjie, Influences of Harmaline on the Growth of Transplanted Tumors in Nude Mice, *Beijing Laboratory Animal Science,* 1992, 9 (4): 54
9. Yang Xiaoping, Pan Qichao, and Li Guowei, Effect of Harmine on Human Cervical Carcinoma Cells (Hela) *In Vitro, Academic Journal of Sun Yat-Sen University of Medical Sciences,* 1986, 7(1): 44-46
10. Hu Haitang and Pan Qichao, Influences Harmaline on the Period Dynamics of Liver Cancer Cells in Mice, *Cancer,* 1993; 12 (6): 489-491
11. Xie Yan and Luo Tianxi, Study on Harmaline-Induced Apoptosis in Human Cervical Carcinoma Cells (Hela), *Cancer,* 1998; 18 (3): 131-133
12. Szantay C, Blusko G, Honty K, et al. in: A. Brossi (Ed.). The Alkaloids, Vol. 27, Academic Press, New York, 1986
13. Budavari, S. (Ed.), The Merck Index, Merk & Co. Inc., Rahway, N.J., 11th edn., 1989

The invention claimed is:

1. A compound of the following formula (I):

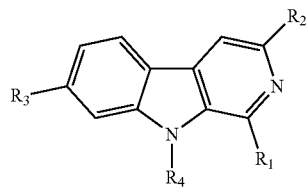

and its pharmacologically acceptable salts, wherein
$R_1$ is methyl;
$R_2$ is $COOC_2H_5$;
$R_3$ is hydrogen; and
$R_4$ is phenylpropyl;
whereby the compound is ethyl 9-phenylpropyl-1-methyl-β-carboline-3-carboxylate.

2. A pharmaceutical composition for treating tumors, comprising as an active ingredient at least one therapeutically effective amount of a compound of formula I according to claim 1, alone or combined with one or more pharmaceutically acceptable, inert and non-toxic excipients or carriers.

3. A method of treating tumors in a mammalian subject, the method comprising administration of a medicament comprising a compound of claim 1.

* * * * *